(12) United States Patent
Kipps et al.

(10) Patent No.: US 7,070,771 B1
(45) Date of Patent: Jul. 4, 2006

(54) METHODS OF EXPRESSING CHIMERIC MOUSE AND HUMAN CD40 LIGAND IN HUMAN CD40+ CELLS

(75) Inventors: Thomas J. Kipps, Solana Beach, CA (US); Sanjai Sharma, La Jolla, CA (US); Mark Cantwell, La Jolla, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 08/982,272

(22) Filed: Dec. 1, 1997

Related U.S. Application Data

(60) Provisional application No. 60/032,145, filed on Dec. 9, 1996.

(51) Int. Cl.
*A61K 48/00* (2006.01)
*C12N 15/87* (2006.01)
*C07H 21/04* (2006.01)

(52) U.S. Cl. ............... 424/93.21; 424/93.1; 424/93.71; 424/93.2; 424/93.7; 435/440; 435/455; 435/252.3; 435/320.1; 435/325; 536/23.1; 536/23.4; 536/23.5

(58) Field of Classification Search ............... 424/93.1, 424/93.2, 93.71; 435/440, 320.1; 536/23.1
See application file for complete search history.

(56) References Cited

U.S. PATENT DOCUMENTS

| | | | |
|---|---|---|---|
| 4,990,455 A | 2/1991 | Yamagishi et al. | |
| 5,422,104 A | 6/1995 | Fiers et al. | |
| 5,480,981 A | 1/1996 | Goodwin et al. | |
| 5,486,463 A | 1/1996 | Lesslauer et al. | |
| 5,519,119 A | 5/1996 | Yamada et al. | |
| 5,540,926 A | 7/1996 | Aruffo et al. | |
| 5,565,321 A | 10/1996 | Spriggs et al. | |
| 5,573,924 A | 11/1996 | Beckmann et al. | |
| 5,606,023 A | 2/1997 | Chen et al. | |
| 5,817,516 A | 10/1998 | Kehry et al. | 435/377 |
| 5,861,310 A * | 1/1999 | Freeman et al. | |
| 6,016,832 A * | 1/2000 | Vars et al. | |
| 6,017,527 A * | 1/2000 | Maraskovsky et al. | |

FOREIGN PATENT DOCUMENTS

| | | |
|---|---|---|
| EP | 0 317 641 A | 5/1989 |
| EP | 0 585 943 A2 | 3/1993 |
| EP | 0 675 200 A | 10/1995 |
| EP | WO 96 18413 A | 6/1996 |
| EP | 1 016 721 A | 7/2000 |
| WO | WO 91 02540 A | 3/1991 |
| WO | WO 93/08207 | 4/1993 |
| WO | WO 94/04570 | 3/1994 |
| WO | WO 94 04680 A | 3/1994 |
| WO | WO 94/17196 | 8/1994 |
| WO | WO 95/17202 | 6/1995 |
| WO | WO 95 18819 A | 7/1995 |
| WO | WO 95 32627 A | 12/1995 |
| WO | WO 96/14876 | 5/1996 |
| WO | WO 98 21232 A | 5/1998 |

OTHER PUBLICATIONS

Skolnick Trends in Biotechnology 18:34–39 (2000).*
NGO et al. In the Protein Folding Problem and Tertiary Structure Prediction 1994 Merz et al (ED) Birkhauser Beuton MA pp. 433, 492–495.*
Yellin et al. J. Immunol. 153: 666–674 (1994).*
Alderson et al. J Exp. Med. 178: 669–674 (1993).*
Nadler, Lee M., "The Malignant Lymphomas," *Harrison's Principles of Internal Medicine*, Wilson et al., eds., McGraw–Hill, New York, Chapter 302, pp. 1599–1612.
Thomas, J. Alero et al., "Epstein–Barr Virus–Associated Lymphoproliferative Disorders in Immunocompromised Individuals," *Advances in Cancer Research*, Woude et al., eds., Academic Press, Inc., 57:329–380 (1991).
Fanslow, William C. et al., "Structural characteristics of CD40 ligand that determine biological function," *Seminars in Immunology*, 6:267–278 (1994).
Armitage, Richard J. et al., "Molecular and biological characterization of a murine ligand for CD40," *Nature*, 357:80–82 (1992).
Hollenbaugh, Diane et al., "The human T cell antigen gp39, a member of the TNF gene family, is a ligand for the CD40 receptor: expression of a soluble form of gp39 with B cell co–stimulatory activity," *The EMBO Journal*, 11:4313–4321 (1992).
Zhang, Haidi et al., "Amelioration of Collagen–induced Arthritis by CD95 (Apo–1/Fas)–ligand Gene Transfer," *J. Clin. Invest.*, 100:1951–1957 (1997).
Wiley, James A. et al., "Exogenous CD40 Ligand Induces a Pulmonary Inflammation Response," *Journal of Immunology*, 158:2932–2938 (1997).
Tracey, Kevin J. et al., "Tumor Necrosis Factor: A Pleiotropic Cytokine and Therapeutic [sic] Terget," *Annu. Rev. Med.*, 45:491–503 (1994).
Galle, Peter R. et al., "Involvement of the CD95 (APO–1/Fas) Receptor and Ligand in Liver Damage," *J. Exp. Med.*, 182:1223–1230 (1995).

(Continued)

*Primary Examiner*—Phillip Gambel
(74) *Attorney, Agent, or Firm*—Foley & Lardner LLP

(57) ABSTRACT

This invention relates to genes which encode accessory molecule ligands, such as the CD40 ligand and their use for immunomodulation, vaccination and treatments of various human diseases, including malignancies and autoimmune diseases. This invention also describes the use of accessory molecule ligands which are made up of various domains and subdomain portions of molecules derived from the tumor necrosis factor family. The chimeric molecules of this invention contain unique properties which lead to the stabilization of their activities and thus greater usefulness in the treatment of diseases. Vectors for expressing genes which encode the accessory molecule ligands of this invention are also disclosed.

15 Claims, 31 Drawing Sheets

OTHER PUBLICATIONS

Sato, Ken et al., "An aggressive nasal lymphoma accompanied by high levels of soluble Fas ligand," *British Journal of Haematolog*, 94:379–382 (1996).

van Oers, M. H. J. et al., "Expression and Release of CD27 in Human B–Cell Malignancies," *Blood*, 82:3430–3436 (1993).

Smith, Matthew M. et al., "Rapid Identification of Highly Active and Selective Substrates for Stromelysin and Matrilysin Using Bacteriophage Peptide Display Libraries," *The Journal of Biological Chemistry*, 270:6440–6449 (1995).

Nagase, H. et al., "Human Matrix Metalloproteinase Specificity Studies Using Collagen Sequence–Based Synthetic Peptides," *Biopolymers (Peptide Science)*, 40:399–416 (1996).

Cantwell, Mark J. et al., "Adenovirus Vector Infection of Chronic Lymphocytic Leukemia B Cells," *Blood*, 88:4676–4683 (1996).

Woll, P. J. et al., "Gene therapy for lung cancer," *Annals of Oncology*, 6 Suppl. 1:S73–S77 (1995).

Smith, K. T. et al., "Gene delivery systems for use in gene therapy: an overview of quality assurance and safety issues," *Gene Therapy*, 3:190–200 (1996).

Cooper, Mark J., "Noninfectious Gene Transfer and Expression Systems for Cancer Gene Therapy," *Seminars in Oncology*, 23:172–187 (1996).

Shaughnessy, Elizabeth et al., "Parvoviral Vectors for the Gene Therapy of Cancer," *Seminars in Oncology*, 23:159–171 (1996).

Glorioso, J. C. et al., "Development and application of herpes simplex virus vectors for human gene therapy," *Annu. Rev. Microbiol.*, 49:675–710 (1995).

Flotte, T. R. et al., "Adeno–associated virus vectors for gene therapy," *Gene Therapy*, 2:357–362 (1995).

Randrianarison–Jewtoukoff, Voahangy et al., "Recombinant Adenoviruses as Vaccines," *Biologicals*, 23:145–157 (1995).

Kohn, Donald B., "The current status of gene therapy using hematopoietic stem cell," *Current Opinion in Pediatrics*, 7:56–63 (1995).

Vile, R. G. et al., "Retroviruses as vectors," *British Medical Bulletin*, 51:12–30 (1995).

Russell, Stephen J., "Replicating vectors for cancer therapy: a question of strategy," *Seminars in Cancer Biology*, 5:437–443 (1994).

Ali, Munaf et al., "The use of DNA viruses as vectors for gene therapy," *Gene Therapy*, 1:367–384 (1994).

Tesselaar, Kiki et al., "Characterization of Murine CD70, the Ligand of the TNF Receptor Family Member CD27," *The Journal of Immunology*, 159:4959–4965 (1997).

Peitsch, Manuel C. et al., "A 3–D model for the CD40 ligand predicts that it is a compact trimer similar to the tumor necrosis factors," *International Immunology*, 5:233–238 (1993).

Horton, Robert M., "PCR–mediated Recombination and Mutagenesis," *Molecular Biotechnology*, 3:93–99 (1995).

Ali, Stuart Alvaro et al., "PCR–Ligation–PCR Mutagenesis: A Protocol for Creating Gene Fusions and Mutations," *BioTechniques*, 18:746–750 (1995).

Vilardaga, J. P. et al., "Improved PCR Method for High–Efficiency Site–Directed Mutagenesis Using Class 2S Restriction Enzymes," *BioTechniques*, 18:604–606 (1995).

Majumder, Kumud et al., "Background–minimized Cassette–Mutagenesis by PCR Using Cassette–specific Selection Markers: A Useful General Approach for Studying Structure–Function Relationships of Multisubstrate Enzymes," *PCR Methods and Applications*, 4:212–218 (1995).

Boles, Eckhard et al., "A rapid and highly efficient method for PCR–based site–directed mutagenesis using only one new primer," *Curr. Genet.*, 28:197–198 (1995).

Vallejo, Abbe N. et al., "In Vitro Synthesis of Novel Genes: Mutgenesis and Recombination by PCR," *PCR Methods and Applications*, 4:S123–S130 (1994).

Henkel, Thomas et al., "Functional Analysis of Mutated cDNA Clones by Direct Use of PCR Products in in Vitro Transcription/Translation Reactions," *Analytical Biochemistry*, 214:351–352 (1993).

Tessier, Daniel C. et al., "PCR–Assisted Large Insertion/Deletion Mutagenesis," *BioTechniques*, 15:498–501 (1993).

Morrison, Hilary G. et al., "A PCR–Based Strategy for Extensive Mutagenesis of a Target DNA Sequence," *BioTechniques*, 14:454–457 (1993).

Cadwell, R. Craig et al., "Randomization of Genes by PCR Mutagenesis," *PCR Methods and Applications*, 2:28–33 (1992).

Stappert, Jörg et al., "A PCR method for introducing mutations into cloned DNA by joining an internal primer to a tagged flanking primer," *Nucleic Acids Research*, 20:624 (1992).

Kunkel, Thomas A., "Rapid and efficient site–specific mutagenesis without phenotypic selection," *Proc. Natl. Acad. Sci. USA*, 82:488–492 (1985).

Kunkel, Thomas A. et al., "Rapid and Efficient Site–Specific Mutagenesis without Phenotypic Selection," *Methods in Enzymology*, 154:367–382 (1987).

Okayama, Hiroto and Paul Berg, "A cDNA Cloning Vector That Permits Expression of cDNA Inserts in Mammalian Cells," *Molecular and Cellular Biology*, 3:280–289 (1983).

Cosman, David et al., "Cloning, sequence and expression of human interleukin–2 receptor," *Nature*, 312:768–771 (1984).

Berman, Joan W. et al., "Gene transfer in lymphoic cells: Expression of the Thy–1.2 antigen by Thy–1.1 BW5147 lymphoma cells transfected with unfractionated cellular DNA," *Proc. Natl. Acad. Sci. USA*, 81:7176–7179 (1984).

Deans, Robert J. et al., "Expression of an immunoglobulin heavy chain gene transfected into lymphocytes," *Proc. Natl. Acad. Sci. USA*, 81:1292–1296 (1984).

Brody, Steven L. et al., "Adenovirus–mediated in Vivo Gene Transfer," *Ann. N. Y. Acad. Sci.*, 716:90–103 (1994).

Srivastava, Arun, "Parovirus–Based Vectors for Human Gene Therapy," *Blood Cells*, 20:531–538 (1994).

Jolly, Douglas, "Viral vector systems for gene therapy," *Cancer Gene Therapy*, 1:51–64 (1994).

Russell, S. J., "Replicating Vectors for Gene Therapy of Cancer: Risks, Limitations and Prospects," *European Journal of Cancer*, 30A:1165–1171 (1994).

Yee, Jiing–Kuan et al., "Generation of High–Tier Pseudotyped Retroviral Vectors with Very Broad Host Range," *Methods in Cell Biology*, Chapter 5, 43:99–112 (1994).

Boris–Lawrie, Kathleen A. et al., "Recent advances in retrovirus vector technology," *Current Opinion in Genetics and Development*, 3:102–109 (1993).

Tolstoshev, Paul, "Gene therapy, concepts, current trials and future directions," *Annu. Rev. Pharmacol. Toxicol.*, 33:573–596 (1993).

Carter, Barrie J., "Adeno–associated virus vectors," *Current Opinion in Biotechnology*, 3:533–539 (1992).

Raper, Steven E. et al., "Safety and Feasibility of Liver–Directed Ex Vivo Gene Therapy for Homozygous Familial Hypercholesterolemia," *Annals of Surgery*, 223:116–126 (1996).

Lu, Li et al., "Stem cells from bone marrow, umbilical cord blood and peripheral blood for clinical application: current status and future application," *Critical Reviews in Oncology/Hematology*, 22:61–78 (1996).

Koc, Omer N. et al., "Transfer of Drug Resistance Genes Into Hematopoietic Progenitors to Improve Chemotherapy Tolerance," *Seminars in Oncology*, 23:46–65 (1996).

Fisher, Lisa J. et al., "In vitro and ex vivo gene transfer to the brain," *Current Opinion in Neurobiology*, 4:735–741 (1994).

Goldspiel, Barry R. et al., "Human gene therapy," *Clinical Pharmacy*, 12:488–505 (1993).

Dilloo, Dagmar et al., "CD40 Ligand Induces an Antileukemia Immune Response In Vivo," *Blood*, 90:1927–1933 (1997).

Schultze, Joachim L. et al., "Autologous Tumor Infiltrating T Cells Cytotoxic for Follicular Lymphoma Cells Can Be Expanded In Vitro," *Blood*, 89:3806–3816 (1997).

Danko, Istvan et al., "Direct gene transfer into muscle," *Vaccine*, 12:1499–1502 (1994).

Raz, Eyal et al., "Systemic immunological effects of cytokine genes injected into skeletal muscle," *Proc. Natl. Acad. Sci. U.S.A.*, 90:4523–4527 (1993).

Davis, Heather L. et al., "Direct Gene Transfer into Skeletal Muscle In Vivo: Factors Affecting Efficiency of Transfer and Stability of Expression," *Human Gene Therapy*, 4:151–159 (1993).

Sugaya, Susumu et al., "Inhibition of Tumor Growth by Direct Intratumoral Gene Transfer of Herpes Simplex Virus Thymidine Kinase Gene with DNA–Liposome Complexes," *Human Gene Therapy*, 7:223–230 (1996).

Prentice, Howard et al., "Ischemic/Reperfused Myocardium Can Express Recombinant Protein Following Direct DNA or Retroviral Injection," *J. Mol. Cell Cardiol.*, 28:133–140 (1996).

Soubrane, C. et al., "Direct Gene Transfer of a Plasmid Carrying the Herpes Simplex Virus–Thymidine Kinase Gene (HSV–TK) in Transplanted Murine Melanoma: In Vivo Study," *European Journal of Cancer*, 32A:691–695 (1996).

Kass–Eisler, Alyson et al., "Prospects for Gene Therapy with Direct Injection of Polynucleotides," *Ann. N. Y. Acad. Sci.*, 772:232–240 (1995).

DeMatteo, Ronald P. et al., "Gene Transfer to the Thymus," *Annals of Surgery*, 222:229–242 (1995).

Addison, Christina L. et al., "Intratumoral injection of an adenovirus expressing interleukin 2 induces regression and immunity in a murine breast cancer model," *Proc. Natl. Acad. Sci. U.S.A.*, 92:8522–8526 (1995).

Hengge, Ulrich R. et al., "Expression of Naked DNA in Human, Pig, and Mouse Skin," *Journal of Clinical Investigation*, 97:2911–2916 (1996).

Felgner, Philip L. et al., "Improved Cationic Lipid Formulations for In Vivo Gene Therapy," *Ann. N. Y. Acad. Sci.*, 772:126–139 (1995).

Furth, Priscilla A. et al., "Gene Transfer into Mammalian Cells by Jet Injection," *Hybridoma*, 14:149–152 (1995).

Vile, R.G. et al., "Targeting of cytokine gene expression to malignant melanoma cells using tissue specific promoter sequences," *Annals of Oncology*, 5 Suppl 4:S59–S65 (1994).

Yovandich, Jason et al., "Gene Transfer to Synovial Cells by Intra–Articular Administration of Plasmid DNA," *Human Gene Therapy*, 6:603–610 (1995).

Spessot, Robert, "Cloning of the Herpes Simplex Virus ICP4 Gene in an Adenovirus Vector: Effects on Adenovirus Gene Expression and Replication," *Virology*, 168:378–387 (1989).

Graham, Frank L. et al., "Manipulation of Adenovirus Vectors," *Methods in Molecular Biology*, vol. 7, Chapter 11, pp. 109–128 (1991).

Sambrook, J. et al., "Standard Protocol for Calcium Phosphate–mediated Transfection of Adherent Cells," *Molecular Cloning A Laboratory Manual*, 2d edition, Chapter 16:33–37 (1989).

Cantwell, Mark et al., "Acquired CD40–ligand deficiency in chronic lymphocytic leukemia," *Nature Medicine*, 3:984–989 (1997).

Kipps, Thomas J. et al., "New developments in flow cytometric analyses of lymphocyte markers," *Laboratory Immunology II*, 12:237–275 (1992).

Rassenti, Laura Z. et al., "Lack of Allelic Exclusion in B Cell Chronic Lymphocytic Leukemia," *J. Exp. Med.*, 185:1435–1445 (1992).

Ranheim, Eric A. et al., "Activated T Cells Induce Expression of B7/BB1 on Normal or Leukemic B Cells through a CD40–dependent Signal," *J. Exp. Med.*, 177:925–935 (1993).

Clark, Edward A. et al., "Activation of human B cells mediated through two distinct cell surface differentiation antigens, Bp35 and Bp50," *Proc. Natl. Acad. Sci. U.S.A.*, 83:4494–4498 (1986).

Banchereau, Jacques et al., "Long–Term Human B Cell Lines Dependent on Interleukin–4 and Antibody to CD40," *Science*, 251:70–72 (1991).

Blieden, Timothy M. et al., "Class–I MHC Expression in the Mouse Lung Carcinoma, Line 1: A Model for Class–I Inducible Tumors," *Int. J. Cancer Supp.*, 6:82–89 (1991).

Kouskoff, Valerie et al., "Organ–Specific Disease Provoked by Systemic Autoimmunity," *Cell*, 87:811–822 (1997).

Evan, Christopher et al., "Clinical Trial to Assess the Safety, Feasibility, and Efficacy of Transferring a Potentially Anti-Arthritic Cytokine Gene to Human Joints with Rheumatoid Arthritis," *Human Gene Therapy*, vol. 7, pp. 1261–1280 (1996).

Cantwell, M.H. et al., "CD95 and FAS–ligand expression and apoptosis in rheumatoid arthritis," Arthritis and Rheumatism, vol. 39, No. 9, Suppl., Sep. 1996 (1996–09), p. 287.

* cited by examiner

DOMAINS: I - Cytoplasmic Domain; II - Transmembrane Domain; III - Proximal Extracellular Domain; IV - Distal Extracellular Domain (putative soluble form)

```
  1 MQQPFNYPYPQIYWVDSSASSPWAPPGTVLPCPTSVPRRPGQRRPPPPP 50
    |||||||||||||||||||||||||||||||||||||||||||||||||
  1 MQQPFNYPYPQIYWVDSSASSPWAPPGTVLPCPTSVPRRPGQRRPPPPP 50

51 PPPLPPPPPPPPLPPLPLPPLKKRGNHSTGLCLLVMFFMVLVALVGLGLG 100
    |||||||||||||||||||||||||||||||||||||||||||||||||
 51 PPPLPPPPPPPPLPPLPLPPLKKRGNHSTGLCLLVMFFMVLVALVGLGLG 100

101 MFQLFHLQKELAELRESTSQMHTASSLEKQIGHPSPPPEKKELRKVAHLT 150
    ||||||||||||||| |.|  ..||:|||||||||||||||||||||||
101 MFQLFHLQKELAELREFTNQSLKVSSFEKQIGHPSPPPEKKELRKVAHLT 150

151 GKSNSRSMPLEWEDTYGIVLLSGVKYKKGGLVINETGLYFVYSKVYFRGQ 200
    |||||||||||||||||||||||||||||||||||||||||||||||||
151 GKSNSRSMPLEWEDTYGIVLLSGVKYKKGGLVINETGLYFVYSKVYFRGQ 200

201 SCNNLPLSHKVYMRNSKYPQDLVMMEGKMMSYCTTGQMWARSSYLGAVFN 250
    |||||||||||||||||||||||||||||||||||||||||||||||||
201 SCNNLPLSHKVYMRNSKYPQDLVMMEGKMMSYCTTGQMWARSSYLGAVFN 250

251 LTSADHLYVNVSELSLVNFEESQTFFGLYKL 281
    ||||||||||||||||||||||||||||||
251 LTSADHLYVNVSELSLVNFEESQTFFGLYKL 281
```

Figure 25

```
  1 MQQPFNYPYPQIYWVDSSASSPWAPPGTVLPCPTSVPRRPGQRRPPPPPP 50
    ||||||||||||||||||||||||||||||||||||||||||||||||||
  1 MQQPFNYPYPQIYWVDSSASSPWAPPGTVLPCPTSVPRRPGQRRPPPPPP 50

51 PPPLPPPPPPPPLPPLPLPPLKKRGNHSTGLCLLVMFFMVLVALVGLGLG 100
    ||||||||||||||||||||||||||||||||||||||||||||||||||
 51 PPPLPPPPPPPPLPPLPLPPLKKRGNHSTGLCLLVMFFMVLVALVGLGLG 100

101 MFQLFHLQKELAELRESTSQMHTASSLEKQIGHPSPPPEKKELRKVAHLT 150
    |||||:                      :...|||||||||||||||||
101 MFQLFR......................FAQAIGHPSPPPEKKELRKVAHLT 130

151 GKSNSRSMPLEWEDTYGIVLLSGVKYKKGGLVINETGLYFVYSKVYFRGQ 200
    ||||||||||||||||||||||||||||||||||||||||||||||||||
131 GKSNSRSMPLEWEDTYGIVLLSGVKYKKGGLVINETGLYFVYSKVYFRGQ 180

201 SCNNLPLSHKVYMRNSKYPQDLVMMEGKMMSYCTTGQMWARSSYLGAVFN 250
    ||||||||||||||||||||||||||||||||||||||||||||||||||
181 SCNNLPLSHKVYMRNSKYPQDLVMMEGKMMSYCTTGQMWARSSYLGAVFN 230

251 LTSADHLYVNVSELSLVNFEESQTFFGLYKL 281
    ||||||||||||||||||||||||||||||
231 LTSADHLYVNVSELSLVNFEESQTFFGLYKL 261
```

Figure 26

```
  1 MQQPFNYPYPQIYWVDSSASSPWAPPGTVLPCPTSVPRRPGQRRPPPPPP  50
    ||||||||||||||||||||||||||||||||||||||||||||||||||
  1 MQQPFNYPYPQIYWVDSSASSPWAPPGTVLPCPTSVPRRPGQRRPPPPPP  50

51 PPPLPPPPPPPPLPPLPLPPLKKRGNHSTGLCLLVMFFMVLVALVGLGLG 100
    |||||||||||||||||||||||||||||||||||||||||||||||||
 51 PPPLPPPPPPPPLPPLPLPPLKKRGNHSTGLCLLVMFFMVLVALVGLGLG 100

101 MFQLFHLQKELAELRESTSQMHTASSLEKQQIGHPSPPPEKKELRKVAHLT 150
    |||||     ::|   .:-|  .: : :   -|||||||||||||||||||
101 MFQLF.....MPEEGSGCSVRRRPYGCVLRIGHPSPPPEKKELRKVAHLT 145

151 GKSNSRSMPLEWEDTYGIVLLSGVKYKKGGLVINETGLYFVYSKVYFRGQ 200
    ||||||||||||||||||||||||||||||||||||||||||||||||||
146 GKSNSRSMPLEWEDTYGIVLLSGVKYKKGGLVINETGLYFVYSKVYFRGQ 195

201 SCNNLPLSHKVYMRNSKYPQDLVMMEGKMMSYCTTGQMWARSSYLGAVFN 250
    ||||||||||||||||||||||||||||||||||||||||||||||||||
196 SCNNLPLSHKVYMRNSKYPQDLVMMEGKMMSYCTTGQMWARSSYLGAVFN 245

251 LTSADHLYVNVSELSLVNFEESQTFFGLYKL 281
    ||||||||||||||||||||||||||||||
246 LTSADHLYVNVSELSLVNFEESQTFFGLYKL 276
```

Figure 27

Matrix Metalloproteinase Cleavage Sites

Cleavage ⇒ (between $P_1$ and $P'_1$)

Collagenases

MMP-1    Interstitial Collagenase

| $P_4$ | $P_3$ | $P_2$ | $P_1$ | $P'_1$ | $P'_2$ | $P'_3$ | $P'_4$ |
|---|---|---|---|---|---|---|---|
| Ala | Pro | Leu | Gly | Met | Arg | Met/Ala | Arg |
| Gly/Leu | Leu | Met/Tyr | His | Leu | Leu | Gly | Lys |
| Met | Ala | Val/Gly | Glu | Ile | Phe | Val | Gln |
| Glu | Asp | Ile | Tyr | Gln | Trp | Ser | Ile |
| Pro | Ser | Gln/Arg | Ala | Pro | Glu | Glu | Gly |
| Tyr | Glu | Asp | Phe | Phe | Ala | Phe | Ser |
| Ile | Gly | Glu | Gln | Ala | Val/Gly | Arg | Glu |
| Thr | Arg | Ala | Asn | Tyr/Val | Ser | Pro | Ala |
| Arg |  |  |  | [not K,E,W] | Asn |  |  |

MMP-8    Neutrophil Collagenase

| $P_4$ | $P_3$ | $P_2$ | $P_1$ | $P'_1$ | $P'_2$ | $P'_3$ | $P'_4$ |
|---|---|---|---|---|---|---|---|
| Ala | Pro | Leu | Glu | Tyr | Ala | Gly | Arg |
| Gly/Leu | Leu | Gln | Gly/His | Ile | Leu | Met | Gln |
| Met |  |  | Ala | Leu | Trp | Ala |  |
| Glu |  |  |  | Val |  |  |  |
| Pro |  |  |  | Phe |  |  |  |
| Tyr/Ile/Thr/Arg |  |  | Ala |  |  |  |  |
| (otherwise same as MMP-1) |  |  |  |  |  |  |  |

Figure 28A

Gelatinases

MMP-2 Gelatinase A

| $P_4$ | $P_3$ | $P_2$ | $P_1$ | $P'_1$ | $P'_2$ | $P'_3$ | $P'_4$ |
|---|---|---|---|---|---|---|---|
| Gly | Pro | Arg | Gly | Leu | Ala/Leu | Gly/Ala | Gln |
| Ile | Ala | Gln | Asn | Ile/Phe | Phe/Trp | Leu | Arg |
| Pro | Arg | Leu | Ala | Val/Met | Gly | Ser | His |
| Arg | | Ala | His | Ala | Arg/Gln | Pro | Pro |
| Leu | | Lys | Leu | Glu | His | | |
| | | Ile | Tyr | Gln/Asn | Val | | |
| | | His | | Ser | | | |

MMP-9 Gelatinase B

| $P_4$ | $P_3$ | $P_2$ | $P_1$ | $P'_1$ | $P'_2$ | $P'_3$ | $P'_4$ |
|---|---|---|---|---|---|---|---|
| Gln/Arg | Pro | Arg | Gly | Leu | Glu | Ala | Thr |
| | | Gln | | Ile/Phe | Ala/Leu/Phe | Leu | |
| | | Leu | | Val/Met | Trp/Gly | Ser | |
| | | | | Ala | | Gly | |

Stromelysins

MMP-3 Stromelysin 1

| $P_4$ | $P_3$ | $P_2$ | $P_1$ | $P'_1$ | $P'_2$ | $P'_3$ | $P'_4$ |
|---|---|---|---|---|---|---|---|
| Asp | Pro | Phe | Glu | Leu | Arg | Ala | Thr |
| Gly | Ala | Leu/Met | Ala | Phe | Leu/Phe | Arg/Met | |
| Gln/Arg | | | | | | | |
| Leu | Val | Tyr | Gln/Phe | Trp/Tyr | Trp | Gly | Pro |
| Ile | Leu | Pro/Gly/Glu | Asn | Ile | Val | Val/Ile | |
| Glu/Val | | | | | | | |
| Leu | Thr | Ile | His | Val | Gln | Ser/Asn | Ala |
| Lys | Phe | Ala | Gly | Met | His/Met | Glu/Thr | |
| Gly/Asp | | | | | | | |
| Arg | Arg | Ser | Leu/Pro | Glu | Glu/Ser/Thr | Leu | |
| Ser/Lys/Phe | Ser/Gly | | Lys/Tyr/Arg | | | | |
| Pro/Met | | | | | | | |
| Ala/Phe/Gln | | | | | | | |

Figure 28B

| | $P_4$ | $P_3$ | $P_2$ | $P_1$ | $P'_1$ | $P'_2$ | $P'_3$ | $P'_4$ |
|---|---|---|---|---|---|---|---|---|
| MMP-10 | Arg | Stromelysin 2 Ala | Ile | His | Ile | Gln | Ala | Glu |
| | Gly | Pro | His | Leu | Leu | Val | Glu | Ala |
| Others | | Matrilysin | | | | | | |
| MMP-7 | Ile | Pro | Leu | Glu | Leu | Arg | Ala | Gln |
| | Gly | Leu | Gln | Met/Ala | Ile | Met | Val/Arg/Met | |
| | Pro | | Val | Pro/Gln | Met | Gln | Gly | |
| | | | | Gly | | | | |

Figure 28C

SEQUENCE LISTING (1) GENERAL INFORMATION:

(iii) NUMBER OF SEQUENCES:    44

(2) INFORMATION FOR SEQ ID NO: 1:

(i) SEQUENCE CHARACTERISTICS:
        (A) LENGTH:          786 base pairs
        (B) TYPE:            nucleic acid
        (C) STRANDEDNESS:    single
        (D) TOPOLOGY:        linear (xi) SEQUENCE DESCRIPTION: SEQ ID NO: 1:

```
ATGATCGAAA CATACAACCA AACTTCTCCC CGATCTGCGG CCACTGGACT GCCCATCAGC      60

ATGAAAATTT TTATGTATTT ACTTACTGTT TTTCTTATCA CCCAGATGAT TGGGTCAGCA     120

CTTTTTGCTG TGTATCTTCA TAGAAGGTTG GACAAGATAG AAGATGAAAG GAATCTTCAT     180

GAAGATTTTG TATTCATGAA AACGATACAG AGATGCAACA CAGGAGAAAG ATCCTTATCC     240

TTACTGAACT GTGAGGAGAT TAAAAGCCAG TTTGAAGGCT TTGTGAAGGA TATAATGTTA     300

AACAAAGAGG AGACGAAGAA AGAAAACAGC TTTGAAATGC AAAAAGGTGA TCAGAATCCT     360

CAAATTGCGG CACATGTCAT AAGTGAGGCC AGCAGTAAAA CAACATCTGT GTTACAGTGG     420

GCTGAAAAAG GATACTACAC CATGAGCAAC AACTTGGTAA CCCTGGAAAA TGGGAAACAG     480

CTGACCGTTA AAAGACAAGG ACTCTATTAT ATCTATGCCC AAGTCACCTT CTGTTCCAAT     540

CGGGAAGCTT CGAGTCAAGC TCCATTTATA GCCAGCCTCT GCCTAAAGTC CCCCGGTAGA     600

TTCGAGAGAA TCTTACTCAG AGCTGCAAAT ACCCACAGTT CCGCCAAACC TTGCGGGCAA     660

CAATCCATTC ACTTGGGAGG AGTATTTGAA TTGCAACCAG GTGCTTCGGT GTTTGTCAAT     720

GTGACTGATC CAAGCCAAGT GAGCCATGGC ACTGGCTTCA CGTCCTTTGG CTTACTCAAA     780

CTCTGA                                                               786
```

(2) INFORMATION FOR SEQ ID NO: 2:

(i) SEQUENCE CHARACTERISTICS:
        (A) LENGTH:          783 base pairs
        (B) TYPE:            nucleic acid
        (C) STRANDEDNESS:    single
        (D) TOPOLOGY:        linear (xi) SEQUENCE DESCRIPTION: SEQ ID NO: 2:

```
ATGATAGAAA CATACAGCCA ACCTTCCCCC AGATCCGTGG CAACTGGACT TCCAGCGAGC      60

ATGAAGATTT TTATGTATTT ACTTACTGTT TTCCTTATCA CCCAAATGAT TGGATCTGTG     120

CTTTTTGCTG TGTATCTTCA TAGAAGATTG GATAAGGTCG AAGAGGAAGT AAACCTTCAT     180

GAAGATTTTG TATTCATAAA AAAGCTAAAG AGATGCAACA AAGGAGAAGG ATCTTTATCC     240
```

| | |
|---|---|
| TTGCTGAACT GTGAGGAGAT GAGAAGGCAA TTTGAAGACC TTGTCAAGGA TATAACGTTA | 300 |
| AACAAAGAAG AGAAAAAAGA AAACAGCTTT GAAATGCAAA GAGGTGATGA GGATCCTCAA | 360 |
| ATTGCAGCAC ACGTTGTAAG CGAAGCCAAC AGTAATGCAG CATCCGTTCT ACAGTGGGCC | 420 |
| AAGAAAGGAT ATTATACCAT GAAAAGCAAC TTGGTAATGC TTGAAAATGG GAAACAGCTG | 480 |
| ACGGTTAAAA GAGAAGGACT CTATTATGTC TACACTCAAG TCACCTTCTG CTCTAATCGG | 540 |
| GAGCCTTCGA GTCAACGCCC ATTCATCGTC GGCCTCTGGC TGAAGCCCAG CATTGGATCT | 600 |
| GAGAGAATCT TACTCAAGGC GGCAAATACC CACAGTTCCT CCCAGCTTTG CGAGCAGCAG | 660 |
| TCTGTTCACT TGGGCGGAGT GTTTGAATTA CAAGCTGGTG CTTCTGTGTT TGTCAACGTG | 720 |
| ACTGAAGCAA GCCAAGTGAT CCACAGAGTT GGCTTCTCAT CTTTTGGCTT ACTCAAACTC | 780 |
| TGA | 783 |

(2) INFORMATION FOR SEQ ID NO: 3:

(i) SEQUENCE CHARACTERISTICS:
        (A) LENGTH: 783 base pairs
        (B) TYPE: nucleic acid
        (C) STRANDEDNESS: single
        (D) TOPOLOGY: linear (xi) SEQUENCE DESCRIPTION: SEQ ID NO: 3:

| | |
|---|---|
| ATGATCGAAA CATACAACCA AACTTCTCCC CGATCTGCGG CCACTGGACT GCCCATCAGC | 60 |
| ATGAAAATTT TTATGTATTT ACTTACTGTT TTTCTTATCA CCCAGATGAT TGGGTCAGCA | 120 |
| CTTTTTGCTG TGTATCTTCA TAGAAGATTG GATAAGGTCG AAGAGGAAGT AAACCTTCAT | 180 |
| GAAGATTTTG TATTCATAAA AAAGCTAAAG AGATGCAACA AAGGAGAAGG ATCTTTATCC | 240 |
| TTGCTGAACT GTGAGGAGAT GAGAAGGCAA TTTGAAGACC TTGTCAAGGA TATAACGTTA | 300 |
| AACAAAGAAG AGAAAAAAGA AAACAGCTTT GAAATGCAAA GAGGTGATGA GGATCCTCAA | 360 |
| ATTGCAGCAC ACGTTGTAAG CGAAGCCAAC AGTAATGCAG CATCCGTTCT ACAGTGGGCC | 420 |
| AAGAAAGGAT ATTATACCAT GAAAAGCAAC TTGGTAATGC TTGAAAATGG GAAACAGCTG | 480 |
| ACGGTTAAAA GAGAAGGACT CTATTATGTC TACACTCAAG TCACCTTCTG CTCTAATCGG | 540 |
| GAGCCTTCGA GTCAACGCCC ATTCATCGTC GGCCTCTGGC TGAAGCCCAG CATTGGATCT | 600 |
| GAGAGAATCT TACTCAAGGC GGCAAATACC CACAGTTCCT CCCAGCTTTG CGAGCAGCAG | 660 |
| TCTGTTCACT TGGGCGGAGT GTTTGAATTA CAAGCTGGTG CTTCTGTGTT TGTCAACGTG | 720 |
| ACTGAAGCAA GCCAAGTGAT CCACAGAGTT GGCTTCTCAT CTTTTGGCTT ACTCAAACTC | 780 |
| TGA | 783 |

(2) INFORMATION FOR SEQ ID NO: 4:

(i) SEQUENCE CHARACTERISTICS:
        (A) LENGTH: 786 base pairs
        (B) TYPE: nucleic acid
        (C) STRANDEDNESS: single
        (D) TOPOLOGY: linear (xi) SEQUENCE DESCRIPTION: SEQ ID NO: 4:

| | |
|---|---|
| ATGATCGAAA CATACAACCA AACTTCTCCC CGATCTGCGG CCACTGGACT GCCCATCAGC | 60 |
| ATGAAAATTT TTATGTATTT ACTTACTGTT TTCCTTATCA CCCAAATGAT TGGATCTGTG | 120 |
| CTTTTTGCTG TGTATCTTCA TAGAAGGTTG GACAAGATAG AAGATGAAAG GAATCTTCAT | 180 |
| GAAGATTTTG TATTCATGAA AACGATACAG AGATGCAACA CAGGAGAAAG ATCCTTATCC | 240 |
| TTACTGAACT GTGAGGAGAT TAAAAGCCAG TTTGAAGGCT TGTGAAGGA TATAATGTTA | 300 |

```
AACAAAGAGG AGACGAAGAA AGAAAACAGC TTTGAAATGC AAAAAGGTGA TCAGAATCCT      360

CAAATTGCGG CACATGTCAT AAGTGAGGCC AGCAGTAAAA CAACATCTGT GTTACAGTGG      420

GCTGAAAAAG GATACTACAC CATGAGCAAC AACTTGGTAA CCCTGGAAAA TGGGAAACAG      480

CTGACCGTTA AAAGACAAGG ACTCTATTAT ATCTATGCCC AAGTCACCTT CTGTTCCAAT      540

CGGGAAGCTT CGAGTCAAGC TCCATTTATA GCCAGCCTCT GCCTAAAGTC CCCCGGTAGA      600

TTCGAGAGAA TCTTACTCAG AGCTGCAAAT ACCCACAGTT CCGCCAAACC TTGCGGGCAA      660

CAATCCATTC ACTTGGGAGG AGTATTTGAA TTGCAACCAG GTGCTTCGGT GTTTGTCAAT      720

GTGACTGATC CAAGCCAAGT GAGCCATGGC ACTGGCTTCA CGTCCTTTGG CTTACTCAAA      780

CTCTGA                                                                786

(2) INFORMATION FOR SEQ ID NO: 5:

(i) SEQUENCE CHARACTERISTICS:
         (A) LENGTH:       783 base pairs
         (B) TYPE:         nucleic acid
         (C) STRANDEDNESS: single
         (D) TOPOLOGY:     linear (xi) SEQUENCE DESCRIPTION: SEQ ID NO: 5:

ATGATCGAAA CATACAACCA AACTTCTCCC CGATCTGCGG CCACTGGACT GCCCATCAGC       60

ATGAAAATTT TTATGTATTT ACTTACTGTT TTCCTTATCA CCCAAATGAT TGGATCTGTG      120

CTTTTTGCTG TGTATCTTCA TAGAAGATTG GATAAGGTCG AAGAGGAAGT AAACCTTCAT      180

GAAGATTTTG TATTCATAAA AAAGCTAAAG AGATGCAACA AAGGAGAAGG ATCTTTATCC      240

TTGCTGAACT GTGAGGAGAT GAGAAGGCAA TTTGAAGACC TTGTCAAGGA TATAACGTTA      300

AACAAAGAAG AGAAAAAAGA AAACAGCTTT GAAATGCAAA GAGGTGATGA GGATCCTCAA      360

ATTGCAGCAC ACGTTGTAAG CGAAGCCAAC AGTAATGCAG CATCCGTTCT ACAGTGGGCC      420

AAGAAAGGAT ATTATACCAT GAAAAGCAAC TTGGTAATGC TTGAAAATGG GAAACAGCTG      480

ACGGTTAAAA GAGAAGGACT CTATTATGTC TACACTCAAG TCACCTTCTG CTCTAATCGG      540

GAGCCTTCGA GTCAACGCCC ATTCATCGTC GGCCTCTGGC TGAAGCCCAG CATTGGATCT      600

GAGAGAATCT TACTCAAGGC GGCAAATACC ACAGTTCCT CCCAGCTTTG CGAGCAGCAG       660

TCTGTTCACT TGGGCGGAGT GTTTGAATTA CAAGCTGGTG CTTCTGTGTT TGTCAACGTG      720

ACTGAAGCAA GCCAAGTGAT CCACAGAGTT GGCTTCTCAT CTTTTGGCTT ACTCAAACTC      780

TGA                                                                   783

(2) INFORMATION FOR SEQ ID NO: 6:

(i) SEQUENCE CHARACTERISTICS:
         (A) LENGTH:       786 base pairs
         (B) TYPE:         nucleic acid
         (C) STRANDEDNESS: single
         (D) TOPOLOGY:     linear (xi) SEQUENCE DESCRIPTION: SEQ ID NO: 6:

ATGATAGAAA CATACAGCCA ACCTTCCCCC AGATCCGTGG CAACTGGACT TCCAGCGAGC       60

ATGAAGATTT TTATGTATTT ACTTACTGTT TTTCTTATCA CCCAGATGAT TGGGTCAGCA      120

CTTTTTGCTG TGTATCTTCA TAGAAGGTTG GACAAGATAG AAGATGAAAG GAATCTTCAT      180

GAAGATTTTG TATTCATGAA AACGATACAG AGATGCAACA CAGGAGAAAG ATCCTTATCC      240

TTACTGAACT GTGAGGAGAT TAAAAGCCAG TTTGAAGGCT TGTGAAGGA TATAATGTTA       300
```

```
AACAAAGAGG AGACGAAGAA AGAAAACAGC TTTGAAATGC AAAAAGGTGA TCAGAATCCT      360

CAAATTGCGG CACATGTCAT AAGTGAGGCC AGCAGTAAAA CAACATCTGT GTTACAGTGG      420

GCTGAAAAAG GATACTACAC CATGAGCAAC AACTTGGTAA CCCTGGAAAA TGGGAAACAG      480

CTGACCGTTA AAAGACAAGG ACTCTATTAT ATCTATGCCC AAGTCACCTT CTGTTCCAAT      540

CGGGAAGCTT CGAGTCAAGC TCCATTTATA GCCAGCCTCT GCCTAAAGTC CCCCGGTAGA      600

TTCGAGAGAA TCTTACTCAG AGCTGCAAAT ACCCACAGTT CCGCCAAACC TTGCGGGCAA      660

CAATCCATTC ACTTGGGAGG AGTATTTGAA TTGCAACCAG GTGCTTCGGT GTTTGTCAAT      720

GTGACTGATC CAAGCCAAGT GAGCCATGGC ACTGGCTTCA CGTCCTTTGG CTTACTCAAA      780

CTCTGA                                                                786
```

(2) INFORMATION FOR SEQ ID NO: 7:

(i) SEQUENCE CHARACTERISTICS:
        (A) LENGTH:      786 base pairs
        (B) TYPE:        nucleic acid
        (C) STRANDEDNESS: single
        (D) TOPOLOGY:    linear (xi) SEQUENCE DESCRIPTION: SEQ ID NO: 7:

```
ATGATAGAAA CATACAGCCA ACCTTCCCCC AGATCCGTGG CAACTGGACT TCCAGCGAGC      60

ATGAAGATTT TTATGTATTT ACTTACTGTT TTCCTTATCA CCCAAATGAT TGGATCTGTG      120

CTTTTTGCTG TGTATCTTCA TAGAAGGTTG GACAAGATAG AAGATGAAAG GAATCTTCAT      180

GAAGATTTTG TATTCATGAA AACGATACAG AGATGCAACA CAGGAGAAAG ATCCTTATCC      240

TTACTGAACT GTGAGGAGAT TAAAAGCCAG TTTGAAGGCT TTGTGAAGGA TATAATGTTA      300

AACAAAGAGG AGACGAAGAA AGAAAACAGC TTTGAAATGC AAAAAGGTGA TCAGAATCCT      360

CAAATTGCGG CACATGTCAT AAGTGAGGCC AGCAGTAAAA CAACATCTGT GTTACAGTGG      420

GCTGAAAAAG GATACTACAC CATGAGCAAC AACTTGGTAA CCCTGGAAAA TGGGAAACAG      480

CTGACCGTTA AAAGACAAGG ACTCTATTAT ATCTATGCCC AAGTCACCTT CTGTTCCAAT      540

CGGGAAGCTT CGAGTCAAGC TCCATTTATA GCCAGCCTCT GCCTAAAGTC CCCCGGTAGA      600

TTCGAGAGAA TCTTACTCAG AGCTGCAAAT ACCCACAGTT CCGCCAAACC TTGCGGGCAA      660

CAATCCATTC ACTTGGGAGG AGTATTTGAA TTGCAACCAG GTGCTTCGGT GTTTGTCAAT      720

GTGACTGATC CAAGCCAAGT GAGCCATGGC ACTGGCTTCA CGTCCTTTGG CTTACTCAAA      780

CTCTGA                                                                786
```

(2) INFORMATION FOR SEQ ID NO: 8:

(i) SEQUENCE CHARACTERISTICS:
        (A) LENGTH:      864 base pairs
        (B) TYPE:        nucleic acid
        (C) STRANDEDNESS: single
        (D) TOPOLOGY:    linear (xi) SEQUENCE DESCRIPTION: SEQ ID NO: 8:

```
AACTCTAACG CAGCATGATC GAAACATACA GTCAACCTTC TCCCCGCTCC GTGGCCACTG      60

GACCACCTGT CAGTATGAAA ATTTTTATGT ATTTACTTAC AGTTTTTCTT ATCACCCAGA      120

TGATTGGGTC AGCGCTTTTT GCTGTGTATC TTCACAGACG ATTGGACAAG ATAGAAGACG      180

AAAGGAATCT TCATGAAGAT TTTGTGTTCA TGAAAACGAT ACAGAGATGC AATAAAGGAG      240

AGGGGTCCTT ATCCTTACTG AACTGTGAGG AAATTAGAAG CCGGTTTGAA GACTTGGTCA      300

AGGATATAAT GCAAAACAAA GAAGTAAAGA AGAAAGAAAA AAACTTTGAA ATGCACAAGG      360
```

```
GTGATCAGGA GCCTCAGATA GCGGCACATG TCATCAGTGA GGCCAGTAGT AAAACAACCT    420

CTGTTCTCCA GTGGGCCCCC AAAGGATACT ACACCCTAAG CAACAACCTG GTAACCCTCG    480

AAAACGGGAA ACAGCTGGCC GTGAAAAGAC AAGGATTCTA TTACATCTAC ACCCAAGTCA    540

CCTTCTGTTC CAATCGGGAA ACTTTGAGTC AAGCTCCATT TATAGCCAGC CTCTGCCTGA    600

AGTCCCCAAG TGGATCAGAG AGAATCTTAC TGAGAGCTGC AAACACCCAC AGTTCTTCCA    660

AACCATGCGG GCAGCAATCC ATTCACTTAG GAGGAGTCTT TGAATTGCAA TCGGGTGCTT    720

CGGTGTTTGT CAATGTGACT GATCCAAGTC AAGTGAGCCA CGGGACGGGC TTCACATCAT    780

TTGGCTTACT CAAACTCTGA ACGGTGTAAG CCAGCAGGCT GCGGCTGGGC TGATGCTGGT    840

GGTCTTCACA ATCCAGGAAA GCAG                                          864

(2) INFORMATION FOR SEQ ID NO:  9:

(i) SEQUENCE CHARACTERISTICS:
        (A) LENGTH:      3634 base pairs
        (B) TYPE:        nucleic acid
        (C) STRANDEDNESS: single
        (D) TOPOLOGY:    linear (xi) SEQUENCE DESCRIPTION: SEQ ID NO:  9:

GAATTCCGGG TGATTTCACT CCCGGCTGTC CAGGCTTGTC CTGCTACCCC ACCCAGCCTT     60

TCCTGAGGCC TCAAGCCTGC CACCAAGCCC CCAGCTCCTT CTCCCCGCAG GACCCAAACA    120

CAGGCCTCAG GACTCAACAC AGCTTTTCCC TCCAACCCGT TTTCTCTCCC TCAACGGACT    180

CAGCTTTCTG AAGCCCCTCC CAGTTCTAGT TCTATCTTTT TCCTGCATCC TGTCTGGAAG    240

TTAGAAGGAA ACAGACCACA GACCTGGTCC CCAAAAGAAA TGGAGGCAAT AGGTTTTGAG    300

GGGCATGGGG ACGGGGTTCA GCCTCCAGGG TCCTACACAC AAATCAGTCA GTGGCCCAGA    360

AGACCCCCCT CGGAATCGGA GCAGGGAGGA TGGGGAGTGT GAGGGGTATC CTTGATGCTT    420

GTGTGTCCCC AACTTTCCAA ATCCCCGCCC CCGCGATGGA GAAGAAACCG AGACAGAAGG    480

TGCAGGGCCC ACTACCGCTT CCTCCAGATG AGCTCATGGG TTTCTCCACC AAGGAAGTTT    540

TCCGCTGGTT GAATGATTCT TTCCCCGCCC TCCTCTCGCC CCAGGGACAT ATAAAGGCAG    600

TTGTTGGCAC ACCCAGCCAG CAGACGCTCC CTCAGCAAGG ACAGCAGAGG ACCAGCTAAG    660

AGGGAGAGAA GCAACTACAG ACCCCCCCTG AAAACAACCC TCAGACGCCA CATCCCCTGA    720

CAAGCTGCCA GGCAGGTTCT CTTCCTCTCA CATACTGACC CACGGCTTCA CCCTCTCTCC    780

CCTGGAAAGG ACACCATGAG CACTGAAAGC ATGATCCGGG ACGTGGAGCT GGCCGAGGAG    840

GCGCTCCCCA AGAAGACAGG GGGGCCCCAG GGCTCCAGGC GGTGCTTGTT CCTCAGCCTC    900

TTCTCCTTCC TGATCGTGGC AGGCGCCACC ACGCTCTTCT GCCTGCTGCA CTTTGGAGTG    960

ATCGGCCCCC AGAGGGAAGA GGTGAGTGCC TGGCCAGCCT TCATCCACTC TCCCACCCAA   1020

GGGGAAATGA GAGACGCAAG AGAGGGAGAG AGATGGGATG GGTGAAAGAT GTGCGCTGAT   1080

AGGGAGGGAT GAGAGAGAAA AAAACATGGA GAAAGACGGG GATGCAGAAA GAGATGTGGC   1140

AAGAGATGGG GAAGAGAGAG AGAGAAAGAT GGAGAGACAG GATGTCTGGC ACATGGAAGG   1200

TGCTCACTAA GTGTGTATGG AGTGAATGAA TGAATGAATG AATGAACAAG CAGATATATA   1260

AATAAGATAT GGAGACAGAT GTGGGTGTG AGAAGAGAGA TGGGGAAGA AACAAGTGAT     1320

ATGAATAAAG ATGGTGAGAC AGAAAGAGCG GGAAATATGA CAGCTAAGGA GAGAGATGGG   1380

GGAGATAAGG AGAGAAGAAG ATAGGGTGTC TGGCACACAG AAGACACTCA GGGAAAGAGC   1440

TGTTGAATGC TGGAAGGTGA ATACACAGAT GAATGGAGAG AGAAAACCAG ACACCTCAGG   1500
```

```
GCTAAGAGCG CAGGCCAGAC AGGCAGCCAG CTGTTCCTCC TTTAAGGGTG ACTCCCTCGA    1560

TGTTAACCAT TCTCCTTCTC CCCAACAGTT CCCCAGGGAC CTCTCTCTAA TCAGCCCTCT    1620

GGCCCAGGCA GTCAGTAAGT GTCTCCAAAC CTCTTTCCTA ATTCTGGGTT TGGGTTTGGG    1680

GGTAGGGTTA GTACCGGTAT GGAAGCAGTG GGGGAAATTT AAAGTTTTGG TCTTGGGGGA    1740

GGATGGATGG AGGTGAAAGT AGGGGGGTAT TTTCTAGGAA GTTTAAGGGT CTCAGCTTTT    1800

TCTTTTCTCT CTCCTCTTCA GGATCATCTT CTCGAACCCC GAGTGACAAG CCTGTAGCCC    1860

ATGTTGTAGG TAAGAGCTCT GAGGATGTGT CTTGGAACTT GGAGGGCTAG GATTTGGGGA    1920

TTGAAGCCCG GCTGATGGTA GGCAGAACTT GGAGACAATG TGAGAAGGAC TCGCTGAGCT    1980

CAAGGGAAGG GTGGAGGAAC AGCACAGGCC TTAGTGGGAT ACTCAGAACG TCATGGCCAG    2040

GTGGGATGTG GGATGACAGA CAGAGAGGAC AGGAACCGGA TGTGGGGTGG GCAGAGCTCG    2100

AGGGCCAGGA TGTGGAGAGT GAACCGACAT GGCCACACTG ACTCTCCTCT CCCTCTCTCC    2160

CTCCCTCCAG CAAACCCTCA AGCTGAGGGG CAGCTCCAGT GGCTGAACCG CCGGGCCAAT    2220

GCCCTCCTGG CCAATGGCGT GGAGCTGAGA GATAACCAGC TGGTGGTGCC ATCAGAGGGC    2280

CTGTACCTCA TCTACTCCCA GGTCCTCTTC AAGGGCCAAG GCTGCCCCTC CACCCATGTG    2340

CTCCTCACCC ACACCATCAG CCGCATCGCC GTCTCCTACC AGACCAAGGT CAACCTCCTC    2400

TCTGCCATCA AGAGCCCCTG CCAGAGGGAG ACCCCAGAGG GGGCTGAGGC CAAGCCCTGG    2460

TATGAGCCCA TCTATCTGGG AGGGGTCTTC CAGCTGGAGA AGGGTGACCG ACTCAGCGCT    2520

GAGATCAATC GGCCCGACTA TCTCGACTTT GCCGAGTCTG GCCAGGTCTA CTTTGGGATC    2580

ATTGCCCTGT GAGGAGGACG AACATCCAAC CTTCCCAAAC GCCTCCCCTG CCCCAATCCC    2640

TTTATTACCC CCTCCTTCAG ACACCCTCAA CCTCTTCTGG CTCAAAAAGA GAATTGGGGG    2700

CTTAGGGTCG GAACCCAAGC TTAGAACTTT AAGCAACAAG ACCACCACTT CGAAACCTGG    2760

GATTCAGGAA TGTGTGGCCT GCACAGTGAA GTGCTGGCAA CCACTAAGAA TTCAAACTGG    2820

GGCCTCCAGA ACTCACTGGG GCCTACAGCT TTGATCCCTG ACATCTGGAA TCTGGAGACC    2880

AGGGAGCCTT TGGTTCTGGC CAGAATGCTG CAGGACTTGA GAAGACCTCA CCTAGAAATT    2940

GACACAAGTG GACCTTAGGC CTTCCTCTCT CCAGATGTTT CCAGACTTCC TTGAGACACG    3000

GAGCCCAGCC CTCCCCATGG AGCCAGCTCC CTCTATTTAT GTTTGCACTT GTGATTATTT    3060

ATTATTTATT TATTATTTAT TTATTTACAG ATGAATGTAT TTATTTGGGA GACCGGGTA    3120

TCCTGGGGGA CCCAATGTAG GAGCTGCCTT GGCTCAGACA TGTTTTCCGT GAAAACGGAG    3180

CTGAACAATA GGCTGTTCCC ATGTAGCCCC CTGGCCTCTG TGCCTTCTTT TGATTATGTT    3240

TTTTAAAATA TTTATCTGAT TAAGTTGTCT AAACAATGCT GATTTGGTGA CCAACTGTCA    3300

CTCATTGCTG AGCCTCTGCT CCCCAGGGGA GTTGTGTCTG TAATCGCCCT ACTATTCAGT    3360

GGCGAGAAAT AAAGTTTGCT TAGAAAAGAA ACATGGTCTC CTTCTTGGAA TTAATTCTGC    3420

ATCTGCCTCT TCTTGTGGGT GGGAAGAAGC TCCCTAAGTC CTCTCTCCAC AGGCTTTAAG    3480

ATCCCTCGGA CCCAGTCCCA TCCTTAGACT CCTAGGGCCC TGGAGACCCT ACATAAACAA    3540

AGCCCAACAG AATATTCCCC ATCCCCCAGG AAACAAGAGC CTGAACCTAA TTACCTCTCC    3600

CTCAGGGCAT GGGAATTTCC AACTCTGGGA ATTC                              3634
```

(2) INFORMATION FOR SEQ ID NO: 10:

(i) SEQUENCE CHARACTERISTICS:
        (A) LENGTH:     1997 base pairs
        (B) TYPE:       nucleic acid (C) STRANDEDNESS: single
        (D) TOPOLOGY:     linear (xi) SEQUENCE DESCRIPTION: SEQ ID NO: 10:

```
GAGACAGAGT CTTGCTCTGT CCCCCAGGCT GGAATACAGT GGTGCGATCT TGACTCACTG      60
CAGCCTCCGC CTCCCAGGTT CAAATAATTC TCCAGCCTCA GCCTCCCGAG TAGCTGGGAC     120
TGCAGATGCG CACCAGCACG CCTGGCTAAT TTTTGTATTT ATTATAGAGA TGGGGTTTCA     180
CCATGTTGGC CAGCTGGTCT CAAACTCCTG ACCTCAAGTA ATCCGCCCAC CTCAGACTCC     240
CAAAGTGCCA GGATTACAGG TGTGAGCCAC TGCACCAGGC CTGGAACAAT TTTAAAATAA     300
TGTATTGGCT CTGCAAATGC AGCTTCAGAA CAAGTCCCTT AGCTGTCCCC ACCCCACCCT     360
AAGTCACCAC CCTTAAGCCT CACCCATGTG GAATTCTGAA ACTTCCTTTG TAGAAAACTT     420
TGGAAGGTGT CTGCCACATT GATCCTGGAA TGTGTGTTTA TTTGGGGTTA TATAAATCTG     480
TTCTGTGGAA GCCACCTGAA GTCAGGAAGA GATGGAGGGC ATCCTTCAGG AGTGAGATGA     540
GACCTCATCA TACTTGACTG TCCAGCATCA TCTCTGAGTA AGGGGACCAA AAAATTTATC     600
TTCCAAACTA GGACACTTTC AAGAGTGGAA GGGGGATCCA TTAATATTTT CACCTGGACA     660
AGAGGCAAAC ACCAGAATGT CCCCGATGAA GGGGATATAT AATGGACCTT CTTGATGTGA     720
AACCTGCCAG ATGGGCTGGA AAGTCCGTAT ACTGGGACAA GTATGATTTG AGTTGTTTGG     780
GACAAGGACA GGGGTACAAG AGAAGGAAAT GGGCAAAGAG AGAAGCCTGT ACTCAGCCAA     840
GGGTGCAGAG ATGTTATATA TGATTGCTCT TCAGGGAACC GGGCCTCCAG CTCACACCCC     900
AGCTGCTCAA CCACCTCCTC TCTGAATTGA CTGTCCCTTC TTTGGAACTC TAGGCCTGAC     960
CCCACTCCCT GGCCCTCCCA GCCCACGATT CCCCTGACCC GACTCCCTTT CCAGAACTC    1020
AGTCGCCTGA ACCCCAGCC TGTGGTTCTC TCCTAGGCCT CAGCCTTTCC TGCCTTTGAC    1080
TGAAACAGCA GTATCTTCTA AGCCCTGGGG GCTTCCCCGG GCCCCAGCCC CGACCTAGAA    1140
CCCGCCCGCT GCCTGCCACG CTGCCACTGC CGCTTCCTCT ATAAAGGGAC CTGAGCGTCC    1200
GGGCCCAGGG GCTCCGCACA GCAGGTGAGG CTCTCCTGCC CCATCTCCTT GGGCTGCCCG    1260
TGCTTCGTGC TTTGGACTAC CGCCCAGCAG TGTCCTGCCC TCTGCCTGGG CCTCGGTCCC    1320
TCCTGCACCT GCTGCCTGGA TCCCCGGCCT GCCTGGGCCT GGGCTTGGTG GGTTTGGTTT    1380
TGGTTTCCTT CTCTGTCTCT GACTCTCCAT CTGTCAGTCT CATTGTCTCT GTCACACATT    1440
CTCTGTTTCT GCCATGATTC CTCTCTGTTC CCTTCCTGTC TCTCTCTGTC TCCCTCTGCT    1500
CACCTTGGGG TTTCTCTGAC TGCATCTTGT CCCCTTCTCT GTCGATCTCT CTCTCGGGGG    1560
TCGGGGGTG CTCTCTCCCA GGGCGGGAGG TCTGTCTTCC GCCGCGTGCC CCGCCCCGCT    1620
CACTGTCTCT CTCTCTCTCT CTCTTTCTCT GCAGGTTCTC CCCATGACAC CACCTGAACG    1680
TCTCTTCCTC CCAAGGGTGT GTGGCACCAC CCTACACCTC CTCCTTCTGG GGCTGCTGCT    1740
GGTTCTGCTG CCTGGGGCCC AGGTGAGGCA GCAGGAGAAT GGGGGCTGCT GGGGTGGCTC    1800
AGCCAAACCT TGAGCCCTAG AGCCCCCCTC AACTCTGTTC TCCCCTAGGG GCTCCCTGGT    1860
GTTGGCCTCA CACCTTCAGC TGCCCAGACT GCCCGTCAGC ACCCCAAGAT GCATCTTGCC    1920
CACAGCACCC TCAAACCTGC TGCTCACCTC ATTGGTAAAC ATCCACCTGA CCTCCCAGAC    1980
ATGTCCCCAC CAGCTCT                                                  1997
```

(2) INFORMATION FOR SEQ ID NO: 11:

(i) SEQUENCE CHARACTERISTICS:
        (A) LENGTH:       10240 base pairs
        (B) TYPE:         nucleic acid

```
    (C) STRANDEDNESS:  single
    (D) TOPOLOGY:      linear (xi) SEQUENCE DESCRIPTION: SEQ ID NO:  11:

GAATTCCCCG GATCAAAGTC AGCATTAAAT CCCAGTTTAG GTTTTGAGGC TAAGTTCAAG       60

TTTGAGTCTA ATGTCATTTC AGCCTTGTTT GGAGGACTCA GAGATTTCAC TAGTTTCTCC      120

GCAGAGACCA CTGTAGAAAC TGCATTTCCC TGAGTTTTGG GCACAAGACT CCAGTCATCA      180

CCCCTCCCAC ACAGGGAAAG CCCCAAACCA ACTGCTGGCC TCCTCAAGAA AGAAACCGAA      240

TTTCACACAA CCTCCGAAAC TAAGATTGAA ACCAAGATTG GCCCATCTCA AGGCGCGTCC      300

TCCAGCACAT TGAGAATGTC GCTGATGGAG CCTCGGCCCA GCTCTCGAGC TTCCTTCCTT      360

TCTGTCTCTC ATGTCTTCTC ATCACTCCTT CTCACCTTCC CGTTTTTGTC CTGCAATGCC      420

CCCTTCTTCC TCTCTTCCTG GGGTTTTTCC CTTTATTTCT CACTGTACCA TTTTATATTT      480

TAATAAAGCC GAGGTCTCCT AGTCCATCAG CTCCTACTGT TGGAGAGGAG GCAGAAAGAA      540

ACAGCAGGAC GGCAAAGGGA CTCCAGAGAA AGAGACTCAG AGGAAAGGCA AGAAACAGGG      600

ACCAAGAGAG AGGCCAACAG TGACACAAGA CACAGTGAGG TTAAAAGAAA TAAGATGAGG      660

CCAAGATAGA GACCAAGCTA TTTAAAAGAG CCATCTGTGG CTACCCTTCT TCCGCCATCG      720

CATCTGGTCA GCCACCAAGA TTTTGCCTAG AAACGTTCCT CCTCTCCATT CTCCTGCTGC      780

TGCTGCTGCT GCTGCTGCTG CTGCTGCTGC TGCTGCTGCT GCTGCTGCTG CTGCCTTAAT      840

ACGAATGCAG GCTCTTGTCA TCTCCTTGCT GGGTTGTTGC AAAATCCTCC TAACTGGTCT      900

CCACACTTCT CATTTCCCCT CCAGCCCCCC ATCTTCCATA CTTCCATTTA TTTATTTTGG      960

CCATGCCCAT GGCATGTGGC AGTTCCAGGG GCCAGGGATC AAACCTGTGC CAATGCAGTG     1020

ACCGTGTCAG ATCCTTAACC CACTGCACAC AAGGCAACGC CCCTCGAGTC ATTCTCATTT     1080

TTTAAATATA CCAATTTGAG GGGGTCCCTC TTTCACTTAA AAATTTTGGC AGCTCCCTAT     1140

CATGATGAGA AGGAATTCCA AACCATTTTT CTTGTGTGCA AACCCTTCAG CATGTGTCCT     1200

CAGCTTACTT CCCAAGCCTC ATCCCTGCTC CTTCTACGTG TACCCATGTG TACATCTCCA     1260

CACACCATAT ACTCTTTTTT ACCTCCCATC TTTGCACCTT CTGTTCCCTC TCTCTGCCCC     1320

TCACCATCTT TTTTGCTTTG ATACTTAATG CCTCTCCCTC AGGCCAGGTT CAATGGCTTT     1380

TCTGTGGGCT GCTTTAAGCC CACTGTCATG GAACTTATCA CATTTTATTT TATTTGACTT     1440

TCTTTTTAGG GCCGCACCCA GCATATGGAG ATTCCCAGGC TAGGGATCTA ATCGGAGCTG     1500

TATCTGCCAG CCTGCGCTGG AGCCACAGCA ACGTGGGATC CGAGCCTGAG GGGTTTTGAT     1560

GTCCTGTGGC ACAGAAGTTA CATTCAGGCT GTGCATGAAC TATTTCTCCT GTTCTCCTCC     1620

CCCTGCTTGA GGCCCTGCAG CTTTGCCTCT CATGCCTTGC TGCTCTGACC TATGACTTCT     1680

TTTTGTTTGC ATTCCATCTC TTTAGTTTTC TCTCTGTTCC ACAAACATTT ACTGAGCATC     1740

TACATGAGGC ATTGAGGATA CGGATGGGAA AGACAGTCCC CTGACCTCTG GGACCTCAAA     1800

GACCAATTGT GGAAGACTGG TTGGTTATCA GATAATTACA ATGAAGTGTG GGAGTCCCTG     1860

TCATGGGTCA GCAGGTAATG AACCCAGTAA ACGATCCATG AGGATGCAGA TTCAATCCCT     1920

GGCCTTGCTC AGCGGGTTAA GGATCCAGCG TTCCCACAAG CTGTGGTGTA GGTCGCAGAT     1980

GCGACTCAGA TCTTGCATTG CTGTGGCTGT GGTGTAGGCT GGTGGCTACC CCTAGCCTGG     2040

GAACCTCCAT ATGCCTCAGG TGCGGCCCTA AAAGACAAAA AAAAAAAAGA GAGAAACTTT     2100

TCTTTTTCTT AATGTGTAAC CTACAAGCTA AGTGAAAACT GGCTCCTATT CCATAACGTT     2160

TGTATCATTT TTCATACTAG CCAAATACTA GAAACAGGGA GTTCCCGTCG TGGTGCAGCA     2220
```

-continued

```
GAAACAAATT CGACTAGGAA CCATGAGGTT GCGGGTTCGA TCCCTGGCCT TGCTCAGTGG    2280

GTTAAGGATC CGGCGTTGCC GTGAGCTGTG GTGTAGGTCG CAGATGTGGC TCGGATCTAG    2340

TGTTGCTGTG GCTCTGGTGT AGGCCGGCAG CAACAGCTCT GATTAGACTC CTAGCCTGAG    2400

AACCTCCATA AGCTGTGGCT GCGGCCCTAT AAAGACAAAA AAAAAAAAAA GGCCAAATAC    2460

TAGAAACAAA CCAAATGCCC ATCAACAGAA GAATAGATAA GTTAATTGGG GTATATGCAC    2520

ACAATAGCAT CACACAATAA CATGCACACA ATAACATCAC AATGAAATAA AAATTACTAC    2580

TGACAGACAC AACCATATAG ATGAATTTCA CAAACACAAC AGCGAGAATA AAGCCAAGC     2640

ACAGATGAGT TGTCTGTGTG GATTCATTTC TATGAAGTTC AAGCGCAGGA AGAACTTAAT    2700

CTATAGTGAC AGAGGTCAGA GAGCAGTTGG TTGTCTTTGG CAGGTATGAA CTGGGAGTGG    2760

GCATGAGAGA ACTTTCTGGA GACCTAAAAA TATATTGGAC TGGATGGTGG CAACATGGCT    2820

ACAAGAAGAT GGAAAAGTTC CTCAGGCTGT CCACTTGGGA GACGGGCTTC TCACGGGACC    2880

TAAGTTCTGC ATCAGCAGAG GGGGAAATCC TTAATGATTT GACAATTACA AAGTGTATTG    2940

GCTTTACCGA TGTATTTTCA ACACAATCCC TCTGCTGTCC CCACCCCACC CTAGGTCACC    3000

ACCCTTAAGC TCCACCTGTG TGGAATTCTG AAGCCTCCCC TGTAGAGAAC TTTAGCAGTT    3060

GCCACGTTCT TTTGATGCAG GAACGTGTTG TCTAGAGTTA GACACATCTG ATCTGTGGGG    3120

CCCACCCAAG GTTGGGACAT GGTGGGGGGC GGCCTTCTGC AGTGAGATGA AACCTCATTG    3180

TAGGTGATTT CGTGGCCTCA TCCCTGAGTC AGATCTTCCA AATGAGGACA CTTTGGAGAG    3240

CAAAAGGGGG CTCCCTGAAG ATTTCCTCCA GGACAGCAGG AACAAACCAG GATGTCCCAG    3300

GCAGGAGGGT ATAGAAGGGA ACTTGTTGAT ATGAAATCAG CCAGATGACC TGGAAAATAC    3360

ACAGACTGGG ACAAGTGTGA CTTGAGCCTC TTGGGCCCAG GACAGGGGTA CAGAGGAGGA    3420

AACGTGCACA GAGAGAAGCC CGTAATCAGC CAAGGCTGCA GAGGTGTTAT ACATAATCGC    3480

TCTTCACGCA ACCGGGCAAG CAGCCCACGC CCCAGCTGCA CTCCATCTCC TCCTCTGAAC    3540

TCACCGTCCC TTCTCTGGAA CTCCTAAGCC TGACCCCGCT CCCTGGCCCT CCCAGCCCAC    3600

GGTTCCCCTG ACCCCACTCC CTTTCCCAGA ACTCAGTCAT CTGAGCCCCC AGCCTGCGTT    3660

CTCTCCTAGG CCTCAGCCTT TCCTGCCTTC GCGTGAAACA GCAGCATCTT CTAAGCCCTG    3720

GGCTTCCCCA GGCCCCAGCC CCGGCCTAGA ACCCGCCCAG CCGACCTGCC CACGCTGCCA    3780

CTGCCGGCTT CCTCTATAAA GGGACCCAGG GCGCCCAGAA AGGGCCCAC AGGGGTCCCG     3840

CACAGCAGGT GAGACTCTCC CACCCCATCT CCTAGGGCTG TCCGGGTGCT GGACTCCCCC    3900

CTCACTTCGG TCCCTCCGCC CGCTCCCTGG CCTTCCTGCC CCTCCTGCAT CTTCACCCCG    3960

GCCTGGGCCT TGGTGGGTTT GGTTTTGGTT TGTTCTCTCT GATTCTTTAT CTGTCAGGCT    4020

CTTTCTAGCT CTCACACACT CTGATCCCTC TCTGTTCCCT TCCCATCTCT GTTTCTCTCT    4080

GGGTCTCCCC CTGCTCACCT CGGGATTTCC CTGAGTGCCT CTGGTCCCCT TCTCTGTCTG    4140

GCGCCCCGTC TCTTGTCTCT CGGGGTGGCT GTCTCCGAGG GCAGGAGGCC TTCTTCCGCA    4200

GGTGCCCCGC CCCGCTCACT GTCTCTCTCC CCCCACAGGT TTTCCCCATG ACACCACCTG    4260

GACGCCTCTA CCTCCGGAGG GTGTGCAGCA CCCCCATCCT CCTCCTCCTG GGGCTGCTGC    4320

TGGCCCTGCC GCCCGAGGCC CAGGTGAGGC AGCAGGAGAG CGGGCCGTGG GGGCAGCCTT    4380

CGCCAACCTT GGGCCTCAGA GCCTCTCTGA CGCTCTTCTC CCCTAGGGGC TCCCTGGCGT    4440

CGGCCTCCCA CCCTCAGCTG CACAGCCTGC CCATCAGCAC CCCCAAAGC ACTTGGCCAG     4500

AGGCACCCTC AAACCTGCCG CTCACCTCGT TGGTAAACAT CCACCTGGCC TCCCAGACCT    4560

GTAGCCCCCA GTCCTCCTCC TATGCCCCTG CTTCAGGGAC TGAAGCATCC CTCCCCCCCA    4620
```

```
TCTCCCCCCA CCCCCTAAAT GGAGGCATCC CACTCCCGAC TCCCTCCCAA CCATCCCCCA   4680

GGAACTCAGT CCAGCACCTG CTTCCTCAGG GATTGAGACC TCCGACCCCC AGGTCCTTGA   4740

CTCCCACCCC CTCTGGCTCT TCCTAGGAGA CCCCAGCACC CCGGACTCAC TGCGCTGGAG   4800

AGCGAACACG GATCGTGCCT TCCTCCGCCA TGGCTTCTTG CTGAGCAACA ACTCCCTGCT   4860

GGTCCCCACC AGTGGCCTCT ACTTTGTCTA CTCCCAGGTC GTCTTCTCCG GGAAGGCTG    4920

CTTCCCCAAG GCCACCCCCA CCCCTCTCTA CCTGGCCCAC GAGGTCCAGC TCTTCTCCTC   4980

CCAGTACCCC TTCCACGTGC CGCTCCTCAG CGCTCAGAAG TCCGTGTGCC CCGGGCCACA   5040

GGGACCTTGG GTGCGCTCTG TGTACCAGGG GGCTGTGTTC CTGCTCACCC AGGGAGATCA   5100

GCTGTCCACA CACACAGACG GCACCCCCCA CCTGCTCCTC AGCCCCAGTA GCGTCTTCTT   5160

TGGAGCCTTC GCTCTATAGA AGAATCCAGA AAGAAAAAAA TTGGTTTCAA GGCCTTCTCC   5220

CCTTTTCACC TCCCTTATGA CCACTTCGGA GGTCACCGCG CCTCTCCTCT GACAATTTCC   5280

AACAGTCTCA TCTTCCCCCA CGCTCAGCAC CTGGAGCTTC TGTAGAAGGA ATTCTAGGCA   5340

CCTCGGGGGA ACTGGAACCA CCCCGGATGC TCTGCTGAGG ATCTGAATGC CCGCCTGGAG   5400

CCCTTCCCCT GTCCTGCCCG TCTAGGGGCC CTCGTCCAGG ACGTGGAAGG GAAGCTGACC   5460

CATGAGGGAC TTTGAACGGA TGACCGGAGC GGTGTGGGGG GGTTATTTAT GAAGGGGAAA   5520

ATTAAATTAT TTATTTATGG AGGATGGAGA GAAGGGAATC ACAGAGGGAT GTCAGAAGAG   5580

TGTGACACAT GTGCCCAAGA GATAAAGTGA CAGAAGGCAT GGGCTCCAGA TGACCCGGCC   5640

AGAGAGGGCA AAGTGGCTCA GGAAGGGGCT GCTTGACTGG AGGCTCATGA GGAGACGGCT   5700

GACCCTCGAT GAAACCCAAT AAAGCTCTTT TCTCTGAAAT GCTGTCTGCT CGTATCTGTC   5760

ACTCGGGAGG GGAGAATTCT CCAGATGTCT CTAAGGAGTG GAGGGAGGAC AGGAATCAGA   5820

GGGGACGGGA GCTGTGGGTG TGTGATGAGG CCTAAGGGGC TCAGGTGAGA GATGGCGGCC   5880

TCAGGGTGAG GGCAGCCAGA CCCCTGCAGG AGAAGCAGAT GGTTCCTCTG AGAAGACAAA   5940

GGAAGAGATG CAGGGCCAAG GTCTTGAGAA CCGAGGTCGG GGGTCGCCTG GCAGATATGG   6000

CCACAGGTAG AGGGACAGAG GAATAGGGGT GACAGGAGGC TTCCCGGGAG AAGGGAACAC   6060

ACTGAGGGGT GTTCGGGATT CTGAGGGAGG AGCACGGGGA CGCCCTGGGA GACATGCCGT   6120

CCAGGGCCAT GAGGAGTGGG AGAGCCTCTG AGGCTAGCGG CTGGAGATAC AGGGACATTT   6180

GAGGAGACAC GGTCATGGCC AGGAGCCGCG AGGGCCTGGA CAGTCTCTAG GAATCTCGAA   6240

GAAGCAGGAA TTCTTTGAGG ATACGTGGCC ACACAAAGGG AGGCTGAGGT GTGGGGACTT   6300

CATGCAGAAG TCAGGGCCTC ACATTCCCTT GGAAGCCGAG ACTGAAACCA GCAGCAGAGT   6360

TTTGGTGAGT TCCTGTCAGA GTGAAAGGAG AAGGCCCGCC ATGGTGGGTT TGTGAATTCC   6420

CAGCCTGGCT TCCTCTCCCT CTGGGGCTGT CCCAGGCCTG TTCCTGCCGT CCTCCCCCAG   6480

CCCGTGTAGG GCCTCCAGCT GCCCTTCTCC CAGCTCCTCT TCCCTCCAGG AGACGAAACA   6540

TGGGTCTCAG CACCCAGCGC GGTGTCGTCT AAGTTTTCTC TCCATTAAGA ACTCAGCTTT   6600

CTGAAGCTCC TCCCATTCCT AGTTCTACCC CTACCTGAGC CCTGTTCGGA AATCAGAGAG   6660

AAATAGAAGT CATCCCCCAA AGAAAAGGAA TTTGTCCCCC AAAGAAACAG AACTTGTCCC   6720

CCAAAGAAAT GGAAACAATG GGAAATGGGA GGCAGGGGG ACCTGGGGTC CAGCCTCCAG    6780

GGTCCTACAC ACAGAGCAGT AACTGGCCCA GCAAGCCCAC CTCAGGATCC GGGCAGGGAG   6840

GGTAGGAAGT ATCCCTGATG CCTGGGTGTC CCCAACTTTC CAAACCGCCG CCCCCGCTAT   6900

GGAGATGAAA CTAAGACAGA AGGTGCAGGG CCCGCTACCG CTTCCTCCAG ATGAGCTCAT   6960
```

-continued

```
GGGTTTCTCC ACCAAGGAAG TTTTCCGCTG GTTGAAAGAG AGCCTCTCCC CGCCCTCTTC      7020

TCACCCAGAG CGTATAAATG CAGCTGTTTG CACACCCAGC CAGCAGAAGC TCCCAGAGTG      7080

AGGACACCAG GGGACCAGCC AGGAGAGAGA CAAGCCATCT CCAGGACCCC CTAGAAATAA      7140

CCTCTCAGAA GACACACCCC CGAACAGGCA GCCGGACGAC TCTCTCCCTC TCACACGCTG      7200

CCCCGGGGCG CCACCATCTC CCAGCTGGAC CTGAGCCCCT CTGAAAAAGA CACCATGAGC      7260

ACTGAGAGCA TGATCCGAGA CGTGGAGCTG GCGGAGGAGG CGCTCGCCAA GAAGGCCGGG      7320

GGCCCCCAGG GCTCCAGGAG GTGCCTGTGC CTCAGCCTCT TCTCCTTCCT CCTGGTCGCA      7380

GGAGCCACCA CGCTCTTCTG CCTACTGCAC TTCGAGGTTA TCGGCCCCCA GAAGGAAGAG      7440

GTGAGCGCCT GGCCAGCCTT GGCTCATTCT CCCACCCGGA GAGAAATGGG AAGAAAGAG      7500

GGCCAGAGAC GAGCTGGGGG AAAGAAGTGT GCTGATGGGG AGTGTGGGGA GGAAATCATG      7560

GAGAAAGATG GGGAGGCAGA AGGAGACGTG GAGAGAGATG GGGGGAGAGA GAGAAGGATG      7620

GAGAGAAATC CGGTGGCCCG GCCCTTGGAA ATGCTCTCTA AATATTTGTT GCACGAATGA      7680

GTGAGTAAGC AGGGACACCG ATATAAAGAG AGATGAGTAG ACAGACAAGG GGTGTGGTAG      7740

AAAGATAGGG AAAAAACAAG TGATCTGGAT AAAGATAGTG AGACAGGAAG AGGTAGAGGA      7800

GATAGGAAAG AGAGATAAGG AGAGAAGAAG GAAGCGTGGG TGTCTGGCAC GTGGAAGGCA      7860

CTCAATGAAG GAGTTGTTGA ATGGATGGGT GGATGAGAAA ATGGATGAGT GGAGAGAAAA      7920

AACTAGACAT CAGGGCAGAG AGTACAAGCT AGAGAAGCAG GTGGCTGTTT TCCCTTCAGA      7980

GGGGACTTAT TCAAATCTAA TTAATCCTTC TTCTTCTCCC CAACAGTTTC CAGCTGGCCC      8040

CTTGAGCATC AACCCTCTGG CCCAAGGACT CAGTAAGTAT CTCTAAAACC TGTCTCTCAG      8100

TTCTGAGCTT GGACAGGGGT GGGGTTAGTG CTGGGGTGGA AGGAAGAAGG GAAATTTAGG      8160

GTCTGGGTTT GGCGGGGGGA ATGCAGGTCA AAGTAGTGAG ATATTTTCTG GGAAGTCTGA      8220

GGGTCTCATC TTTTTCTTTC CTCTTTCCTC CTCAGGATCA TCGTCTCAAA CCTCAGATAA      8280

GCCCGTCGCC CACGTTGTAG GTAAGAGTTC TGAGGATGTG TCTGGGGGAT GAAGAAATAG      8340

GCAGGACAGA GAGGGATAGG ATTTGGGGGC TGAAGCCAGG CTGAGGGTAG CCAGAGCTTG      8400

GAGATAGTAT GAGGAGGACT CGCTGAGCTC CAGGGGAGGA TGGGGGATAC TCAGAACTTG      8460

AGGAGGATAC TCGGAACCTC ATGGACAGAT GGGATGTGGG AAGACAGACC GAGGGGACAG      8520

GAACCGGATG TGGGGGGCGG GCAGAACTCG AGGGCCAGGA TGTGGAGAGT GGAACTGACA      8580

GGGTCACACT GACTCACCCC TCCCTCTTTG TCTCCTCCCT CCAGCCAATG TCAAAGCCGA      8640

GGGACAGCTC CAATGGCAGA GTGGGTATGC CAATGCCCTC CTGGCCAACG GCGTGAAGCT      8700

GAAAGACAAC CAGCTGGTGG TGCCGACAGA TGGGCTGTAC CTCATCTACT CCCAGGTCCT      8760

CTTCAGGGGC CAAGGCTGCC CTTCCACCAA CGTTTTCCTC ACTCACACCA TCAGCCGCAT      8820

CGCCGTCTCC TACCAGACCA AGGTCAACCT CCTCTCTGCC ATCAAGAGCC CTTGCCAGAG      8880

GGAGACCCCC GAGGGGCCG AGGCCAAGCC CTGGTACGAA CCCATCTACC TGGGAGGGGT      8940

CTTCCAGCTG GAGAAGGATG ATCGACTCAG TGCCGAGATC AACCTGCCCG ACTATCTGGA      9000

CTTTGCTGAA TCTGGGCAGG TCTATTTTGG GATCATTGCC CTGTGAGGGG GCAGGACATC      9060

CGTTCCCTCC CCTGTCCATC CCTTTATTAT TTTACTCCTT CAGACCCCCT CACGTCCTTC      9120

TGGTTTAGAA AGAGAATGAG GGGCTGGGGA CTGGGCTCCA AGCTTAAAAC TTTAAACAAC      9180

AACAGCAACA CTTAGAAAAT AGGGATTCAG GGATGTGTGG CCTGGACAAC CAGGCACTGA      9240

CCACCACCAA GAATTGGAAC TGGGGCTTCC AGACTCGCTG GGGTCCTTGG GTTTGGATTC      9300

CTGGATGCAA CCTGGGACAT CTGGAATGTG GCTGCCAGGG AAGCTTGGGT TCCAATCGGA      9360
```

```
ATACTTCAGA ACATTCCTTG AGAAGATTTC ACCTCAATCT TGATGACTTT TTAGGCTTCC      9420

CTTTCTTCCA ATTTTCCAGA CTTCCCTGGG ATGGGGAGCC CAGCCCCAAA CCCCACAGGC      9480

CAGCTCCCTC TTATTTATAT TTGCACTTGG CATTATTATT TATTTATTTA TTTATTATTT      9540

ATTTACTAGT GAATGTATTT ATTCAGGAGG GCGAGGTGTC CTGGGAGACC AGCATAAGG       9600

GCTGCCTTGG TTCAGATGTG TTTTCTGTGA AAACGGAGCT GAACTGTAGG TTGCTCCCAC      9660

CTGGCCTCCT AGCCTCTGTG CCTCCTTTTG CTTATGTTTT TAAAAACAAA TATTTATCTG      9720

ATCGAGTTGT CTAAATAATG CTGATTTGGT GACTAACTTG TCGCTACATC GCTGAACCTC      9780

TGCTCCCCAG GGGAGTTGTG TCTGTAACCG CCCTACTGGT CAGTGGCGAG AAATAAAAGC      9840

GTGCTTAGAA AAGAAATCTG GCCTCTTTCT GCGACTGAAT TCTGCATCTC CTTGGGGGGG     9900

TGAGGCTGCT CCCCAAAATT CTTTCTCCAC CGGGCTTAGG ATTCCCTGGG CTTCACTCCT      9960

GAGCTTGGAC TGCCTGGCTC AGGAGCCTCT GCAAGAAACA AAGCCCAGCC AAACAGGTCC     10020

CTCCCCTAAG AAAGGAACCT GAAGGTAATT ACCTCTCCCT CAGGGTGTGG GAATTTCCAA     10080

GTCTGGGAAT TCCTATCCAG CTGGGGAAGT CTGCAGTGCA GGTGAGACTT CCGGCTGAAA     10140

GAGCCAGGGA GCGGCCAGAT GCTCAGGTAC CTGAACCAGA GCCAAGGGAC TTCCAGACAG     10200

TGAGGCAACT GGGCTCCAAA TAACCTGATC CGGGGAATTC                            10240

(2) INFORMATION FOR SEQ ID NO: 12:

(i) SEQUENCE CHARACTERISTICS:
            (A) LENGTH:       1644 base pairs
            (B) TYPE:         nucleic acid
            (C) STRANDEDNESS: single
            (D) TOPOLOGY:     linear (xi) SEQUENCE DESCRIPTION: SEQ ID NO: 12:

CCTCAGCGAG GACAGCAAGG GACTAGCCAG GAGGGAGAAC AGAAACTCCA GAACATCCTG        60

GAAATAGCTC CCAGAAAAGC AAGCAGCCAA CCAGGCAGGT TCTGTCCCTT TCACTCACTG       120

GCCCAAGGCG CCACATCTCC CTCCAGAAAA GACACCATGA GCACAGAAAG CATGATCCGC       180

GACGTGGAAC TGGCAGAAGA GGCACTCCCC AAAAGATGG GGGGCTTCCA GAACTCCAGG        240

CGGTGCCTAT GTCTCAGCCT CTTCTCATTC CTGCTTGTGG CAGGGGCCAC CACGCTCTTC       300

TGTCTACTGA ACTTCGGGGT GATCGGTCCC CAAAGGGATG AGAAGTTCCC AAATGGCCTC       360

CCTCTCATCA GTTCTATGGC CCAGACCCTC ACACTCAGAT CATCTTCTCA AAATTCGAGT       420

GACAAGCCTG TAGCCCACGT CGTAGCAAAC CACCAAGTGG AGGAGCAGCT GGAGTGGCTG       480

AGCCAGCGCG CCAACGCCCT CCTGGCCAAC GGCATGGATC TCAAAGACAA CCAACTAGTG       540

GTGCCAGCCG ATGGGTTGTA CCTTGTCTAC TCCCAGGTTC TCTTCAAGGG ACAAGGCTGC       600

CCCGACTACG TGCTCCTCAC CCACACCGTC AGCCGATTTG CTATCTCATA CCAGGAGAAA       660

GTCAACCTCC TCTCTGCCGT CAAGAGCCCC TGCCCCAAGG ACACCCCTGA GGGGGCTGAG       720

CTCAAACCCT GGTATGAGCC CATATACCTG GGAGGAGTCT TCCAGCTGGA GAAGGGGGAC       780

CAACTCAGCG CTGAGGTCAA TCTGCCCAAG TACTTAGACT TTGCGGAGTC CGGGCAGGTC       840

TACTTTGGAG TCATTGCTCT GTGAAGGGAA TGGGTGTTCA TCCATTCTCT ACCCAGCCCC       900

CACTCTGACC CCTTTACTCT GACCCCTTTA TTGTCTACTC CTCAGAGCCC CCAGTCTGTG       960

TCCTTCTAAC TTAGAAAGGG GATTATGGCT CAGAGTCCAA CTCTGTGCTC AGAGCTTTCA      1020

ACAACTACTC AGAAACACAA GATGCTGGGA CAGTGACCTG GACTGTGGGC CTCTCATGCA      1080

CCACCATCAA GGACTCAAAT GGGCTTTCCG AATTCACTGG AGCCTCGAAT GTCCATTCCT      1140
```

```
GAGTTCTGCA AAGGGAGAGT GGTCAGGTTG CCTCTGTCTC AGAATGAGGC TGGATAAGAT      1200

CTCAGGCCTT CCTACCTTCA GACCTTTCCA GACTCTTCCC TGAGGTGCAA TGCACAGCCT      1260

TCCTCACAGA GCCAGCCCCC CTCTATTTAT ATTTGCACTT ATTATTTATT ATTTATTTAT      1320

TATTTATTTA TTTGCTTATG AATGTATTTA TTTGGAAGGC CGGGGTGTCC TGGAGGACCC      1380

AGTGTGGGAA GCTGTCTTCA GACAGACATG TTTTCTGTGA AAACGGAGCT GAGCTGTCCC      1440

CACCTGGCCT CTCTACCTTG TTGCCTCCTC TTTTGCTTAT GTTTAAAACA AAATATTTAT      1500

CTAACCCAAT TGTCTTAATA ACGCTGATTT GGTGACCAGG CTGTCGCTAC ATCACTGAAC      1560

CTCTGCTCCC CACGGGAGCC GTGACTGTAA TTGCCCTACA GTCAATTGAG AGAAATAAAG      1620

ATCGCTTAAA ATAAAAAACC CCCC                                             1644

(2) INFORMATION FOR SEQ ID NO: 13:

(i) SEQUENCE CHARACTERISTICS:
        (A) LENGTH:       1890 base pairs
        (B) TYPE:         nucleic acid
        (C) STRANDEDNESS: single
        (D) TOPOLOGY:     linear (xi) SEQUENCE DESCRIPTION: SEQ ID NO: 13:

AAACAGAGAG AGATAGAGAA AGAGAAAGAC AGAGGTGTTT CCCTTAGCTA TGGAAACTCT        60

ATAAGAGAGA TCCAGCTTGC CTCCTCTTGA GCAGTCAGCA ACAGGGTCCC GTCCTTGACA       120

CCTCAGCCTC TACAGGACTG AGAAGAAGTA AAACCGTTTG CTGGGGCTGG CCTGACTCAC       180

CAGCTGCCAT GCAGCAGCCC TTCAATTACC CATATCCCCA GATCTACTGG GTGGACAGCA       240

GTGCCAGCTC TCCCTGGGCC CCTCCAGGCA CAGTTCTTCC CTGTCCAACC TCTGTGCCCA       300

GAAGGCCTGG TCAAAGGAGG CCACCACCAC CACCGCCACC GCCACCACTA CCACCTCCGC       360

CGCCGCCGCC ACCACTGCCT CCACTACCGC TGCCACCCCT GAAGAAGAGA GGGAACCACA       420

GCACAGGCCT GTGTCTCCTT GTGATGTTTT TCATGGTTCT GGTTGCCTTG GTAGGATTGG       480

GCCTGGGGAT GTTTCAGCTC TTCCACCTAC AGAAGGAGCT GGCAGAACTC CGAGAGTCTA       540

CCAGCCAGAT GCACACAGCA TCATCTTTGG AGAAGCAAAT AGGCCACCCC AGTCCACCCC       600

CTGAAAAAAA GGAGCTGAGG AAAGTGGCCC ATTTAACAGG CAAGTCCAAC TCAAGGTCCA       660

TGCCTCTGGA ATGGGAAGAC ACCTATGGAA TTGTCCTGCT TTCTGGAGTG AAGTATAAGA       720

AGGGTGGCCT TGTGATCAAT GAAACTGGGC TGTACTTTGT ATATTCCAAA GTATACTTCC       780

GGGGTCAATC TTGCAACAAC CTGCCCCTGA GCCACAAGGT CTACATGAGG AACTCTAAGT       840

ATCCCCAGGA TCTGGTGATG ATGGAGGGGA AGATGATGAG CTACTGCACT ACTGGGCAGA       900

TGTGGGCCCG CAGCAGCTAC CTGGGGGCAG TGTTCAATCT TACCAGTGCT GATCATTTAT       960

ATGTCAACGT ATCTGAGCTC TCTCTGGTCA ATTTTGAGGA ATCTCAGACG TTTTTCGGCT      1020

TATATAAGCT CTAAGAGAAG CACTTTGGGA TTCTTTCCAT TATGATTCTT TGTTACAGGC      1080

ACCGAGAATG TTGTATTCAG TGAGGGTCTT CTTACATGCA TTTGAGGTCA AGTAAGAAGA      1140

CATGAACCAA GTGGACCTTG AGACCACAGG GTTCAAAATG TCTGTAGCTC CTCAACTCAC      1200

CTAATGTTTA TGAGCCAGAC AAATGGAGGA ATATGACGGA AGAACATAGA ACTCTGGGCT      1260

GCCATGTGAA GAGGGAGAAG CATGAAAAAG CAGCTACCCA GGTGTTCTAC ACTCATCTTA      1320

GTGCCTGAGA GTATTTAGGC AGATTGAAAA GGACACCTTT TAACTCACCT CTCAAGGTGG      1380

GCCTTGCTAC CTCAAGGGGG ACTGTCTTTC AGATACATGG TTGTGACCTG AGGATTTAAG      1440

GGATGGAAAA GGAAGACTAG AGGCTTGCAT AATAAGCTAA AGAGGCTGAA AGAGGCCAAT      1500
```

```
GCCCCACTGG CAGCATCTTC ACTTCTAAAT GCATATCCTG AGCCATCGGT GAAACTAACA    1560

GATAAGCAAG AGAGATGTTT TGGGGACTCA TTTCATTCCT AACACAGCAT GTGTATTTCC    1620

AGTGCCAATT GTAGGGGTGT GTGTGTGTGT GTGTGTGTGT GTGTATGACT AAAGAGAGAA    1680

TGTAGATATT GTGAAGTACA TATTAGGAAA ATATGGTTG CATTTGGTCA AGATTTTGAA     1740

TGCTTCCTGA CAATCAACTC TAATAGTGCT TAAAAATCAT TGATTGTCAG CTACTAATGA    1800

TGTTTTCCTA TAATATAATA AATATTTATG TAGATGTGCA TTTTTGTGAA ATGAAAACAT    1860

GTAATAAAAA GTATATGTTA GGATACAAAT                                    1890

(2) INFORMATION FOR SEQ ID NO: 14:

(i) SEQUENCE CHARACTERISTICS:
        (A) LENGTH:       1541 base pairs
        (B) TYPE:         nucleic acid
        (C) STRANDEDNESS: single
        (D) TOPOLOGY:     linear (xi) SEQUENCE DESCRIPTION: SEQ ID NO: 14:

GGGTGTCTCA CAGAGAAGCA AAGAGAAGAG AACAGGAGAA ATGGTGTTTC CCTTGACTGC      60

GGAAACTTTA TAAAGAAAAC TTAGCTTCTC TGGAGCAGTC AGCGTCAGAG TTCTGTCCTT    120

GACACCTGAG TCTCCTCCAC AAGGCTGTGA GAAGGAAACC CTTTCCTGGG GCTGGGTGCC    180

ATGCAGCAGC CCATGAATTA CCCATGTCCC CAGATCTTCT GGGTAGACAG CAGTGCCACT    240

TCATCTTGGG CTCCTCCAGG GTCAGTTTTT CCCTGTCCAT CTTGTGGGCC TAGAGGGCCG    300

GACCAAAGGA GACCGCCACC TCCACCACCA CCTGTGTCAC CACTACCACC GCCATCACAA    360

CCACTCCCAC TGCCGCCACT GACCCCTCTA AGAAGAAGG ACCACAACAC AAATCTGTGG     420

CTACCGGTGG TATTTTTCAT GGTTCTGGTG GCTCTGGTTG GAATGGGATT AGGAATGTAT    480

CAGCTCTTCC ACCTGCAGAA GGAACTGGCA GAACTCCGTG AGTTCACCAA CCAAAGCCTT    540

AAAGTATCAT CTTTTGAAAA GCAAATAGCC AACCCCAGTA CACCCTCTGA AAAAAAAGAG    600

CCGAGGAGTG TGGCCCATTT AACAGGGAAC CCCCACTCAA GGTCCATCCC TCTGGAATGG    660

GAAGACACAT ATGGAACCGC TCTGATCTCT GGAGTGAAGT ATAAGAAAGG TGGCCTTGTG    720

ATCAACGAAA CTGGGTTGTA CTTCGTGTAT TCCAAAGTAT ACTTCCGGGG TCAGTCTTGC    780

AACAACCAGC CCCTAAACCA CAAGGTCTAT ATGAGGAACT CTAAGTATCC TGAGGATCTG    840

GTGCTAATGG AGGAGAAGAG GTTGAACTAC TGCACTACTG GCCAGATATG GGCCCACAGC    900

AGCTACCTGG GGGCAGTATT CAATCTTACC AGTGCTGACC ATTTATATGT CAACATATCT    960

CAACTCTCTC TGATCAATTT TGAGGAATCT AAGACCTTTT TCGGCTTGTA TAAGCTTTAA   1020

AAGAAAAAGC ATTTTAAAAT GATCTACTAT TCTTTATCAT GGGCACCAGG AATATTGTCT   1080

TGAATGAGAG TCTTCTTAAG ACCTATTGAG ATTAATTAAG ACTACATGAG CCACAAAGAC   1140

CTCATGACCG CAAGGTCCAA CAGGTCAGCT ATCCTTCATT TTCTCGAGGT CCATGGAGTG   1200

GTCCTTAATG CCTGCATCAT GAGCCAGATG GAAGGAGGTC TGTGACTGAG GGACATAAAG   1260

CTTTGGGCTG CTGTGTAGCA ATGCAGAGGC ACAGAGAAAG AACTGTCTGA TGTTAAATGG   1320

CCAAGAGAAT TTTAACCATT GAAGAAGACA CCTTTACACT CACTTCCAGG GTGGGTCTAC   1380

TTACTACCTC ACAGAGGCCG TTTTTGAGAC ATAGTTGTGG TATGAATATA CAAGGGTGAG   1440

AAAGGAGGCT CATTTGACTG ATAAGCTAGA GACTGAAAAA AAGACAGTGT CTCATTGGCA   1500

CCATCTTTAC TGTTACCTGA TGTTTTCTGA GCCGACCTTT G                       1541
```

(2) INFORMATION FOR SEQ ID NO: 15:

(i) SEQUENCE CHARACTERISTICS:
        (A) LENGTH: 888 base pairs
        (B) TYPE: nucleic acid
        (C) STRANDEDNESS: single
        (D) TOPOLOGY: linear (xi) SEQUENCE DESCRIPTION: SEQ ID NO: 15:

```
GGCTGGTCCC CTGACAGGTT GAAGCAAGTA GACGCCCAGG AGCCCCGGGA GGGGGCTGCA      60
GTTTCCTTCC TTCCTTCTCG GCAGCGCTCC GCGCCCCCAT CGCCCCTCCT GCGCTAGCGG     120
AGGTGATCGC CGCGGCGATG CCGGAGGAGG GTTCGGGCTG CTCGGTGCGG CGCAGGCCCT     180
ATGGGTGCGT CCTGCGGGCT GCTTTGGTCC CATTGGTCGC GGGCTTGGTG ATCTGCCTCG     240
TGGTGTGCAT CCAGCGCTTC GCACAGGCTC AGCAGCAGCT GCCGCTCGAG TCACTTGGGT     300
GGGACGTAGC TGAGCTGCAG CTGAATCACA CAGGACCTCA GCAGGACCCC AGGCTATACT     360
GGCAGGGGGG CCCAGCACTG GGCCGCTCCT TCCTGCATGG ACCAGAGCTG GACAAGGGGC     420
AGCTACGTAT CCATCGTGAT GGCATCTACA TGGTACACAT CCAGGTGACG CTGGCCATCT     480
GCTCCTCCAC GACGGCCTCC AGGCACCACC CCACCACCCT GGCCGTGGGA ATCTGCTCTC     540
CCGCCTCCCG TAGCATCAGC CTGCTGCGTC TCAGCTTCCA CCAAGGTTGT ACCATTGCCT     600
CCCAGCGCCT GACGCCCCTG GCCCGAGGGG ACACACTCTG CACCAACCTC ACTGGGACAC     660
TTTTGCCTTC CCGAAACACT GATGAGACCT TCTTTGGAGT GCAGTGGGTG CGCCCCTGAC     720
CACTGCTGCT GATTAGGGTT TTTTAAATTT TATTTTATTT TATTTAAGTT CAAGAGAAAA     780
AGTGTACACA CAGGGGCCAC CCGGGGTTGG GGTGGGAGTG TGGTGGGGGG TAGTGGTGGC     840
AGGACAAGAG AAGGCATTGA GCTTTTTCTT TCATTTTCCT ATTAAAAA                  888
```

(2) INFORMATION FOR SEQ ID NO: 16:

(i) SEQUENCE CHARACTERISTICS:
        (A) LENGTH: 1906 base pairs
        (B) TYPE: nucleic acid
        (C) STRANDEDNESS: single
        (D) TOPOLOGY: linear (xi) SEQUENCE DESCRIPTION: SEQ ID NO: 16:

```
CCAAGTCACA TGATTCAGGA TTCAGGGGGA GAATCCTTCT TGGAACAGAG ATGGGCCCAG      60
AACTGAATCA GATGAAGAGA GATAAGGTGT GATGTGGGGA AGACTATATA AAGAATGGAC     120
CCAGGGCTGC AGCAAGCACT CAACGGAATG GCCCCTCCTG GAGACACAGC CATGCATGTG     180
CCGGCGGGCT CCGTGGCCAG CCACCTGGGG ACCACGAGCC GCAGCTATTT CTATTTGACC     240
ACAGCCACTC TGGCTCTGTG CCTTGTCTTC ACGGTGGCCA CTATTATGGT GTTGGTCGTT     300
CAGAGGACGG ACTCCATTCC CAACTCACCT GACAACGTCC CCCTCAAAGG AGGAAATTGC     360
TCAGAAGACC TCTTATGTAT CCTGAAAAGA GCTCCATTCA AGAAGTCATG GGCCTACCTC     420
CAAGTGGCAA AGCATCTAAA CAAAACCAAG TTGTCTTGGA ACAAAGATGG CATTCTCCAT     480
GGAGTCAGAT ATCAGGATGG GAATCTGGTG ATCCAATTCC CTGGTTTGTA CTTCATCATT     540
TGCCAACTGC AGTTTCTTGT ACAATGCCCA AATAATTCTG TCGATCTGAA GTTGGAGCTT     600
CTCATCAACA AGCATATCAA AAAACAGGCC CTGGTGACAG TGTGTGAGTC TGGAATGCAA     660
ACGAAACACG TATACCAGAA TCTCTCTCAA TTCTTGCTGG ATTACCTGCA GGTCAACACC     720
ACCATATCAG TCAATGTGGA TACATTCCAG TACATAGATA CAAGCACCTT TCCTCTTGAG     780
AATGTGTTGT CCATCTTCTT ATACAGTAAT TCAGACTGAA CAGTTTCTCT TGGCCTTCAG     840
```

```
GAAGAAAGCG CCTCTCTACC ATACAGTATT TCATCCCTCC AAACACTTGG GCAAAAAGAA      900

AACTTTAGAC CAAGACAAAC TACACAGGGT ATTAAATAGT ATACTTCTCC TTCTGTCTCT      960

TGGAAAGATA CAGCTCCAGG GTTAAAAAGA GAGTTTTTAG TGAAGTATCT TTCAGATAGC     1020

AGGCAGGGAA GCAATGTAGT GTGGTGGGCA GAGCCCCACA CAGAATCAGA AGGGATGAAT     1080

GGATGTCCCA GCCCAACCAC TAATTCACTG TATGGTCTTG ATCTATTTCT TCTGTTTTGA     1140

GAGCCTCCAG TTAAAATGGG GCTTCAGTAC CAGAGCAGCT AGCAACTCTG CCCTAATGGG     1200

AAATGAAGGG GAGCTGGGTG TGAGTGTTTA CACTGTGCCC TTCACGGGAT ACTTCTTTTA     1260

TCTGCAGATG GCCTAATGCT TAGTTGTCCA AGTCGCGATC AAGGACTCTC TCACACAGGA     1320

AACTTCCCTA TACTGGCAGA TACACTTGTG ACTGAACCAT GCCCAGTTTA TGCCTGTCTG     1380

ACTGTCACTC TGGCACTAGG AGGCTGATCT TGTACTCCAT ATGACCCCAC CCCTAGGAAC     1440

CCCCAGGGAA AACCAGGCTC GGACAGCCCC CTGTTCCTGA GATGGAAAGC ACAAATTTAA     1500

TACACCACCA CAATGGAAAA CAAGTTCAAA GACTTTTACT TACAGATCCT GGACAGAAAG     1560

GGCATAATGA GTCTGAAGGG CAGTCCTCCT TCTCCAGGTT ACATGAGGCA GGAATAAGAA     1620

GTCAGACAGA GACAGCAAGA CAGTTAACAA CGTAGGTAAA GAAATAGGGT GTGGTCACTC     1680

TCAATTCACT GGCAAATGCC TGAATGGTCT GTCTGAAGGA AGCAACAGAG AAGTGGGGAA     1740

TCCAGTCTGC TAGGCAGGAA AGATGCCTCT AAGTTCTTGT CTCTGGCCAG AGGTGTGGTA     1800

TAGAACCAGA AACCCATATC AAGGGTGACT AAGCCCGGCT TCCGGTATGA GAAATTAAAC     1860

TTGTATACAA AATGGTTGCC AAGGCAACAT AAAATTATAA GAATTC                    1906
```

(2) INFORMATION FOR SEQ ID NO: 17:

(i) SEQUENCE CHARACTERISTICS:
        (A) LENGTH:       1619 base pairs
        (B) TYPE:         nucleic acid
        (C) STRANDEDNESS: single
        (D) TOPOLOGY:     linear (xi) SEQUENCE DESCRIPTION: SEQ ID NO: 17:

```
GTCATGGAAT ACGCCTCTGA CGCTTCACTG GACCCCGAAG CCCCGTGGCC TCCCGCGCCC       60

CGCGCTCGCG CCTGCCGCGT ACTGCCTTGG GCCCTGGTCG CGGGGCTGCT GCTGCTGCTG      120

CTGCTCGCTG CCGCCTGCGC CGTCTTCCTC GCCTGCCCCT GGGCCGTGTC CGGGGCTCGC      180

GCCTCGCCCG GCTCCGCGGC CAGCCCGAGA CTCCGCGAGG GTCCCGAGCT TCGCCCGAC       240

GATCCCGCCG GCCTCTTGGA CCTGCGGCAG GGCATGTTTG CGCAGCTGGT GGCCCAAAAT      300

GTTCTGCTGA TCGATGGGCC CCTGAGCTGG TACAGTGACC CAGGCCTGGC AGGCGTGTCC      360

CTGACGGGGG GCCTGAGCTA CAAAGAGGAC ACGAAGGAGC TGGTGGTGGC CAAGGCTGGA      420

GTCTACTATG TCTTCTTTCA ACTAGAGCTG CGGCGCGTGG TGGCCGGCGA GGGCTCAGGC      480

TCCGTTTCAC TTGCGCTGCA CCTGCAGCCA CTGCGCTCTG CTGCTGGGGC CGCCGCCCTG      540

GCTTTGACCG TGGACCTGCC ACCCGCCTCC TCCGAGGCTC GGAACTCGGC CTTCGGTTTC      600

CAGGGCCGCT TGCTGCACCT GAGTGCCGGC CAGCGCCTGG GCGTCCATCT TCACACTGAG      660

GCCAGGGCAC GCCATGCCTG GCAGCTTACC CAGGGCGCCA CAGTCTTGGG ACTCTTCCGG      720

GTGACCCCCG AAATCCCAGC CGGACTCCCT TCACCGAGGT CGGAATAACG CCCAGCCTGG      780

GTGCAGCCCA CCTGGACAGA GTCCGAATCC TACTCCATCC TTCATGGAGA CCCCTGGTGC      840

TGGGTCCCTG CTGCTTTCTC TACCTCAAGG GGCTTGGCAG GGGTCCCTGC TGCTGACCTC      900

CCCTTGAGGA CCCTCCTCAC CCACTCCTTC CCCAAGTTGG ACCTTGATAT TTATTCTGAG      960
```

```
CCTGAGCTCA GATAATATAT TATATATATT ATATATATAT ATATATTTCT ATTTAAAGAG   1020

GATCCTGAGT TTGTGAATGG ACTTTTTTAG AGGAGTTGTT TTGGGGGGGG GGTCTTCGAC   1080

ATTGCCGAGG CTGGTCTTGA ACTCCTGGAC TTAGACGATC CTCCTGCCTC AGCCTCCCAA   1140

GCAACTGGGA TTCATCCTTT CTATTAATTC ATTGTACTTA TTTGCCTATT TGTGTGTATT   1200

GAGCATCTGT AATGTGCCAG CATTGTGCCC AGGCTAGGGG GCTATAGAAA CATCTAGAAA   1260

TAGACTGAAA GAAAATCTGA GTTATGGTAA TACGTGAGGA ATTTAAAGAC TCATCCCCAG   1320

CCTCCACCTC CTGTGTGATA CTTGGGGGCT AGCTTTTTTC TTTCTTTCTT TTTTTTGAGA   1380

TGGTCTTGTT CTGTCAACCA GGCTAGAATG CAGCGGTGCA ATCATGAGTC AATGCAGCCT   1440

CCAGCCTCGA CCTCCCGAGG CTCAGGTGAT CCTCCCATCT CAGCCTCTCG AGTAGCTGGG   1500

ACCACAGTTG TGTGCCACCA CACTTGGCTA ACTTTTTAAT TTTTTTGCGG AGACGGTATT   1560

GCTATGTTGC CAAGGTTGTT TACATGCCAG TACAATTTAT AATAAACACT CATTTTTCC    1619
```

(2) INFORMATION FOR SEQ ID NO: 18:

(i) SEQUENCE CHARACTERISTICS:
        (A) LENGTH:       1239 base pairs
        (B) TYPE:         nucleic acid
        (C) STRANDEDNESS: single
        (D) TOPOLOGY:     linear (xi) SEQUENCE DESCRIPTION: SEQ ID NO: 18:

```
AGCCTATAAA GCACGGGCAC TGGCGGGAGA CGTGCACTGA CCGACCGTGG TAATGGACCA    60

GCACACACTT GATGTGGAGG ATACCGCGGA TGCCAGACAT CCAGCAGGTA CTTCGTGCCC   120

CTCGGATGCG GCGCTCCTCA GAGATACCGG GCTCCTCGCG GACGCTGCGC TCCTCTCAGA   180

TACTGTGCGC CCCACAAATG CCGCGCTCCC CACGGATGCT GCCTACCCTG CGGTTAATGT   240

TCGGGATCGC GAGGCCGCGT GGCCGCCTGC ACTGAACTTC TGTTCCCGCC ACCCAAAGCT   300

CTATGGCCTA GTCGCTTTGG TTTTGCTGCT TCTGATCGCC GCCTGTGTTC CTATCTTCAC   360

CCGCACCGAG CCTCGGCCAG CGCTCACAAT CACCACCTCG CCCAACCTGG GTACCCGAGA   420

GAATAATGCA GACCAGGTCA CCCCTGTTTC CCACATTGGC TGCCCCAACA CTACACAACA   480

GGGCTCTCCT GTGTTCGCCA AGCTACTGGC TAAAAACCAA GCATCGTTGT GCAATACAAC   540

TCTGAACTGG CACAGCCAAG ATGGAGCTGG GAGCTCATAC CTATCTCAAG GTCTGAGGTA   600

CGAAGAAGAC AAAAAGGAGT TGGTGGTAGA CAGTCCCGGG CTCTACTACG TATTTTTGGA   660

ACTGAAGCTC AGTCCAACAT TCACAAACAC AGGCCACAAG GTGCAGGGCT GGGTCTCTCT   720

TGTTTTGCAA GCAAAGCCTC AGGTAGATGA CTTTGACAAC TTGGCCCTGA CAGTGGAACT   780

GTTCCCTTGC TCCATGGAGA ACAAGTTAGT GGACCGTTCC TGGAGTCAAC TGTTGCTCCT   840

GAAGGCTGGC CACCGCCTCA GTGTGGGTCT GAGGGCTTAT CTGCATGGAG CCCAGGATGC   900

ATACAGAGAC TGGGAGCTGT CTTATCCCAA CACCACCAGC TTTGGACTCT TCTTGTGAA    960

ACCCGACAAC CCATGGGAAT GAGAACTATC CTTCTTGTGA CTCCTAGTTG CTAAGTCCTC  1020

AAGCTGCTAT GTTTTATGGG GTCTGAGCAG GGTCCCTTC CATGACTTTC TCTTGTCTTT   1080

AACTGGACTT GGTATTTATT CTGAGCATAG CTCAGACAAG ACTTTATATA ATTCACTAGA  1140

TAGCATTAGT AAACTGCTGG GCAGCTGCTA GATAAAAAAA AATTTCTAAA TCAAAGTTTA  1200

TATTTATATT AATATATAAA AATAAATGTG TTTGTAAAT                        1239
```

(2) INFORMATION FOR SEQ ID NO: 19:

(i) SEQUENCE CHARACTERISTICS:

(A) LENGTH:        606 base pairs
        (B) TYPE:          nucleic acid
        (C) STRANDEDNESS:  single
        (D) TOPOLOGY:      linear (xi) SEQUENCE DESCRIPTION: SEQ ID NO: 19:

ATGATCGAAA CATACAACCA AACTTCTCCC CGATCTGCGG CCACTGGACT GCCCATCAGC      60

ATGAAAATTT TTATGTATTT ACTTACTGTT TTTCTTATCA CCCAGATGAT TGGGTCAGCA     120

CTTTTTGCTG TGTATCGCTT CGCACAGGCT TTTGAAATGC AAAAAGGTGA TCAGAATCCT    180

CAAATTGCGG CACATGTCAT AAGTGAGGCC AGCAGTAAAA CAACATCTGT GTTACAGTGG    240

GCTGAAAAAG GATACTACAC CATGAGCAAC AACTTGGTAA CCCTGGAAAA TGGGAAACAG    300

CTGACCGTTA AAAGACAAGG ACTCTATTAT ATCTATGCCC AAGTCACCTT CTGTTCCAAT    360

CGGGAAGCTT CGAGTCAAGC TCCATTTATA GCCAGCCTCT GCCTAAAGTC CCCCGGTAGA    420

TTCGAGAGAA TCTTACTCAG AGCTGCAAAT ACCCACAGTT CCGCCAAACC TTGCGGGCAA    480

CAATCCATTC ACTTGGGAGG AGTATTTGAA TTGCAACCAG GTGCTTCGGT GTTTGTCAAT    540

GTGACTGATC AAGCCAAGT GAGCCATGGC ACTGGCTTCA CGTCCTTTGG CTTACTCAAA     600

CTCTGA                                                                606

(2) INFORMATION FOR SEQ ID NO: 20:

(i) SEQUENCE CHARACTERISTICS:
        (A) LENGTH:        783 base pairs
        (B) TYPE:          nucleic acid
        (C) STRANDEDNESS:  single
        (D) TOPOLOGY:      linear (xi) SEQUENCE DESCRIPTION: SEQ ID NO: 20:

ATGATCGAAA CATACAACCA AACTTCTCCC CGATCTGCGG CCACTGGACT GCCCATCAGC      60

ATGAAAATTT TTATGTATTT ACTTACTGTT TTTCTTATCA CCCAGATGAT TGGGTCAGCA     120

CTTTTTGCTG TGTATCTTCA TAGAAGATTG GATAAGGTCG AAGAGGAAGT AAACCTTCAT    180

GAAGATTTTG TATTCATAAA AAAGCTAAAG AGATGCAACA AAGGAGAAGG ATCTTTATCC    240

TTGCTGAACT GTGAGGAGAT GAGAAGGCAA TTTGAAGACC TTGTCAAGGA TATAACGTTA    300

AACAAAGAAG AGAAAAAAGA AAACAGCTTT GAAATGCAAA AAGGTGATCA GAATCCTCAA    360

ATTGCGGCAC ATGTCATAAG TGAGGCCAGC AGTAAAACAA CATCTGTGTT ACAGTGGGCT    420

GAAAAAGGAT ACTACACCAT GAGCAACAAC TTGGTAACCC TGGAAAATGG GAAACAGCTG    480

ACCGTTAAAA GACAAGGACT CTATTATATC TATGCCCAAG TCACCTTCTG TTCCAATCGG    540

GAAGCTTCGA GTCAAGCTCC ATTTATAGCC AGCCTCTGCC TAAAGTCCCC CGGTAGATTC    600

GAGAGAATCT TACTCAGAGC TGCAAATACC CACAGTTCCG CCAAACCTTG CGGGCAACAA    660

TCCATTCACT TGGAGGAGT ATTTGAATTG CAACCAGGTG CTTCGGTGTT TGTCAATGTG     720

ACTGATCCAA GCCAAGTGAG CCATGGCACT GGCTTCACGT CCTTTGGCTT ACTCAAACTC    780

TGA                                                                   783

(2) INFORMATION FOR SEQ ID NO: 21:

(i) SEQUENCE CHARACTERISTICS:
        (A) LENGTH:        558 base pairs
        (B) TYPE:          nucleic acid
        (C) STRANDEDNESS:  single
        (D) TOPOLOGY:      linear (xi) SEQUENCE DESCRIPTION: SEQ ID NO: 21:

-continued

| | |
|---|---|
| CTGCTGCACT TCGGGGTAAT CGGCCCCCAG AGGGAAGAGC AGTCCCCAGG TGGCCCCTCC | 60 |
| ATCAACAGCC CTCTGGTTCA AACACTCAGG TCCTCTTCTC AAGCCTCAAG TAACAAGCCG | 120 |
| GTAGCCCACG TTGTAGCCGA CATCAACTCT CCGGGGCAGC TCCGGTGGTG GGACTCGTAT | 180 |
| GCCAATGCCC TCATGGCCAA CGGTGTGAAG CTGGAAGACA CCAGCTGGT GGTGCCTGCT | 240 |
| GACGGGCTTT ACCTCATCTA CTCACAGGTC CTCTTCAGGG GCCAAGGCTG CCCTTCCACC | 300 |
| CCCTTGTTCC TCACCCACAC CATCAGCCGC ATTGCAGTCT CCTACCAGAC CAAGGTCAAC | 360 |
| ATCCTGTCTG CCATCAAGAG CCCTTGCCAC AGGGAGACCC CAGAGTGGGC TGAGGCCAAG | 420 |
| CCCTGGTACG AACCCATCTA CCAGGGAGGA GTCTTCCAGC TGGAGAAGGG AGATCGCCTC | 480 |
| AGTGCTGAGA TCAACCTGCC GGACTACCTG GACTATGCCG AGTCCGGGCA GGTCTACTTT | 540 |
| GGGATCATTG CCCTGTGA | 558 |

(2) INFORMATION FOR SEQ ID NO: 22:

(i) SEQUENCE CHARACTERISTICS:
        (A) LENGTH:        1783 base pairs
        (B) TYPE:          nucleic acid
        (C) STRANDEDNESS:  single
        (D) TOPOLOGY:     linear (xi) SEQUENCE DESCRIPTION: SEQ ID NO: 22:

| | |
|---|---|
| CAAGTCACAT GATCCAGGAT GCAGGGAAA ATCCTTCTTG AACAGAGCT GGGTACAGAA | 60 |
| CCGAATCAGA TGAGGAGAGA TAAGGTGTGA TGTGGGACAG ACTATATAAA GCATGGAGCC | 120 |
| AGGGCTGCAA CAAGCAGGCA GCTGTGGGGC TCCTTCCCCT GACCCAGCCA TGCAGGTGCA | 180 |
| GCCCGGCTCG GTAGCCAGCC CCTGGAGAAG CACGAGGCCC TGGAGAAGCA CAAGTCGCAG | 240 |
| CTACTTCTAC CTCAGCACCA CCGCACTGGT GTGCCTTGTT GTGGCAGTGG CGATCATTCT | 300 |
| GGTACTGGTA GTCCAGAAAA AGGACTCCAC TCCAAATACA ACTGAGAAGG CCCCCCTTAA | 360 |
| AGGAGGAAAT TGCTCAGAGG ATCTCTTCTG TACCCTGAAA AGTACTCCAT CCAAGAAGTC | 420 |
| ATGGGCCTAC CTCCAAGTGT CAAAGCATCT CAACAATACC AAACTGTCAT GGAACGAAGA | 480 |
| TGGCACCATC CACGGACTCA TATACCAGGA CGGGAACCTG ATAGTCCAAT TCCCTGGCTT | 540 |
| GTACTTCATC GTTTGCCAAC TGCAGTTCCT CGTGCAGTGC TCAAATCATT CTGTGGACCT | 600 |
| GACATTGCAG CTCCTCATCA ATTCCAAGAT CAAAAAGCAG ACGTTGGTAA CAGTGTGTGA | 660 |
| GTCTGGAGTT CAGAGTAAGA ACATCTACCA GAATCTCTCT CAGTTTTTGC TGCATTACTT | 720 |
| ACAGGTCAAC TCTACCATAT CAGTCAGGGT GGATAATTTC CAGTATGTGG ATACAAACAC | 780 |
| TTTCCCTCTT GATAATGTGC TATCCGTCTT CTTATATAGT AGCTCAGACT GAATAGTTGT | 840 |
| TCTTAACCTT TATGAAAATG CTGTCTACCA TACAGTACTT CATCTGTCCA ACATGGGCC | 900 |
| AAAGAAAATA TTAGGACAAC TCAAACTAAG CATGTGAGTT AGTGCACTTC TCTTTCTGTC | 960 |
| CTTTGGAAAA ATACAAACCC AGGATTTAGA AAGTGGAGTC TCCTTCAGAT GCACAAACAG | 1020 |
| GAAAGAATGT GATATGTGCA CAGAGACCTA CTTGGGCACT AGAAGGGGTG TGAGTTGTCC | 1080 |
| CAGTATAACC ACTAATTCAC TGACCTTGAG CCATTTTTCC TTCCCCCTGG AACTTGGGGT | 1140 |
| CTGAATCTGG AAAAGTAGGA GATGAGATTT ACATTTCCCC AATATTTTCT TCAACTCAGA | 1200 |
| AGACGAGACT GTGGAGCTGA GCTCCCTACA CAGATGAAGG CCTCCCATGG CATGAGGAAA | 1260 |
| ATGATGGTAC CAGTAATGTC TGTCTGACTG TCATCTCAGC AAGTCCTAAG GACTTCCATG | 1320 |
| CTGCCTTGTT GAAAGATACT CTAACCTCTT GTAATGGGCA AAGTGATCCT GTCTCTCACT | 1380 |
| GAGGGGAGTA GCTGCTGCCA TCTCCTGAGA CATACATGGA GACATTTTCT GCCCAAATTC | 1440 |

```
CATTCTGTGT GCAGTTTTTA AGTATTCCCC CAAAAGTTCT TGACAATGAG AACTTTGAAT    1500

GTGGGAAGAG CTTCTGGACA GCAAACATTA ACAGCTTCTC CTGACCAGAG AGACCATGCA    1560

AGCTTGGTCT TAGACCCATC AAGCTTGAGG TTTCTACATT GTGGGAGACA GACTTTTGAC    1620

AAACCATTTG AGTTGATGTC TGGGCCCCTG GGAGTTCTCC TTCAGTAAGG AGAGCAAGCC    1680

GTTCTAGTGC TGTGTCAGAG GATGGAGTAA AATAGACACT TTTCTGAAGG AAAGGAGAAC    1740

AAAGTTCCAG AAAAAGGCTA GAAAATGTTT AAAAAGAAAA AAA                      1783

(2) INFORMATION FOR SEQ ID NO: 23:

(i) SEQUENCE CHARACTERISTICS:
        (A) LENGTH:        1047 base pairs
        (B) TYPE:          nucleic acid
        (C) STRANDEDNESS:  single
        (D) TOPOLOGY:      linear (xi) SEQUENCE DESCRIPTION: SEQ ID NO: 23:

AGAGAGCGCT GGGAGCCGGA GGGGAGCGCA GCGAGTTTTG GCCAGTGGTC GTGCAGTCCA      60

AGGGGCTGGA TGGCATGCTG GACCCAAGCT CAGCTCAGCG TCCGGACCCA ATAACAGTTT     120

TACCAAGGGA GCAGCTTTCT ATCCTGGCCA CACTGAGGTG CATAGCGTAA TGTCCATGTT     180

GTTCTACACT CTGATCACAG CTTTTCTGAT CGGCATACAG GCGGAACCAC ACTCAGAGAG     240

CAATGTCCCT GCAGGACACA CCATCCCCCA AGTCCACTGG ACTAAACTTC AGCATTCCCT     300

TGACACTGCC CTTCGCAGAG CCCGCAGCGC CCCGGCAGCG GCGATAGCTG CACGCGTGGC     360

GGGGCAGACC CGCAACATTA CTGTGGACCC CAGGCTGTTT AAAAAGCGGC GACTCCGTTC     420

ACCCCGTGTG CTGTTTAGCA CCCAGCCTCC CCGTGAAGCT GCAGACACTC AGGATCTGGA     480

CTTCGAGGTC GGTGGTGCTG CCCCCTTCAA CAGGACTCAC AGGAGCAAGC GGTCATCATC     540

CCATCCCATC TTCCACAGGG GCGAATTCTC GGTGTGTGAC AGTGTCAGCG TGTGGGTTGG     600

GGATAAGACC ACCGCCACAG ACATCAAGGG CAAGGAGGTG ATGGTGTTGG AGAGGTGAA     660

CATTAACAAC AGTGTATTCA AACAGTACTT TTTTGAGACC AAGTGCCGGG ACCCAAATCC     720

CGTTGACAGC GGGTGCCGGG GCATTGACTC AAAGCACTGG AACTCATATT GTACCACGAC     780

TCACACCTTT GTCAAGGCGC TGACCATGGA TGGCAAGCAG GCTGCCTGGC GGTTTATCCG     840

GATAGATACG GCCTGTGTGT GTGTGCTCAG CAGGAAGGCT GTGAGAAGAG CCTGACCTGC     900

CGACACGCTC CCTCCCCCTG CCCCTTCTAC ACTCTCCTGG GCCCCTCCCT ACCTCAACCT     960

GTAAATTATT TTAAATTATA AGGACTGCAT GGTAATTTAT AGTTTATACA GTTTTAAAGA    1020

ATCATTATTT ATTAAATTTT TGGAAGC                                        1047

(2) INFORMATION FOR SEQ ID NO: 24:

(i) SEQUENCE CHARACTERISTICS:
        (A) LENGTH:        1176 base pairs
        (B) TYPE:          nucleic acid
        (C) STRANDEDNESS:  single
        (D) TOPOLOGY:      linear (xi) SEQUENCE DESCRIPTION: SEQ ID NO: 24:

GAGCGCCTGG AGCCGGAGGG GAGCGCATCG AGTGACTTTG GAGCTGGCCT TATATTTGGA      60

TCTCCCGGGC AGCTTTTTGG AAACTCCTAG TGAACATGCT GTGCCTCAAG CCAGTGAAAT     120

TAGGCTCCCT GGAGGTGGGA CACGGGCAGC ATGGTGGAGT TTTGGCCTGT GGTCGTGCAG     180

TCCAGGGGGC TGGATGGCAT GCTGGACCCA AGCTCACCTC AGTGTCTGGG CCCAATAAAG     240

GTTTTGCCAA GGACGCAGCT TTCTATACTG GCCGCAGTGA GGTGCATAGC GTAATGTCCA     300
```

```
TGTTGTTCTA CACTCTGATC ACTGCGTTTT TGATCGGCGT ACAGGCAGAA CCGTACACAG    360

ATAGCAATGT CCCAGAAGGA GACTCTGTCC CTGAAGCCCA CTGGACTAAA CTTCAGCATT    420

CCCTTGACAC AGCCCTCCGC AGAGCCCGCA GTGCCCCTAC TGCACCAATA GCTGCCCGAG    480

TGACAGGGCA GACCCGCAAC ATCACTGTAG ACCCCAGACT GTTTAAGAAA CGGAGACTCC    540

ACTCACCCCG TGTGCTGTTC AGCACCCAGC CTCCACCCAC CTCTTCAGAC ACTCTGGATC    600

TAGACTTCCA GGCCCATGGT ACAATCCCTT TCAACAGGAC TCACCGGAGC AAGCGCTCAT    660

CCACCCACCC AGTCTTCCAC ATGGGGAGT TCTCAGTGTG TGACAGTGTC AGTGTGTGGG     720

TTGGAGATAA GACCACAGCC ACAGACATCA AGGGCAAGGA GGTGACAGTG CTGGCCGAGG    780

TGAACATTAA CAACAGTGTA TTCAGACAGT ACTTTTTTGA GACCAAGTGC CGAGCCTCCA    840

ATCCTGTTGA GAGTGGGTGC CGGGGCATCG ACTCCAAACA CTGGAACTCA TACTGCACCA    900

CGACTCACAC CTTCGTCAAG GCGTTGACAA CAGATGAGAA GCAGGCTGCC TGGAGGTTCA    960

TCCGGATAGA CACAGCCTGT GTGTGTGTGC TCAGCAGGAA GGCTACAAGA AGAGGCTGAC   1020

TTGCCTGCAG CCCCCTTCCC CACCTGCCCC CTCCACACTC TCTTGGGCCC CTCCCTACCT   1080

CAGCCTGTAA ATTATTTTAA ATTATAAGGA CTGCATGATA ATTTATCGTT TATACAATTT   1140

TAAAGACATT ATTTATTAAA TTTTCAAAGC ATCCTG                             1176

(2) INFORMATION FOR SEQ ID NO:  25:

(i) SEQUENCE CHARACTERISTICS:
        (A) LENGTH:         1623 base pairs
        (B) TYPE:           nucleic acid
        (C) STRANDEDNESS:   single
        (D) TOPOLOGY:       linear (xi) SEQUENCE DESCRIPTION: SEQ ID NO:  25:

TCAGAGTCCT GTCCTTGACA CTTCAGTCTC CACAAGACTG AGAGGAGGAA ACCCTTTCCT     60

GGGGCTGGGT GCCATGCAGC AGCCCGTGAA TTACCCATGT CCCCAGATCT ACTGGGTAGA    120

CAGCAGTGCC ACTTCTCCTT GGGCTCCTCC AGGGTCAGTT TTTTCTTGTC CATCCTCTGG    180

GCCTAGAGGG CCAGGACAAA GGAGACCACC GCCTCCACCA CCACCTCCAT CACCACTACC    240

ACCGCCTTCC CAACCACCCC CGCTGCCTCC ACTAAGCCCT CTAAAGAAGA AGGACAACAT    300

AGAGCTGTGG CTACCGGTGA TATTTTTCAT GGTGCTGGTG GCTCTGGTTG GAATGGGGTT    360

AGGAATGTAT CAACTCTTTC ATCTACAGAA GGAACTGGCA GAACTCCGTG AGTTCACCAA    420

CCACAGCCTT AGAGTATCAT CTTTTGAAAA GCAAATAGCC AACCCCAGCA CACCCTCTGA    480

AACCAAAAAG CCAAGGAGTG TGGCCCACTT AACAGGGAAC CCCCGCTCAA GGTCCATCCC    540

TCTGGAATGG GAAGACACAT ATGGAACTGC TTTGATCTCT GGAGTGAAGT ATAAGAAAGG    600

CGGCCTTGTG ATCAATGAGG CTGGGTTGTA CTTCGTATAT TCCAAAGTAT ACTTCCGGGG    660

TCAGTCTTGC AACAGCCAGC CCCTAAGCCA CAAGGTCTAT ATGAGGAACT TAAGTATCC     720

TGGGGATCTG GTGCTAATGG AGGAGAAGAA GTTGAATTAC TGCACTACTG GCCAGATATG    780

GGCCCACAGC AGCTACCTAG GGGCAGTATT TAATCTTACC GTTGCTGACC ATTTATATGT    840

CAACATATCT CAACTCTCTC TGATCAATTT TGAGGAATCT AAGACCTTTT TGGCTTATA     900

TAAGCTTTAA AGGAAAAAGC ATTTTAGAAT GATCTATTAT TCTTTATCAT GGATGCCAGG    960

AATATTGTCT TCAATGAGAG TCTTCTTAAG ACCAATTGAG CCACAAAGAC CACAAGGTCC   1020

AACAGGTCAG CTACCCTTCA TTTTCTAGAG GTCCATGGAG TGGTCCTTAA TGCCTGCATC   1080

ATGAGCCAGA TGGGAAGAAG ACTGTTCCTG AGGAACATAA AGTTTTGGGC TGCTGTGTGG   1140
```

```
CAATGCAGAG GCAAAGAGAA GGAACTGTCT GATGTTAAAT GGCCAAGAGC ATTTTAGCCA   1200

TTGAAGAAAA AAAAAACCTT TAAACTCACC TTCCAGGGTG GGTCTACTTG CTACCTCACA   1260

GGAGGCCGTC TTTTAGACAC ATGGTTGTGG TATGACTATA CAAGGGTGAG AAAGGATGCT   1320

AGGTTTCATG GATAAGCTAG AGACTGAAAA AAGCCAGTGT CCCATTGGCA TCATCTTTAT   1380

TTTTAACTGA TGTTTTCTGA GCCCACCTTT GATGCTAACA GAGAAATAAG AGGGGTGTTT   1440

GAGGCACAAG TCATTCTCTA CATAGCATGT GTACCTCCAG TGCAATGATG TCTGTGTGTG   1500

TTTTTATGTA TGAGAGTAGA GCGATTCTAA AGAGTCACAT GAGTACAACG CGTACATTAC   1560

GGAGTACATA TTAGAAACGT ATGTGTTACA TTTGATGCTA GAATATCTGA ATGTTTCTTG   1620

CTA                                                               1623

(2) INFORMATION FOR SEQ ID NO:  26:

(i) SEQUENCE CHARACTERISTICS:
        (A) LENGTH:          28 base pairs
        (B) TYPE:            nucleic acid
        (C) STRANDEDNESS:    single
        (D) TOPOLOGY:        linear (xi) SEQUENCE DESCRIPTION: SEQ ID NO:  26:

GTTAAGCTTT TCAGTCAGCA TGATAGAA                                     28

(2) INFORMATION FOR SEQ ID NO:  27:

(i) SEQUENCE CHARACTERISTICS:
        (A) LENGTH:          27 base pairs
        (B) TYPE:            nucleic acid
        (C) STRANDEDNESS:    single
        (D) TOPOLOGY:        linear (xi) SEQUENCE DESCRIPTION: SEQ ID NO:  27:

GTTTCTAGAT CAGAGTTTGA GTAAGCC                                      27

(2) INFORMATION FOR SEQ ID NO:  28:

(i) SEQUENCE CHARACTERISTICS:
        (A) LENGTH:          30 base pairs
        (B) TYPE:            nucleic acid
        (C) STRANDEDNESS:    single
        (D) TOPOLOGY:        linear (xi) SEQUENCE DESCRIPTION: SEQ ID NO:  28:

CCAAGACTAG TTAACACAGC ATGATCGAAA                                   30

(2) INFORMATION FOR SEQ ID NO:  29:

(i) SEQUENCE CHARACTERISTICS:
        (A) LENGTH:          30 base pairs
        (B) TYPE:            nucleic acid
        (C) STRANDEDNESS:    single
        (D) TOPOLOGY:        linear (xi) SEQUENCE DESCRIPTION: SEQ ID NO:  29:

CCAATGCGGC CGCACTCAGA ATTCAACCTG                                   30

(2) INFORMATION FOR SEQ ID NO:  30:

(i) SEQUENCE CHARACTERISTICS:
        (A) LENGTH:          972 base pairs
        (B) TYPE:            nucleic acid
        (C) STRANDEDNESS:    single
        (D) TOPOLOGY:        linear
```

(xi) SEQUENCE DESCRIPTION: SEQ ID NO: 30:

```
TCTAGACTCA GGACTGAGAA GAAGTAAAAC CGTTTGCTGG GGCTGGCCTG ACTCACCAGC      60

TGCCATGCAG CAGCCCTTCA ATTACCCATA TCCCCAGATC TACTGGGTGG ACAGCAGTGC     120

CAGCTCTCCC TGGGCCCCTC CAGGCACAGT TCTTCCCTGT CCAACCTCTG TGCCCAGAAG     180

GCCTGGTCAA AGGAGGCCAC CACCACCACC GCCACCGCCA CCACTACCAC CTCCGCCGCC     240

GCCGCCACCA CTGCCTCCAC TACCGCTGCC ACCCCTGAAG AAGAGAGGGA ACCACAGCAC     300

AGGCCTGTGT CTCCTTGTGA TGTTTTTCAT GGTTCTGGTT GCCTTGGTAG GATTGGGCCT     360

GGGGATGTTT CAGCTCTTCC ACCTACAGAA GGAGCTGGCA GAACTCCGAG AGTCTACCAG     420

CCAGATGCAC ACAGCATCAT CTTTGGAGAA GCAAATAGGC CACCCAGTC CACCCCCTGA      480

AAAAAAGGAG CTGAGGAAAG TGGCCCATTT AACAGGCAAG TCCAACTCAA GGTCCATGCC     540

TCTGGAATGG GAAGACACCT ATGGAATTGT CCTGCTTTCT GGAGTGAAGT ATAAGAAGGG     600

TGGCCTTGTG ATCAATGAAA CTGGGCTGTA CTTTGTATAT TCCAAAGTAT ACTTCCGGGG     660

TCAATCTTGC AACAACCTGC CCCTGAGCCA CAAGGTCTAC ATGAGGAACT CTAAGTATCC     720

CCAGGATCTG GTGATGATGG AGGGGAAGAT GATGAGCTAC TGCACTACTG GGCAGATGTG     780

GGCCCGCAGC AGCTACCTGG GGGCAGTGTT CAATCTTACC AGTGCTGATC ATTTATATGT     840

CAACGTATCT GAGCTCTCTC TGGTCAATTT TGAGGAATCT CAGACGTTTT TCGGCTTATA     900

TAAGCTCTAA GAGAAGCACT TTGGGATTCT TTCCATTATG ATTCTTTGTT ACAGGCACCG     960

AGATGTTCTA GA                                                         972
```

(2) INFORMATION FOR SEQ ID NO: 31:

(i) SEQUENCE CHARACTERISTICS:
        (A) LENGTH:        885 base pairs
        (B) TYPE:          nucleic acid
        (C) STRANDEDNESS:  single
        (D) TOPOLOGY:     linear (xi) SEQUENCE DESCRIPTION: SEQ ID NO: 31:

```
ATGCAGCAGC CCATGAATTA CCCATGTCCC CAGATCTTCT GGGTAGACAG CAGTGCCACT      60

TCATCTTGGG CTCCTCCAGG GTCAGTTTTT CCCTGTCCAT CTTGTGGGCC TAGAGGGCCG     120

GACCAAAGGA GACCGCCACC TCCACCACCA CCTGTGTCAC CACTACCACC GCCATCACAA     180

CCACTCCCAC TGCCGCCACT GACCCCTCTA AGAAGAAGG ACCACAACAC AAATCTGTGG      240

CTACCGGTGG TATTTTTCAT GGTTCTGGTG GCTCTGGTTG GAATGGGATT AGGAATGTAT     300

CAGCTCTTCC ACCTGCAGAA GGAACTGGCA GAACTCCGTG AGTTCACCAA CCAAAGCCTT     360

AAAGTATCAT CTTTTGAAAA GCAAATAGCC AACCCCAGTA CACCCTCTGA AAAAAAGAG      420

CCGAGGAGTG TGGCCCATTT AACAGGGAAC CCCCACTCAA GGTCCATCCC TCTGGAATGG     480

GAAGACACAT ATGGAACCGC TCTGATCTCT GGAGTGAAGT ATAAGAAAGG TGGCCTTGTG     540

ATCAACGAAG CTGGGTTGTA CTTCGTATAT TCCAAAGTAT ACTTCCGGGG TCAGTCTTGC     600

AACAACCAGC CCCTAAACCA CAAGGTCTAT ATGAGGAACT CTAAGTATCC TGGGGATCTG     660

GTGCTAATGG AGGAGAAGAG GTTGAACTAC TGCACTACTG GACAGATATG GCCCACAGC      720

AGCTACCTGG GGGCAGTATT CAATCTTACC AGTGCTGACC ATTTATATGT CAACATATCT     780

CAACTCTCTC TGATCAATTT TGAGGAATCT AAGACCTTTT TCGGCTTGTA TAAGCTTTAA     840

AAGAAAAAGC ATTTTAAAAT GATCTACTAT TCTTTATCAT GGGCA                     885
```

```
(2) INFORMATION FOR SEQ ID NO: 32:

(i) SEQUENCE CHARACTERISTICS:
        (A) LENGTH:         29 base pairs
        (B) TYPE:           nucleic acid
        (C) STRANDEDNESS:   single
        (D) TOPOLOGY:       linear (xi) SEQUENCE DESCRIPTION: SEQ ID NO: 32:

CTTAAGCTTC TACAGGACTG AGAAGAAGT                                          29

(2) INFORMATION FOR SEQ ID NO: 33:

(i) SEQUENCE CHARACTERISTICS:
        (A) LENGTH:         30 base pairs
        (B) TYPE:           nucleic acid
        (C) STRANDEDNESS:   single
        (D) TOPOLOGY:       linear (xi) SEQUENCE DESCRIPTION: SEQ ID NO: 33:

CTTGAATTCC AACATTCTCG GTGCCTGTAA                                         30

(2) INFORMATION FOR SEQ ID NO: 34:

(i) SEQUENCE CHARACTERISTICS:
        (A) LENGTH:         27 base pairs
        (B) TYPE:           nucleic acid
        (C) STRANDEDNESS:   single
        (D) TOPOLOGY:       linear (xi) SEQUENCE DESCRIPTION: SEQ ID NO: 34:

TCAGGATCCA CAAGGCTGTG AGAAGGA                                            27

(2) INFORMATION FOR SEQ ID NO: 35:

(i) SEQUENCE CHARACTERISTICS:
        (A) LENGTH:         26 base pairs
        (B) TYPE:           nucleic acid
        (C) STRANDEDNESS:   single
        (D) TOPOLOGY:       linear (xi) SEQUENCE DESCRIPTION: SEQ ID NO: 35:

CTTGTCTAGA CCTGGTGCCC ATGATA                                             26

(2) INFORMATION FOR SEQ ID NO: 36:

(i) SEQUENCE CHARACTERISTICS:
        (A) LENGTH:         680 base pairs
        (B) TYPE:           nucleic acid
        (C) STRANDEDNESS:   single
        (D) TOPOLOGY:       linear (xi) SEQUENCE DESCRIPTION: SEQ ID NO: 36:

ATGCCGGAGG AAGGTCGCCC TTGCCCCTGG GTTCGCTGGA GCGGGACCGC GTTCCAGCGC         60

CAATGGCCAT GGCTGCTGCT GGTGGTGTTT ATTACTGTGT TTTGCTGTTG GTTTCATTGT        120

AGCGGACTAC TCAGTAAGCA GCAACAGAGG CTGCTGGAGC ACCCTGAGCC GCACACAGCT        180

GAGTTACAGC TGAATCTCAC AGTTCCTCGG AAGGACCCCA CACTGCGCTG GGAGCAGGC         240

CCAGCCTTGG GAAGGTCCTT CACACACGGA CCAGAGCTGG AGGAGGGCCA TCTGCGTATC        300

CATCAAGATG GCCTCTACAG GCTGCATATC CAGGTGACAC TGGCCAACTG CTCTTCCCCA        360

GGCAGCACCC TGCAGCACAG GGCCACCCTG GCTGTGGGCA TCTGCTCCCC CGCTGCGCAC        420

GGCATCAGCT TGCTGCGTGG GCGCTTTGGA CAGGACTGTA CAGTGGCATT ACAGCGCCTG        480

ACATACCTGG TCCACGGAGA TGTCCTCTGT ACCAACCTCA CCCTGCCTCT GCTGCCGTCC        540
```

| | |
|---|---|
| CGCAACGCTG ATGAGACCTT CTTTGGAGTT CAGTGGATAT GCCCTTGACC ACAACTCCAG | 600 |
| GATGACTTGT GAATATTTTT TTTCTTTTCA AGTTCTACGT ATTTATAAAT GTATATAGTA | 660 |
| CACATAAAAA AAAAAAAAAA | 680 |

(2) INFORMATION FOR SEQ ID NO: 37:

(i) SEQUENCE CHARACTERISTICS:
        (A) LENGTH:        846 base pairs
        (B) TYPE:          nucleic acid
        (C) STRANDEDNESS:  single
        (D) TOPOLOGY:     linear (xi) SEQUENCE DESCRIPTION: SEQ ID NO: 37:

| | |
|---|---|
| ATGCAGCAGC CCTTCAATTA CCCATATCCC CAGATCTACT GGGTGGACAG CAGTGCCAGC | 60 |
| TCTCCCTGGG CCCCTCCAGG CACAGTTCTT CCCTGTCCAA CCTCTGTGCC CAGAAGGCCT | 120 |
| GGTCAAAGGA GGCCACCACC ACCACCGCCA CCGCCACCAC TACCACCTCC GCCGCCGCCG | 180 |
| CCACCACTGC CTCCACTACC GCTGCCACCC CTGAAGAAGA GAGGGAACCA CAGCACAGGC | 240 |
| CTGTGTCTCC TTGTGATGTT TTTCATGGTT CTGGTTGCCT TGGTAGGATT GGGCCTGGGG | 300 |
| ATGTTTCAGC TCTTCCACCT GCAGAAGGAA CTGGCAGAAC TCCGTGAGTT CACCAACCAA | 360 |
| AGCCTTAAAG TATCATCTTT TGAAAAGCAA ATAGGCCACC CCAGTCCACC CCCTGAAAAA | 420 |
| AAGGAGCTGA GGAAAGTGGC CCATTTAACA GGCAAGTCCA ACTCAAGGTC CATGCCTCTG | 480 |
| GAATGGGAAG ACACCTATGG AATTGTCCTG CTTTCTGGAG TGAAGTATAA GAAGGGTGGC | 540 |
| CTTGTGATCA ATGAAACTGG GCTGTACTTT GTATATTCCA AAGTATACTT CCGGGGTCAA | 600 |
| TCTTGCAACA ACCTGCCCCT GAGCCACAAG GTCTACATGA GGAACTCTAA GTATCCCCAG | 660 |
| GATCTGGTGA TGATGGAGGG GAAGATGATG AGCTACTGCA CTACTGGGCA GATGTGGGCC | 720 |
| CGCAGCAGCT ACCTGGGGGC AGTGTTCAAT CTTACCAGTG CTGATCATTT ATATGTCAAC | 780 |
| GTATCTGAGC TCTCTCTGGT CAATTTTGAG GAATCTCAGA CGTTTTTCGG CTTATATAAG | 840 |
| CTCTAA | 846 |

(2) INFORMATION FOR SEQ ID NO: 38:

(i) SEQUENCE CHARACTERISTICS:
        (A) LENGTH:        786 base pairs
        (B) TYPE:          nucleic acid
        (C) STRANDEDNESS:  single
        (D) TOPOLOGY:     linear (xi) SEQUENCE DESCRIPTION: SEQ ID NO: 38:

| | |
|---|---|
| ATGCAGCAGC CCTTCAATTA CCCATATCCC CAGATCTACT GGGTGGACAG CAGTGCCAGC | 60 |
| TCTCCCTGGG CCCCTCCAGG CACAGTTCTT CCCTGTCCAA CCTCTGTGCC CAGAAGGCCT | 120 |
| GGTCAAAGGA GGCCACCACC ACCACCGCCA CCGCCACCAC TACCACCTCC GCCGCCGCCG | 180 |
| CCACCACTGC CTCCACTACC GCTGCCACCC CTGAAGAAGA GAGGGAACCA CAGCACAGGC | 240 |
| CTGTGTCTCC TTGTGATGTT TTTCATGGTT CTGGTTGCCT TGGTAGGATT GGGCCTGGGG | 300 |
| ATGTTTCAGC TCTTCCGCTT CGCACAGGCT ATAGGCCACC CCAGTCCACC CCCTGAAAAA | 360 |
| AAGGAGCTGA GGAAAGTGGC CCATTTAACA GGCAAGTCCA ACTCAAGGTC CATGCCTCTG | 420 |
| GAATGGGAAG ACACCTATGG AATTGTCCTG CTTTCTGGAG TGAAGTATAA GAAGGGTGGC | 480 |
| CTTGTGATCA ATGAAACTGG GCTGTACTTT GTATATTCCA AAGTATACTT CCGGGGTCAA | 540 |
| TCTTGCAACA ACCTGCCCCT GAGCCACAAG GTCTACATGA GGAACTCTAA GTATCCCCAG | 600 |

```
GATCTGGTGA TGATGGAGGG GAAGATGATG AGCTACTGCA CTACTGGGCA GATGTGGGCC      660

CGCAGCAGCT ACCTGGGGGC AGTGTTCAAT CTTACCAGTG CTGATCATTT ATATGTCAAC      720

GTATCTGAGC TCTCTCTGGT CAATTTTGAG GAATCTCAGA CGTTTTTCGG CTTATATAAG      780

CTCTAA                                                                 786

(2) INFORMATION FOR SEQ ID NO: 39:

(i) SEQUENCE CHARACTERISTICS:
        (A) LENGTH:             864 base pairs
        (B) TYPE:               nucleic acid
        (C) STRANDEDNESS:       single
        (D) TOPOLOGY:           linear (xi) SEQUENCE DESCRIPTION: SEQ ID NO: 39:

ATGCAGCAGC CCTTCAATTA CCCATATCCC CAGATCTACT GGGTGGACAG CAGTGCCAGC       60

TCTCCCTGGG CCCCTCCAGG CACAGTTCTT CCCTGTCCAA CCTCTGTGCC AGAAGGCCT       120

GGTCAAAGGA GGCCACCACC ACCACCGCCA CCGCCACCAC TACCACCTCC GCCGCCGCCG      180

CCACCACTGC CTCCACTACC GCTGCCACCC CTGAAGAAGA GAGGGAACCA CAGCACAGGC      240

CTGTGTCTCC TTGTGATGTT TTTCATGGTT CTGGTTGCCT TGGTAGGATT GGGCCTGGGG      300

ATGTTTCAGC TCTTCCAATC CTCCATCCTC CCCTATGCCG GAGGAGGGTT CGGGCTGCTC      360

GGTGCGGCGC AGGCCCTATG GGTGCGTCCT GCGGCCATCC TCAATCCTAT AGGCCACCCC      420

AGTCCACCCC CTGAAAAAAA GGAGCTGAGG AAAGTGGCCC ATTTAACAGG CAAGTCCAAC      480

TCAAGGTCCA TGCCTCTGGA ATGGGAAGAC ACCTATGGAA TTGTCCTGCT TTCTGGAGTG      540

AAGTATAAGA AGGGTGGCCT TGTGATCAAT GAAACTGGGC TGTACTTTGT ATATTCCAAA      600

GTATACTTCC GGGGTCAATC TTGCAACAAC CTGCCCCTGA GCCACAAGGT CTACATGAGG      660

AACTCTAAGT ATCCCCAGGA TCTGGTGATG ATGGAGGGGA AGATGATGAG CTACTGCACT      720

ACTGGGCAGA TGTGGGCCCG CAGCAGCTAC CTGGGGCAG TGTTCAATCT TACCAGTGCT      780

GATCATTTAT ATGTCAACGT ATCTGAGCTC TCTCTGGTCA ATTTTGAGGA ATCTCAGACG      840

TTTTTCGGCT TATATAAGCT CTAA                                            864

(2) INFORMATION FOR SEQ ID NO: 40:

(i) SEQUENCE CHARACTERISTICS:
        (A) LENGTH:             828 base pairs
        (B) TYPE:               nucleic acid
        (C) STRANDEDNESS:       single
        (D) TOPOLOGY:           linear (xi) SEQUENCE DESCRIPTION: SEQ ID NO: 40:

ATGCAGCAGC CCTTCAATTA CCCATATCCC CAGATCTACT GGGTGGACAG CAGTGCCAGC       60

TCTCCCTGGG CCCCTCCAGG CACAGTTCTT CCCTGTCCAA CCTCTGTGCC AGAAGGCCT       120

GGTCAAAGGA GGCCACCACC ACCACCGCCA CCGCCACCAC TACCACCTCC GCCGCCGCCG      180

CCACCACTGC CTCCACTACC GCTGCCACCC CTGAAGAAGA GAGGGAACCA CAGCACAGGC      240

CTGTGTCTCC TTGTGATGTT TTTCATGGTT CTGGTTGCCT TGGTAGGATT GGGCCTGGGG      300

ATGTTTCAGC TCTTCCACCT ACAGCGAGAG TCTACCAGCC AGATGCACAC AGCATCATCT      360

TTGGAGAAGC AAATAGGCCA CCCCAGTCCA CCCCCTGAAA AAAGGAGCT GAGGAAAGTG      420

GCCCATTTAA CAGGCAAGTC CAACTCAAGG TCCATGCCTC TGGAATGGGA AGACACCTAT      480

GGAATTGTCC TGCTTTCTGG AGTGAAGTAT AAGAAGGGTG GCCTTGTGAT CAATGAAACT      540

GGGCTGTACT TTGTATATTC CAAAGTATAC TTCCGGGGTC AATCTTGCAA CAACCTGCCC      600
```

| | | |
|---|---|---|
| CTGAGCCACA AGGTCTACAT GAGGAACTCT AAGTATCCCC AGGATCTGGT GATGATGGAG | 660 |
| GGGAAGATGA TGAGCTACTG CACTACTGGG CAGATGTGGG CCCGCAGCAG CTACCTGGGG | 720 |
| GCAGTGTTCA ATCTTACCAG TGCTGATCAT TTATATGTCA ACGTATCTGA GCTCTCTCTG | 780 |
| GTCAATTTTG AGGAATCTCA GACGTTTTTC GGCTTATATA AGCTCTAA | 828 |

(2) INFORMATION FOR SEQ ID NO: 41:

(i) SEQUENCE CHARACTERISTICS:
        (A) LENGTH:        846 base pairs
        (B) TYPE:          nucleic acid
        (C) STRANDEDNESS:  single
        (D) TOPOLOGY:     linear (xi) SEQUENCE DESCRIPTION: SEQ ID NO: 41:

| | | |
|---|---|---|
| ATGGCTATGA TGGAGGTCCA GGGGGGACCC AGCCTGGGAC AGACCTGCGT GCTGATCGTG | 60 |
| ATCTTCACAG TGCTCCTGCA GTCTCTCTGT GTGGCTGTAA CTTACGTGTA CTTTACCAAC | 120 |
| GAGCTGAAGC AGATGCAGGA CAAGTACTCC AAAAGTGGCA TTGCTTGTTT CTTAAAAGAA | 180 |
| GATGACAGTT ATTGGGACCC CAATGACGAA GAGAGTATGA ACAGCCCCTG CTGGCAAGTC | 240 |
| AAGTGGCAAC TCCGTCAGCT CGTTAGAAAG ATGATTTTGA GAACCTCTGA GGAAACCATT | 300 |
| TCTACAGTTC AAGAAAAGCA ACAAAATATT TCTCCCCTAG TGAGAGAAAG AGGTCCTCAG | 360 |
| AGAGTAGCAG CTCACATAAC TGGGACCAGA GGAAGAAGCA ACACATTGTC TTCTCCAAAC | 420 |
| TCCAAGAATG AAAAGGCTCT GGGCCGCAAA ATAAACTCCT GGGAATCATC AAGGAGTGGG | 480 |
| CATTCATTCC TGAGCAACTT GCACTTGAGG AATGGTGAAC TGGTCATCCA TGAAAAAGGG | 540 |
| TTTTACTACA TCTATTCCCA AACATACTTT CGATTTCAGG AGGAAATAAA AGAAAACACA | 600 |
| AAGAACGACA AACAAATGGT CCAATATATT TACAAATACA CAAGTTATCC TGACCCTATA | 660 |
| TTGTTGATGA AAAGTGCTAG AAATAGTTGT TGGTCTAAAG ATGCAGAATA TGGACTCTAT | 720 |
| TCCATCTATC AAGGGGGAAT ATTTGAGCTT AAGGAAAATG ACAGAATTTT TGTTTCTGTA | 780 |
| ACAAATGAGC ACTTGATAGA CATGGACCAT GAAGCCAGTT TTTTCGGGGC CTTTTTAGTT | 840 |
| GGCTAA | 846 |

(2) INFORMATION FOR SEQ ID NO: 42:

(i) SEQUENCE CHARACTERISTICS:
        (A) LENGTH:        876 base pairs
        (B) TYPE:          nucleic acid
        (C) STRANDEDNESS:  single
        (D) TOPOLOGY:     linear (xi) SEQUENCE DESCRIPTION: SEQ ID NO: 42:

| | | |
|---|---|---|
| ATGCCTTCCT CAGGGGCCCT GAAGGACCTC AGCTTCAGTC AGCACTTCAG GATGATGGTG | 60 |
| ATTTGCATAG TGCTCCTGCA GGTGCTCCTG CAGGCTGTGT CTGTGGCTGT GACTTACATG | 120 |
| TACTTCACCA ACGAGATGAA GCAGCTGCAG GACAATTACT CCAAAATTGG ACTAGCTTGC | 180 |
| TTCTCAAAGA CGGATGAGGA TTTCTGGGAC TCCACTGATG GAGAGATCTT GAACAGACCC | 240 |
| TGCTTGCAGG TTAAGAGGCA ACTGTATCAG CTCATTGAAG AGGTGACTTT GAGAACCTTT | 300 |
| CAGGACACCA TTTCTACAGT TCCAGAAAAG CAGCTAAGTA CTCCTCCCTT GCCCAGAGGT | 360 |
| GGAAGACCTC AGAAAGTGGC AGCTCACATT ACTGGGATCA CTCGGAGAAG CAACTCAGCT | 420 |
| TTAATTCCAA TCTCCAAGGA TGGAAAGACC TTAGGCCAGA AGATTGAATC CTGGGAGTCC | 480 |
| TCTCGGAAAG GGCATTCATT TCTCAACCAC GTGCTCTTTA GGAATGGAGA GCTGGTCATC | 540 |

```
GAGCAGGAGG GCCTGTATTA CATCTATTCC CAAACATACT TCCGATTTCA GGAAGCTGAA      600

GACGCTTCCA AGATGGTCTC AAAGGACAAG GTGAGAACCA AACAGCTGGT GCAGTACATC      660

TACAAGTACA CCAGCTATCC GGATCCCATA GTGCTCATGA AGAGCGCCAG AAACAGCTGT      720

TGGTCCAGAG ATGCCGAGTA CGGACTGTAC TCCATCTATC AGGGAGGATT GTTCGAGCTA      780

AAAAAAAATG ACAGGATTTT TGTTTCTGTG ACAAATGAAC ATTTGATGGA CCTGGATCAA      840

GAAGCCAGCT TCTTTGGAGC CTTTTTAATT AACTAA                                876

(2) INFORMATION FOR SEQ ID NO: 43:

(i) SEQUENCE CHARACTERISTICS:
        (A) LENGTH:         720 base pairs
        (B) TYPE:           nucleic acid
        (C) STRANDEDNESS:   single
        (D) TOPOLOGY:       linear (xi) SEQUENCE DESCRIPTION: SEQ ID NO: 43:

ATGGAGCCAG GGCTGCAACA AGCAGGCAGC TGTGGGGCTC CTTCCCCTGA CCCAGCCATG       60

CAGGTGCAGC CCGGCTCGGT AGCCAGCCCC TGGAGAAGCA CGAGGCCCTG GAGAAGCACA      120

AGTCGCAGCT ACTTCTACCT CAGCACCACC GCACTGGTGT GCCTTGTTGT GGCAGTGGCG      180

ATCATTCTGG TACTGGTAGT CCAGAAAAAG GACTCCACTC CAAATACAAC TGAGAAGGCC      240

CCCCTTAAAG GAGGAAATTG CTCAGAGGAT CTCTTCTGTA CCCTGAAAAG TACTCCATCC      300

AAGAAGTCAT GGGCCTACCT CCAAGTGTCA AAGCATCTCA ACAATACCAA ACTGTCATGG      360

AACGAAGATG GCACCATCCA CGGACTCATA TACCAGGACG GGAACCTGAT AGTCCAATTC      420

CCTGGCTTGT ACTTCATCGT TTGCCAACTG CAGTTCCTCG TGCAGTGCTC AAATCATTCT      480

GTGGACCTGA CATTGCAGCT CCTCATCAAT TCCAAGATCA AAAAGCAGAC GTTGGTAACA      540

GTGTGTGAGT CTGGAGTTCA GAGTAAGAAC ATCTACCAGA ATCTCTCTCA GTTTTTGCTG      600

CATTACTTAC AGGTCAACTC TACCATATCA GTCAGGGTGG ATAATTTCCA GTATGTGGAT      660

ACAAACACTT TCCCTCTTGA TAATGTGCTA TCCGTCTTCT TATATAGTAG CTCAGACTGA      720

(2) INFORMATION FOR SEQ ID NO: 44:

(i) SEQUENCE CHARACTERISTICS:
        (A) LENGTH:         930 base pairs
        (B) TYPE:           nucleic acid
        (C) STRANDEDNESS:   single
        (D) TOPOLOGY:       linear (xi) SEQUENCE DESCRIPTION: SEQ ID NO: 44:

ATGGACCAGC ACACACTTGA TGTGGAGGAT ACCGCGGATG CCAGACATCC AGCAGGTACT       60

TCGTGCCCCT CGGATGCGGC GCTCCTCAGA GATACCGGGC TCCTCGCGGA CGCTGCGCTC      120

CTCTCAGATA CTGTGCGCCC CACAAATGCC GCGCTCCCCA CGGATGCTGC CTACCCTGCG      180

GTTAATGTTC GGGATCGCGA GGCCGCGTGG CCGCCTGCAC TGAACTTCTG TTCCCGCCAC      240

CCAAAGCTCT ATGGCCTAGT CGCTTTGGTT TTGCTGCTTC TGATCGCCGC CTGTGTTCCT      300

ATCTTCACCC GCACCGAGCC TCGGCCAGCG CTCACAATCA CCACCTCGCC CAACCTGGGT      360

ACCCGAGAGA ATAATGCAGA CCAGGTCACC CCTGTTTCCC ACATTGGCTG CCCCAACACT      420

ACACAACAGG GCTCTCCTGT GTTCGCCAAG CTACTGGCTA AAAACCAAGC ATCGTTGTGC      480

AATACAACTC TGAACTGGCA CAGCCAAGAT GGAGCTGGGA GCTCATACCT ATCTCAAGGT      540

CTGAGGTACG AAGAAGACAA AAAGGAGTTG GTGGTAGACA GTCCCGGGCT CTACTACGTA      600

TTTTTGGAAC TGAAGCTCAG TCCAACATTC ACAAACACAG GCCACAAGGT GCAGGGCTGG      660
```

―continued

```
GTCTCTCTTG TTTTGCAAGC AAAGCCTCAG GTAGATGACT TTGACAACTT GGCCCTGACA      720

GTGGAACTGT TCCCTTGCTC CATGGAGAAC AAGTTAGTGG ACCGTTCCTG GAGTCAACTG      780

TTGCTCCTGA AGGCTGGCCA CCGCCTCAGT GTGGGTCTGA GGGCTTATCT GCATGGAGCC      840

CAGGATGCAT ACAGAGACTG GGAGCTGTCT TATCCCAACA CCACCAGCTT TGGACTCTTT      900

CTTGTGAAAC CCGACAACCC ATGGGAATGA                                       930
```

METHODS OF EXPRESSING CHIMERIC MOUSE AND HUMAN CD40 LIGAND IN HUMAN CD40+ CELLS

RELATED APPLICATION

This application claims priority to Kipps et al., NOVEL EXPRESSION VECTORS CONTAINING ACCESSORY MOLECULE LIGAND GENES AND THEIR USE FOR IMMUNOMODULATION AND TREATMENT OF MALIGNANCIES, United States Provisional Application No. 60/032145, filed Dec. 9, 1996, which is incorporated herein by reference including drawings.

STATEMENT OF GOVERNMENT SUPPORT

This invention was made with support from the federal government under NIH Grant No. CA49870. The Government has certain rights in the invention

TECHNICAL FIELD OF THE INVENTION

The present invention relates to novel expression vectors containing genes which encode an accessory molecule ligand and the use of those vectors for immunomodulation, improved vaccination protocols and the treatment of malignancies and autoimmune diseases. More particularly, this invention provides expression vectors and methods for treating various neoplastic or malignant cells, and expression vectors and methods for treating autoimmune Disease. This invention also contemplates the production and expression of accessory molecule ligands with greater stability and enhanced function.

BACKGROUND THE INVENTION

Leukemias, lymphomas, carcinomas and other malignancies are well known and described in, e.g., *Harrison's Principles of Internal Medicine*, Wilson et al., eds., McGraw-Hill, New York, pp. 1599–1612. These malignancies appear to have somehow escaped the immune system surveillance mechanisms that eliminate rapidly and continuously proliferating cells. The exact mechanism by which these malignancies escape the immune system surveillance is not known.

Some of these malignant immune system cells are malignant antigen presenting cells which do not function properly within the immune cascade. For example, neoplastic B cells cannot induce even weak allogeneic or autologous mixed lymphocyte reactions in vitro. Further evidence that malignancies survive due to the failure of the immune surveillance mechanism includes the increased frequency of such malignancies in immunocompromised individuals, such as allograft recipients and those receiving long-term immunosuppressant therapy. Further, the frequency of these malignancies is :increased in patients having Acquired Immune Deficiency Syndrome (AIDS) and patients with primary immune deficiency syndromes, such as X-linked lymphoproliferative syndrome or Wiscott-Aldrich Syndrome (Thomas et al., *Adv. cancer Res.* 57:329, 1991).

The immune system normally functions to eliminate malignant cells by recognizing the malignant cells as foreign cells and clearing those cells from the body. An immune reaction depends on both the immune system's antibody response and on the cellular immune response within a patient. More specifically, the cellular immune response which acts to recognize the malignant cells as foreign requires a number of different cells of the immune system and the interaction between those cells. An immune reaction begins with a T lymphocyte (T cell) which has on its cell surface the T cell receptor. The T cell also has the ability to express on its surface various accessory molecules which, interact with accessory molecules on the B lymphocyte (B cell). When the T cell receptor of the T cell specifically binds to a foreign antigen, such as a malignant cell, it becomes activated and expresses the accessory molecule ligand, CD40 ligand on its cell surface. The accessory cell molecule ligand is only present on the activated T cells for a short period of time and is rapidly removed from the cell surface. After the accessory cell molecule ligand is removed from the surface of the activated T cell, its ability to bind to B cells via the accessory molecule ligand is destroyed.

When present on the surface of an activated T cell, the accessory cell ligand can specifically bind to the accessory cell molecule present on the B cell. This specific T-B cell interaction causes the B and T cell to express costimulatory surface accessory molecule and cytokines which result in an immune activation which lead to cytolytic T cells which specifically kill and remove the malignant cell from the body.

The interaction with an activated T cell is not solely limited to B cells but rather can be carried out by any cell which is able to present antigen to the T cell (an antigen presenting cell). These cells include B lymphocyte, macrophages, dendritic cells, monocytes, Langerhans cells, interdigitating cells, follicular dendritic cells or Kupffer cells. These cells all are known to have various accessory molecules on the cell surface which allow them to interact with other cells of the immune system. For example, these antigen presenting cells all have the accessory molecule CD40 on their cell surface. The presence of these accessory molecules allows these antigen presenting cells to specifically bind to complimentary accessory molecule ligand and thus directly interact with other immune cells.

A large number of accessory molecule ligands are members of the tumor necrosis factor superfamily. (Fanslow et al., *Sem. Immun.*, 6:267–268 (1994). The genes for a number of these accessory molecule ligands have been cloned and identified. These accessory molecule ligand genes encode accessory molecules which all have the configuration of Type II membrane proteins and exhibit varying degrees of homology with other accessory molecule ligand genes. For example, the accessory molecule ligand genes encoding both murine CD40 ligand and human CD40 ligand have been isolated. See, Armitage et al., *Nature*. 357:80–82 (1992) and Hollenbaugh et al., *EMBO J.*, 11:4313–4321 (1992).

CD40 and its ligand, CD40 ligand are critical components of a normal immune response. CD40 mediated signals induce immune lymphocytes to proliferate and differentiate and become potent antigen presenting cells. Malignant or neoplastic B cells are poor antigen presenter cells and are unable to stimulate a vigorous allogeneic mixed lymphocyte reaction. Successful cross linking of CD40 molecules on immune cells results in a strong allogeneic mixed lymphocyte reaction suggesting a strong immune reaction. Various soluble CD40 ligands or antibodies specific for CD40 have been used to potentially cross link CD40. These soluble CD40 ligands and CD40-specific antibodies are not optimal for cross linking the CD40 molecules on antigen presenting cells and do not work as effectively as CD40 ligand expressed on a cell membrane to produce strong stimulation of antigen presenting cells. These methods are also difficult to implement because large amounts of CD40 ligand constructs or antibodies must be isolated which is difficult and time-consuming work. Other strategies to utilize CD40 ligand in solution or as a membrane bound molecule including transformation of fibroblasts with CD40 ligand to produce cultured cells which are then used to present antigen are not amenable to in vivo human clinical protocols.

CD95 (Fas) interaction with its ligand (Fas-ligand, or FasL) functions to limit the duration of the immune response and/or life-span of activated lymphocytes. Apoptosis induced by Pas-FasL binding serves to clear activated self-reactive lymphocytes. Problems caused by altering this pathway have been demonstrated in animals with defects in Fas<->Fas-ligand interactions. Mice having mutations, which inactivate CD95 or FasL, develop numerous disorders including autoimmune pathology resembling that seen in patients with rheumatoid arthritis (RA) or systemic lupus. Zhang, et al., in *J. Clin. Invest*. 100:1951–1957 (1997) show that injection of FasL-expressing virus, into the joints of mice with collagen-induced-arthritis; results in apoptosis of synovial cells and relief of arthritis symptoms. Expression of Fas ligand allows clearance of activated cells which play a role in the pathogenesis of autoimmune disease. Therefore, a gene therapy strategy for introducing Pan into the joints of rheumatoid arthritis patients could function to improve disease pathology by leading to destruction of the infiltrating mononuclear cells.

Administration of soluble accessory molecules and accessory molecule ligands has been shown to trigger or to be associated with adverse physiological effects. For example, treatment of mice, having wild-type CD40-0 receptor expression, with soluble CD40L-CD8 fusion protein resulted in a pulmonary inflammatory response. This was not observed in mice in which the gene for the CD40 receptor had been knocked out. These experiments, described in Wiley, J. A. et al., *Journal of Immunology* 158:2932–2938 (1997), support in vitro data which suggest that CD40 ligation can result in inflammatory responses.

Direct administration of purified recombinant soluble Tumor Necrosis Factor (either α or β) results in shock and tissue injury, as described in Tracey, K. J., and A. Cerami, *Annu. Rev. Med*. 45:491–503 (1994). Within minutes after acute intravenous or intra-arterial administration of TNF, a syndrome of shock, tissue injury, capillary leakage syndrome, hypoxia, pulmonary edema, and multiple organ failure associated with a high mortality ensues. Chronic low dose of TNF causes anorexia, weight loss, dehydration and depletion of whole-body protein and lipid.

Soluble Fas ligand and receptor have also been shown to be associated with tissue damage and other adverse effects, CD95, the Fas receptor, is a mediator of apoptosis. Fas ligand induces apoptosis by binding to Fas receptor. As shown in Galle, P. R., et al., *J. Exo. Med*. 182:1223–1230 (1995) administering an agonistic anti-Fas antibody resulted in liver damage to mice. Mice injected intraperitoneally with the agonistic antibody died within several hours, and analyses revealed that severe liver damage by apoptosis was the most likely cause of death.

The role of soluble Fas ligand (FasL), in the pathogenesis of systemic tissue injury in aggressive lymphoma is described in Sato, K. et al., *British Journal of Haematology*, 94:379–382 (1996). The findings presented in this report indicate that soluble FasL is directly associated with the pathogenesis of liver injury and pancytopenia.

CD27, the receptor for the accessory molecule ligand, CD70, was shown, in a report written by van Oers, et al., in *Blood* 82:3430–3436 (1993), to be associated with B cell malignancies.

The above findings all contraindicate the administration of soluble accessory molecule ligands, highlighting the need for therapies that increase the levels of these molecules without resulting in an elevation of their soluble forms.

Despite the wealth of information regarding accessory molecule ligand genes and their expression on the surface of various immune cells, the exact mechanism by which the accessory molecule ligand genes are regulated on antigen presenting cells is not yet known. Without specific knowledge of the regulation of expression of accessory molecule ligand genes on these antigen presenting cells, altering the immune response by varying expression of an accessory molecule ligand gene has to date not been possible. Without any specific knowledge as to how to regulate the expression of an accessory molecule ligand gene on an antigen presenting cell, it is not possible to alter the immune response towards malignant cells. Thus, there was a need for a method of increasing the expression of an accessory molecule ligand gene on normal and malignant cells including antigen presenting cells.

Further, without the ability to regulate the expression of accessory molecule ligands, it is not possible to alter the immune clearance of these cells.

SUMMARY OF THE INVENTION

The present invention fills these needs by providing novel expression vectors containing accessory molecule ligand genes and methods for introducing those genes into normal and malignant antigen presenting cells thereby allowing the alteration of an immune response, the treatment of autoimmune diseases and the treatment of various neoplasias. This invention provides vectors, including gene therapy vectors which contain accessory molecule ligand genes. These vectors also contain the additional genetic elements, such as promoters, enhancers, polyadenylation signals (3' ends), which allow that vector to be successfully placed within the cell and to direct the expression of the accessory molecule ligand gene in a cell. Such gene therapy vectors are capable of transforming animal cells directly and thereby introducing the accessory molecule ligand gene into the cells of that animal in a form which can be utilized to produce accessory molecule ligands within that cell.

In other aspects of the present invention, the function of an accessory molecule ligand is modified by altering the half life of the molecule on the cell surface or by changing the level of expression of that molecule on the cell surface. In preferred embodiments, the present invention provides accessory molecule ligands which are modified to improve the stability of such accessory molecule ligands on the cell surface. Such increased stability may be accomplished using any of the disclosed methods of molecules described in this application, including chimeric molecules and molecules into which mutations have been introduced at least one location. The present invention also contemplates increasing the expression of such a molecule.

The present invention also provides gene therapy vectors containing the accessory molecule ligand genes which are chimeric in that portions of the gene are derived from two separate accessory molecule ligands which may or may not be from different species. The accessory molecule ligand genes of the present invention include genes which encode molecules of the tumor necrosis factor (TNF) family. The molecules which make up the TNF family include $TNF_\alpha TNF_\beta$, CD40 ligand, Fas ligand, CD70, CD30 ligand, 41BB ligand (4-1BBL), nerve growth factor and TNF-related apoptosis inducing ligand (TRAIL). In some embodiments of the present invention, the chimeric accessory molecule ligand genes of the present invention contain at least a portion of a murine accessory molecule ligand gene together with portions of accessory molecule ligand genes derived from either mouse, humans or other species. Some preferred embodiments of the present invention utilize murine CD40 ligand genes and chimeric CD40 ligand genes containing at least a segment of the murine CD40 ligand gene together with at least a segment of the human CD40 ligand gene. The present invention contemplates chimeric accessory molecule ligand genes wherein segments from the accessory molecule ligand gene of one species have been interchanged with segments from a second accessory molecule ligand gene which may optionally be from a different species. For example, in one preferred embodiment, the murine CD40 ligand gene transmembrane and cytoplasmic domains have been attached to the extracellular domains of human CD40 ligand gene.

The present invention contemplates gene therapy vectors which are capable of directly infecting the human, mammal, insect, or other cell. The use of such gene therapy vectors greatly simplifies inserting an accessory molecule ligand gene into those cells. The contemplated gene therapy vectors may be used in vivo or in vitro to infect the desired cell and are particularly useful for infecting malignant cells to effect sustained high-level expression of a physiologic ligand.

The present invention also contemplates animal, mammal, and human cells containing a gene therapy vector which includes an accessory molecule ligand gene and sufficient genetic information to express that accessory molecule ligand within that cell. In preferred embodiments, the present invention also contemplates human neoplastic antigen presenting cells which contain the gene therapy vectors of the present invention or contain an accessory molecule ligand gene together with a promoter and 3' end region.

The present invention also contemplates human cells and human neoplastic cells containing a gene therapy vector which includes a chimeric accessory molecule ligand gene. The present invention also contemplates bacterial cells or animal cells containing accessory molecule ligand genes, chimeric accessory molecule ligand genes, murine accessory molecule ligand genes, human accessory molecule ligand genes, the gene therapy vectors of the present invention, the vectors of the present invention, and a chimeric accessory molecule ligand gene together with a heterologous promoter, enhancer or polyadenylation sequence.

The present invention also contemplates methods of altering immune response within a human patient or the immunoreactivity of human cells in vivo by introducing a gene which encodes an accessory molecule ligand gene into the human cells so that that accessory molecule ligand is expressed on the surface of those human cells. This method includes the introduction of the accessory molecule ligand gene as part of a gene therapy vector or in association with a heterologous or native promoter, enhancer or polyadenylation signal. Some preferred embodiments of the present invention utilize introduction of Fas ligand genes and chimeric Fas ligand genes, constructed as contemplated above for CD40, into human cells to alter their immunoreactivity. The present invention also includes methods in which such accessory molecule ligand genes are inserted into cells which have the accessory molecule to which the accessory molecule ligand binds on the surface of the cell into which the accessory molecule ligand gene.

The present methods of altering immunoreactivity are applicable to all types of human, animal, and murine cells including human neoplastic cells such as human lymphomas, leukemias and other malignancies. In preferred embodiments, this method is used to introduce the gene encoding the accessory molecule ligand into potential antigen presenting cells of a human patient or cell which can stimulate bystanding antigen presenting cells. Such antigen presenting cells include monocytes, macrophages, B cells, Langerhans cells, interdigitating cells, follicular dendritic cells, Kupffer cells, and the like. The various antigen presenting cells may be present as part of a known malignancy in a human patient such as leukemias, lymphomas, acute monocytic leukemia (AML), chronic lymphocytic leukemia (CLL), acute myelomonocytic leukemia (AMML), chronic myelogenous or chronic myelomonocytic leukemia (CPML) and thus would include all tumors of any cell capable of presenting antigen to the human or animal immune system or are capable of stimulating bystanding antigen presenting cells. The present invention also contemplates modulating the immune system by introducing genes encoding an accessory molecule ligand gene of the present invention into any number of different cells found in a patient, including muscle cells, skin cells, stromal cells, connective tissue cells, fibroblasts and the like.

The present invention also contemplates methods of treating neoplasias in either a human patient or an animal patient. In one preferred embodiment, the method comprises isolating the neoplastic cells from the human or animal patient and inserting into those isolated cells the gene which encodes the chimeric accessory molecule ligand or the accessory molecule ligand so that that molecule is expressed on the cell surface of those neoplastic cells or other somatic cells. The neoplastic cells are then infused back into the human or animal patient and may then participate in an enhanced immune response.

The present invention also contemplates the co-infection or co-introduction of the accessory molecule ligand gene together with a gene which encodes a tumor or carcinoma specific antigen. This combination of molecules are then expressed on the surface of the neoplastic cells and when those cells are introduced into the patient lead to the rapid immune response resulting in the destruction of those cells.

The present methods also include directly introducing the gene therapy vector or other vector carrying the accessory molecule ligand gene directly into the tumor or tumor bed of a patient. Upon entering the tumor bed of the patient, the gene therapy vector or other vector enter the cells present in the tumor or tumor bed and then express the accessory molecule ligand gene on the surface of those cells. These cells then are able to participate fully in the human immune or animal immune response.

The present invention also contemplates methods of augmenting an immune response to a vaccine. The present method of vaccinating an animal against a predetermined organism or antigen by administering to that animal a vaccine which has a genetic vector containing an accessory molecule ligand gene. Other embodiments of the present invention include vaccinating an animal by administering two separate genetic vectors, one containing the antigens from the organism to which immunity is desired by isolating the cells of the target animal and contacting with those cells a vector encoding at least one antigen from a predetermined organism so that the antigen is expressed by the cells and also contacting those cells with a different vector which expresses the accessory molecule ligand gene on the surface of the animal's antigen presenting cells. Together these two separate vectors produce a vaccination which is much stronger and of longer duration than is vaccination with antigen alone.

The present methods of vaccination are applicable to vaccinations designed to produce immunity against a virus, a cell, a bacteria, any protein or a fungus. The present methods are also applicable to immunization against various carcinomas and neoplasias. In these embodiments, the tumor antigen against which immunity is desired is introduced into the animal together with the genetic vector containing the accessory molecule ligand gene.

The present invention also contemplates methods of treating arthritis utilizing a gene therapy vector encoding an accessory molecule ligand. Of particular interest for use with arthritis is the Fas ligand molecule in which the expression of Fas ligand activity has been increased in the joint and/or the stability of the Fas ligand activity on cells within the joint enhanced. In other embodiments, the present invention contemplated methods of treating arthritis utilizing chimeric accessory molecule ligands and chimeric accessory molecule ligand genes. The present invention also contemplates both ex vivo therapy and in vivo therapy of arthritis utilizing the expression vectors of the present invention together with the Fas ligand and modified versions of that molecule including chimeric molecules.

BRIEF DESCRIPTION OF THE DRAWINGS

FIG. 1 is a diagram showing a number of accessory molecule ligand genes and Domains I–IV of those genes as deduced from sequence data.

FIG. 2 is a diagram showing example chimeric accessory molecule ligand genes. The domains derived from the murine accessory module are shown shaded.

FIG. 3 shows the amount of either mouse or human CD40 ligand found on the surface of Hela or CLL cells infected with gene therapy vectors containing the genes encoding these molecules. FIG. 3A shows uninfected Hela cells (shaded) and Hela cells infected with a gene therapy vector encoding murine CD40 ligand. FIG. 3B shows uninfected Hela cells (shaded) and Hela cells infected with a gene therapy vector encoding human CD40 ligand. FIG. 3C shows uninfected CLL cells (shaded) and CLL cells infected with a gene therapy vector encoding murine CD40 ligand. FIG. 3D shows uninfected CLL cells (shaded) and CLL cells infected with a gene therapy vector encoding human CD40 ligand.

FIG. 4 shows histograms of the increased expression of CD54 (FIG. 4B) and CD80 (FIG. 4D) on CLL cells into which a gene therapy vector containing the accessory molecule ligand gene (murine CD40 ligand gene) has been introduced. The shaded graph indicates control stain in FRCS analysis and the open graph indicates staining with monoclonal antibodies immunospecific for either CD54 (FIGS. 4A and 4B) or CD80 (FIGS. 4C and 4D).

FIG. 5 shows the cell proliferation as measured by $^3$H-TdR incorporation of allogeneic T cells in response to various stimulation regimes. The CLL cells containing a gene therapy vector expressing an accessory molecule ligand gene (the murine CD40 ligand gene) were introduced, stimulating allogeneic T cells to proliferate.

FIG. 6 shows the production of gamma interferon (IFNγ) by allogeneic T cells stimulated with CLL cells containing an accessory molecule ligand gene.

FIG. 7 shows the treatment of a neoplasia in an animal using a gene therapy vector containing an accessory molecule ligand gene of the present invention. The open squares show mice immunized with neoplastic cell not expressing an accessory molecule ligand of the present invention. Mice immunized with neoplastic cells expressing an accessory molecule ligand of the present invention are shown as the horizontal line at the top of the Figure and show no morbidity.

FIG. 8 a shows the production levels and stabilities of CD40 ligand and CD40 ligand transcript in CLL (upper graph) and normal blood mononuclear cells (lower graph).

FIG. 9 shows the time course of transgene expression in CLL B cells infected with the accessory molecule ligand (CD40 ligand). The MFIR (mean fluorescence intensity ratio), comparing the fluorescence intensity of CD19$^+$ CLL cells stained with PE-labeled CD40 ligand versus the same stained with a PE-labeled isotype control mAb at each time point, are represented by the closed circles connected by solid lines according to the scale provided on the left-hand ordinate.

FIG. 10 shows changes in surface antigen phenotype of CLL B cells infected with a gene therapy vector containing an accessory molecule ligand, CD40 ligand. Shaded histograms represent staining of uninfected CLL cells (thin lines) stained with nonspecific control antibody, open histograms drawn with thin lines represent uninfected CLL cells stained with FITC-conjugated specific mAb, and open histograms drawn with thick lines (labeled CD154-CLL) represent CLL cells infected with the accessory molecule ligand gene therapy vector and stained with FITC-conjugated specific mAb.

FIG. 11 shows levels of CD27 produced in CLL cells infected with a gene therapy vector containing an accessory molecule ligand. FIG. 11A shows that CD40L-infected CU (CD154-CLL) cells express reduced levels of surface CD27. Open histograms represent staining of non-infected CLL cells (thin lines) or infected CLL (thick lines) with FITC-conjugated αCD27 mAb, respectively. FIG. 11B shows production of soluble form of CD27 by CLL B cells.

FIG. 12 shows allogeneic T cell responses induced by CLL cells infected with a gene therapy vector containing an accessory molecule ligand (CD40 ligand, also called CD154). FIG. 12 A indicates the concentration of IFNγ in the supernatants after stimulation of allogeneic T cells with CLL cells containing the accessory molecule ligand. FIG. 12B shows cell proliferation, as assessed by incorporation of $^3$H-thymidine. FIGS. 12C and 12D show secondary allogeneic T cell responses induced by CLL containing the accessory molecule ligand.

FIG. 13 depicts autologous T cell responses induced by CLL B cells containing the accessory molecule ligand, CD40 ligand or CD154, and controls. FIG. 13A shows incorporation of $^3$H-thymidine by autologous T cells co-cultured with the CLL cells. FIG. 13B shows the levels of human IFNγ produced by autologous T cells co-cultured with the CLL cells. In FIG. 13C, the CTL activities of autologous T cells induced by CLL B cells containing the accessory molecule ligand are graphed.

FIG. 14 shows specificity of CTL for autologous CLL B cells. IFNγ concentration was assessed in the supernatants after 48 h of culture (FIG. 14A), and cytolytic activity was assessed at 3 h of culture (FIG. 14B). In FIG. 14C, mAb were added to the autologous leukemia target cells prior to the CTL assay.

FIG. 15 shows that intercellular stimulation plays a role in production of the phenotypic changes observed in CLL cells expressing the accessory molecule ligand. In FIG. 15A, the effect of culture density on the induced expression of CD54 and C080 following infection with a gene therapy vector containing the accessory molecule ligand (CD40 ligand, CD154) is shown. Shaded histograms represent staining of leukemia B cells with a FITC-conjugated isotype control mAb. open histograms represent CD154-CLL B cells, cultured at high or low density (indicated by arrows), and stained with a FITC-conjugated mAb specific for CD54 or CD80. FIG. 15 B shows inhibition of CD154-CLL cell activation by anti-CD154 mAb. FIGS. 15C and 15D depict expression of immune accessory molecules on bystander non-infected CLL B cells induced by CLL cells expressing the accessory molecule ligand. Shaded histograms represent staining with PE-conjugated isotype control mAb.

FIG. 16 shows that the vector encoding an accessory molecule ligand enhances immunization against β-gal in mice. FIG. 16A shows that mice that received intramuscular injections of the pCD40L vector produced significantly more antibodies to β-gal than did mice injected with either the non-modified pcDNA3 vector or pCD40L. FIG. 16B, ELISA analyses of serial dilutions of sera collected at d28, shows that mice co-injected with placZ and pCD40L had an eight-fold higher mean titer of anti-β-gal antibodies at: d28 than mice treated with placZ+pcDNA3.

FIG. 17 shows analysis of the IgG, and $IgG_{2a}$ immune responses to intramuscular plasmid DNA immunizations with and without a vector, pCD40L, encoding an accessory molecule ligand. $IgG_{2a}$ anti-β-gal antibodies predominated over IgG, subclass antibodies in the sera of mice injected with either placZ and pcDNA3 or placZ and pCD40L. In contrast, BALB/c mice injected with β-gal protein developed predominantly IgG, anti-β-gal antibodies, and no detectable IgG" anti-β-gal antibodies.

FIG. 18 shows the comparison between injection of mice with a vector, pCD40L, encoding an accessory molecule ligand, at the same and different sites as placZ. Adjuvant effect of pCD40L requires co-injection with placZ at the same site.

FIG. 19 shows that co-injection into dermis of a vector encoding an accessory molecule ligand, pCD40L, with placZ enhances the IgG anti-β-gal response in BALB/c mice.

FIG. 20 shows that a vector encoding an accessory molecule ligand, pCD40L, enhances the ability of placZ to induce CTL specific for syngeneic β-gal-expressing target cells. Splenocyte effector cells, taken from mice which had received injections of placZ and pCD40L, specifically lysed significantly more cells than did splenocytes from mice that received control injections.

FIG. 21 shows downmodulation of human CD40L, but not murine CD40L, in lung tumor cell lines that express CD40.

FIG. 22.

FIG. 23 shows the inhibition of Fas ligand expression by lymphocytes in the presence of RA synovial fluid.

FIG. 24 shows an outline for a clinical trial of an accessory molecule ligand (CD40L) gene therapy treatment for B cell CLL.

FIG. 25. FIG. 25 shows a sequence line-up of human Fas ligand with human Fas ligand in which Domain III is replaced by Domain III of murine Fas ligand. The top protein sequence is native human Fas ligand. Domain III is underlined with the dotted line. The double underline indicates a putative MMP cleavage site. The bottom protein sequence is that of chimeric human-mouse Fas ligand. Domain III of the mouse Fas ligand (underlined with dotted line) is substituted for Domain III of human Fas ligand. The numbers correspond to the amino acid sequence number using 1 for the start of the polypeptide sequence. The number of the first nucleotide base for the codon encoding the amino acid is 30 3×(n−1), where n is the amino acid sequence number.

FIG. 26. FIG. 26 shows a sequence line-up of human Fas ligand with human Fas ligand in which Domain III has been replaced with Domain III of human CD70. The top protein sequence is native human Fas ligand, and the bottom sequence is that of chimeric Fas ligand, in which Domain III of human CD70 has been substituted for Fas Domain III. Other markings are used similarly as in FIG. 25.

FIG. 27. FIG. 27 shows a sequence line-up of human Fas ligand with human Fas ligand in which Domain I has been replaced with Domain III of human C070. The top protein is native human Fas ligand, and the bottom protein sequence is that of chimeric Fas ligand, in which Domain III has been replaced with Domain I of human CD70. Other markings are used similarly as in FIG. 25.

FIG. 28. FIG. 28 shows the amino acids around and at known matrix metalloproteinase (MMP) cleavage sites, as described in Smith, M. M. et al., Journal of Biol. Chem. 270:6440–6449 (95) and Nagase, H., and G. H. Fields, Biopolymers (Peptide Science) 40:399–416 (96). The cleavage site is indicated with an arrow.

DETAILED DESCRIPTION OF THE INVENTION

Figure 1:
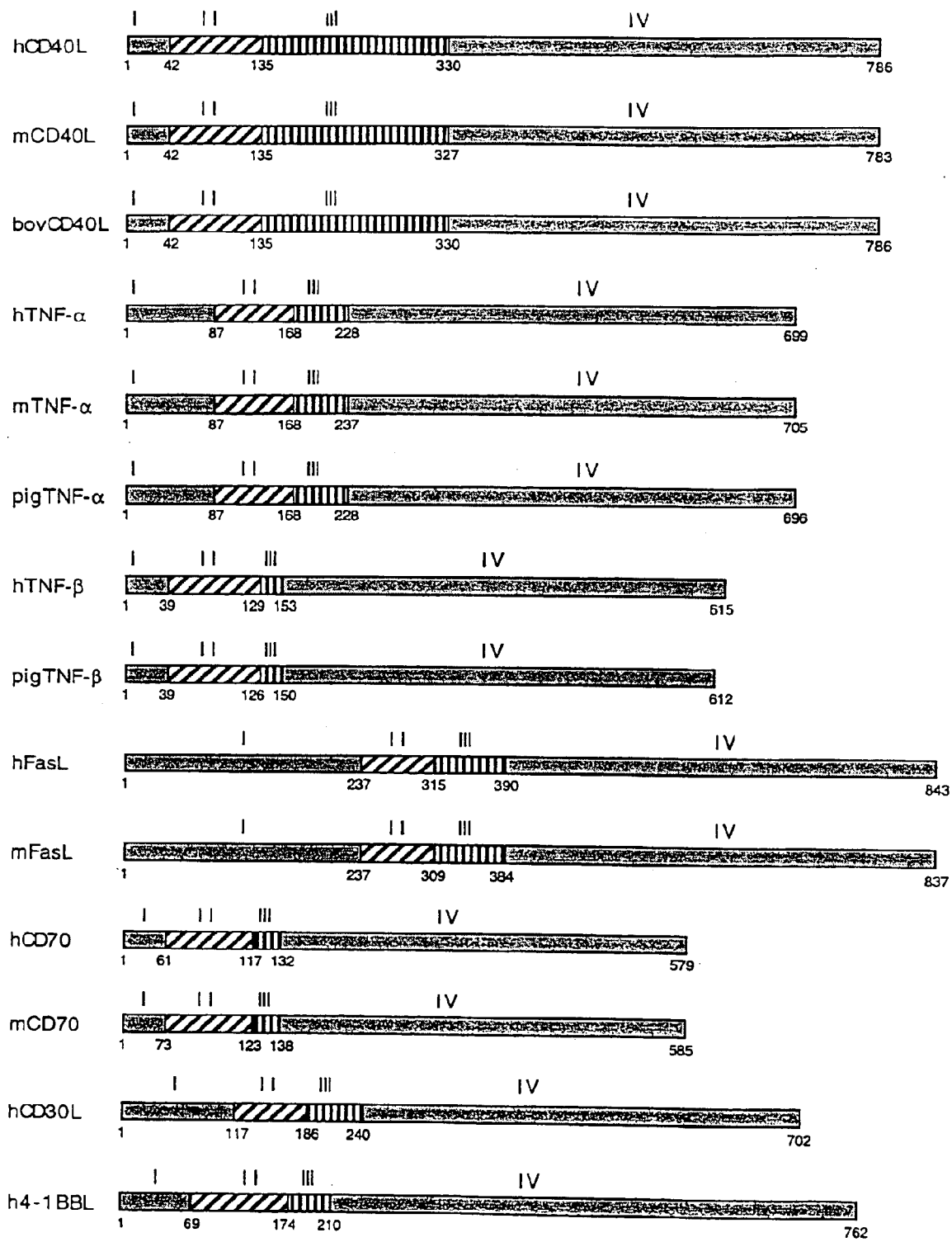
FIG. 1.

All references cited herein are hereby incorporated in their entirety by reference.

I. Definitions

An "accessory molecule ligand gene" is a gene which encodes all or part of an accessory molecule ligand. The gene comprises at least the nucleotide sequence required to encode the functional portion of an accessory molecule ligand. The gene may optionally include such genetic elements as promoters, enhancers and 3' ends. The accessory molecule ligand gene is derived from a ligand which is a member of the tumor necrosis factor (TNF) family, including CD40 ligand, Fas ligand, CD70, $TNF_\alpha$, $TNF_\beta$, CD30 ligand, 4-1BB ligand (4-1BBL), nerve growth factor and TNF-related apoptosis inducing ligand (TRAIL). As used herein, the term "accessory molecule ligand gene" includes chimeric accessory molecule ligand genes as defined below.

As used herein, the term "malignant cells or neoplastic cells," is defined to mean malignant or cancerous cells which are found in a human patient or an animal. Preferred types of malignant or neoplastic cells include any malignant antigen-presenting cell. In some preferred embodiments, these malignant antigen presenting cells have at least low levels of CD40 present on the cell surface.

As used herein, the term "neoplastic human cells" is defined to mean human cells which are neoplastic including but not limited to antigen presenting cells, any neoplastic cell which may function as an antigen presenting cell or function to facilitate antigen presentation, neoplastic monocytes, neoplastic macrophages, neoplastic B cells, neoplastic dendritic cells, neoplastic Langerhans cells, neoplastic interdigitating cells, neoplastic follicular dendritic cells, or neoplastic Kupffer cells and the like. The definition of neoplastic human cells includes those cells which are associated with neoplastic cells in the tumor bed of human patients. Typically, the neoplastic human cells are either leukemias, lymphomas, AML, ALL, AMML, CML, CMML, CLL other tumors of antigen presenting cells or breast, ovarian or lung neoplastic cells. It is also contemplated that the accessory molecule ligand genes or chimeric accessory molecule ligand genes of the present invention may be inserted into somatic cells. These somatic cells can be created by a, genetic engineering process which has introduced into those cells genes which encode molecules which render those cells capable of presenting antigen to the immune system.

As used herein, the term "chimeric gene" is defined to mean a gene in which part of the gene is derived from a second different gene and combined with the first gene so that at least a portion of each gene is present in the resulting chimeric gene. A gene may be chimeric if any portion of the sequence which encodes the resulting protein is derived from a second and different gene. Typical chimeric genes include genes in which specific functional domains from one gene have been transferred to a second gene and replace the analogous domains of that second gene. For example, the resulting chimeric gene may have one domain derived from a murine gene and several domains derived from a human gene. These domains may range in size from 5 amino acids to several hundred amino acids. Other examples of chimeric accessory molecule ligand genes include genes which contain nucleotides encoding amino acids not found in any naturally occurring accessory molecule ligand gene. Examples of chimeric genes and potential various combinations of domains are numerous and one of skill in the art will understand that no limit is placed on the amount of one gene that must be present: in a second gene to render it chimeric.

As used herein, the term "murine CD40 ligand gene" is defined to mean an accessory molecule ligand gene which is derived from a murine CD40 ligand gene. Examples of such murine CD40 ligand genes include the gene isolated by Armitage et al., *Nature*, 357:80–82 (1992) and other genes derived from murine origin which hybridize to the gene described by Armitage et al. under low stringency hybridization conditions.

As used herein, the tern "vector or genetic vector" is defined to mean a nucleic acid which is capable of replicating itself within an organism such as a bacterium or animal cell. Typical genetic vectors include the plasmids commonly used in recombinant DNA technology and-various viruses capable of replicating within bacterial or animal cells. Preferred types of genetic vectors includes plasmids, phages, viruses, retroviruses, and the like.

As used herein, the term "gene therapy vector" is defined to mean a genetic vector which is capable of directly infecting cells within an animal, such as a human patient. A number of gene therapy vectors have been described in the literature, and include, the gene therapy vector described in Cantwell et al., *Blood*, In Press (1996) entitled "Adenovirus Vector Infection of Chronic Lymphocytic Leukemia B Cells." Such vectors have been described for example by Woll, P. J. and I. R. Hart, *Ann. Oncol.*, 6 Suppl 1:73 (1995); Smith, K. T., A. J. Shepherd, J. E. Boyd, and G. M. Lees, *Gene Ther.*, 3:190 (1996); Cooper, M. J., *Semin, Oncol.*, 23:172 (1996); Shaughnessy, E., D. Lu, S. Chatterjee, and K. K. Wong, *Semin. Oncol.*, 23:159 (1996); Glorioso, J. C., N. A. DeLuca, and D. J. Fink, *Annu. Rev. Microbiol.*, 49:675 (1995); Flotte, T. R. and B. J. Carter., *Gene Ther.*, 2:357 (1995); Randrianarison-Jewtoukoff, V. and M. Perricaudet, *Biologicals.*, 23:145 (1995); Kohn, D. B., *Curr. Opin.* *Pediatr.*, 7:56 (1995); Vile, R. G. and S. J. Russell, *Br. Med. Bull.*, 51:12 (1995); Russell, S. J., Semin. Cancer Biol., 5:437 (1994); and Ali, M., N. R. Lemoine, and C. J. Ring, *Gene Ther.*, 1;367 (1994). All references cited herein are hereby incorporated by reference.

II. Genetic Vectors and Constructs Containing an Accessory Molecule Ligand Gene

A. Accessory Molecule Ligand Genes

In one embodiment of the present invention, preferred gene therapy vectors contain an accessory molecule ligand gene. This accessory molecule ligand gene may be derived from any source and may include molecules which are man-made and do not appear in nature. The present invention contemplates accessory molecule ligand genes which are derived from the genes encoding molecules within the tumor necrosis family (TNF) which includes the genes encoding: murine CD40 ligand, human CD40 ligand, Fas ligand, $TNF_\alpha$, $TNF_\beta$, CD30 ligand, 4-1BB ligand, nerve growth factor, CD70, TNF-related apoptosis inducing ligand (TRAIL) and chimeric accessory molecule ligands. The nucleotide sequence of one accessory molecule ligand, the sequence of at least one form of the murine CD40 ligand gene has been determined and is listed as SEQ ID N2. The present invention contemplates the use of any-accessory molecule ligand gene which is homologous to the sequence present in SEQ ID NO:2, and thus hybridizes to this sequence at low stringency hybridization conditions. One of skill in the art will understand that accessory molecule ligand genes, including murine CD40 ligand gene, useful in the present invention may be isolated from various different murine strains.

The nucleotide sequence of a human CD40 ligand gene has been determined and is shown as SEQ ID NO:1. The present invention contemplates the use of any accessory molecule ligand gene which is homologous to SEQ ID NO:1, and thus hybridizes to this sequence at low stringency conditions. One of ordinary skill in the art will understand that the accessory molecule ligand genes, including the human CD40 ligand genes, useful in the present invention, may vary depending on the individual from which the gene is isolated and such variations may prove useful in producing unique accessory molecule ligand genes. The present invention contemplates the use of the domains, subdomains, amino acid or nucleotide sequence of the human CD40 ligand and/or human CD40 ligand gene as part of a chimeric accessory molecule ligand or chimeric accessory molecule ligand gene.

The nucleotide sequence of a bovine CD90 ligand gene has been determined and is shown as SEQ ID NO: 8. The present invention contemplates the use of any accessory molecule ligand gene which is homologous to SEQ ID NO: 8, and thus hybridizes to the sequence at low stringency conditions. One of ordinary skill in the art will understand that the accessory molecule ligand genes, including the bovine CD40 ligand genes, may vary depending on the individual animal from which the gene is isolated and that such variations may prove useful in producing unique accessory molecule ligand genes.

The nucleotide sequence of human TNF, and human TNF, have been determined and are shown as SEQ ID NOS: 9 and 10, respectively. The present invention contemplates the use of any accessory molecule ligand gene which is homologous to either human $TNF_\alpha$ or human $TNF_\beta$ (SEQ ID NOS: 9 and 10, respectively), and thus hybridizes to these sequences at low stringency conditions. The accessory molecule ligand genes useful in the present invention, including the human TNF, and TNFD genes, may vary depending on the particular individual from which the gene has been isolated and these variations may prove useful in producing unique accessory molecule genes.

The nucleotide sequence of porcine $TNF_\alpha$ and $TNF_\beta$ have been determined and are shown as SEQ ID NO: 11. The present invention contemplates the use of any accessory molecule ligand gene which is homologous to either SEQ ID NO: 11, and thus would hybridize to these sequences at low stringency conditions. One of ordinary skill in the art will understand that the accessory molecule ligand genes, including the porcine $TNF_\alpha$ and $TNF_\beta$ genes, may vary depending on the particular animal from which the gene is isolated and that such variation may prove useful in producing unique accessory molecule genes.

The nucleotide sequence of a murine $TNF_\alpha$ gene has been determined and is shown as SEQ ID NO: 12. The present invention contemplates the use of any accessory molecule ligand gene which is homologous to SEQ ID NO: 12, and thus hybridizes to the sequence at low stringency conditions. One of ordinary skill in the art will understand that the accessory molecule ligand genes, including the murine TNF, gene may vary depending on the individual from which the gene is isolated and that these variations may prove useful in producing unique accessory molecule genes.

The nucleotide sequence of human Fas ligand and murine (C57BL/6) Fas ligand have been determined and are shown as SEQ ID NOS: 13 and 14, respectively. The nucleotide sequence of murine Balb/c Fas ligand is shown as SEQ ID NO: 31. The present invention contemplates the use of any accessory molecule ligand gene which is homologous to any of SEQ ID NOS: 13, 14, and 31, and thus hybridizes to the sequences at low stringency conditions. One of ordinary skill in the art will understand that the accessory molecule ligand genes, including the human Fas ligand or murine Fas ligand genes may vary depending on the particular individual or animal from which the gene is isolated and that such variations may prove useful in producing any accessory molecule genes.

The nucleotide sequence of a human CD70 gene has been determined and is shown as SEQ ID NO: 15. The murine CD70 gene sequence has also been determined, and is shown as SEQ ID NO: 36 and was described by Tesselaar et, al, *J. Immunol.* 159:4959–65 (1997). The present invention contemplates the use of any accessory molecule ligand gene which is homologous to SEQ ID NO:15 or 36, and thus hybridizes to this sequence at low stringency conditions. One of ordinary skill in the art will understand that the accessory molecule ligand genes, including the human CD70 gene may vary depending on the individual from which the gene is isolated and that these variations may prove useful in producing unique accessory molecule ligand genes.

The nucleotide sequence of human CD30 ligand gene has been determined and is shown as SEQ ID NO: 16. The present invention contemplates the use of any accessory molecule ligand gene which is homologous to SEQ ID NO: 16, and thus hybridizes to this sequence at low stringency conditions. One of ordinary skill in the art will understand that the accessory molecule ligand genes, including the human CD30 ligand gene, may vary depending on the individual from which the gene is isolated and that such variations may prove useful in producing unique accessory molecule ligand genes.

The present invention also contemplates variations and variants of the nucleotide sequences of the accessory molecule ligand genes provided herein which are caused by alternative splicing of the messenger RNA. This alternative splicing of the messenger RNA inserts additional nucleotide sequences which may encode one or more optional amino acid segments which in turn allows the accessory molecule ligand encoded to have additional properties or functions.

The nucleotide sequence of a human and mouse 4-1BBL have been determined and are shown as SEQ ID NOS: 17 and 18, respectively. The present invention contemplates the use of any accessory molecule ligand gene which is homologous to either SEQ ID NOS: 17 or 18, and thus hybridizes to these sequences at low stringency conditions. One of ordinary skill in the art will understand that accessory molecule ligand genes, including the human 4-1BBL gene may vary depending on the individual from which it is isolated and that such variations may prove useful in producing unique accessory molecule ligand genes.

The present invention also contemplates chimeric accessory molecules containing any domain, sub-domain portion, or amino acid sequence encoded by the following genes: bovine TNF-α (SEQ ID NO:21), murine CD40 ligand (SEQ ID NO: 1), human nerve growth factor-β (SEQ ID NO:23), murine nerve growth factor (SEQ ID NO: 24), rat Fas ligand (SEQ ID NO:25), human TNF-related apoptosis inducing ligand (TRAIL) (SEQ ID NO: 41, Genbank accession number U37518), murine TNF-related apoptosis inducing ligand (TRAIL) (SEQ ID NO: 42, Genbank accession number U37522), murine CD30-Ligand (SEQ ID NO: 43), human 4-1BBL (SEQ ID NO: 17), and murine 4-1BEL (SEQ ID NOS: 44 and 18). The present :invention also contemplates chimeric accessory molecules which utilize genes encoding amino acid sequences homologous to these sequences.

The present invention contemplates chimeric accessory molecule ligand genes which are comprised of a nucleotide segment derived from one accessory molecule ligand gene operatively linked to a nucleotide sequence derived from a different accessory molecule ligand gene or other gene.

For example, chimeric accessory molecule ligand genes are contemplated which are comprised of a segment of the murine CD40 ligand gene which has been operatively linked to at least one other additional gene segment derived from a different accessory molecule ligand gene. The size of the particular segment derived from the different accessory molecule ligand gene may vary from a nucleotide sequence encoding a few amino acids, a sub-domain of the accessory molecule ligand, a domain of the accessory molecule ligand or more than a domain of an accessory molecule ligand. Other chimeric accessory molecules of the present invention are comprised of an accessory molecule ligand gene into which nucleotides encoding an amino acid segment which is not found as part of a naturally occurring accessory molecule ligand have been inserted. This amino acid segment may be artificially created or derived from a protein found in nature. The chimeric accessory molecule ligand gene encodes a chimeric amino acid sequence and thus a chimeric accessory molecule ligand encoded may possess unique properties in addition to the properties found on the individual segments derived from the different accessory molecule ligand genes. The chimeric accessory molecule ligand gene may encode an accessory molecule ligand which has properties derived from the accessory molecule ligand used to construct the chimeric gene.

Each of the accessory molecule ligand genes which are a member of the tumor necrosis factor family have a similar secondary structure consisting of a number of domains. This domain structure includes a first domain which is encoded by the 5' region of the accessory molecule ligand gene. The second domain (Domain II) is the domain which contains the amino acids which span the cell membrane and is thus called the transmembrane domain. The third domain (Domain III) is the proximal extracellular domain and these amino acids are the amino acids which are found proximal to the cellular membrane. The fourth domain (Domain IV), is encoded by the 3' end of the accessory molecule ligand gene and has been called the distal extracellular domain. The distal extracellular domain (Domain IV) generally makes up the soluble form of the tumor necrosis factor family molecule. Based on the x-ray crystal structure of human TNF, the predicted secondary structure of the accessory molecule, CD40 ligand has been deduced together with the domain structure of these molecules by M. Peitsch and C. Jongeneel, *International Immunology*, 5:233–238 (1993). The secondary structures of the other members of the tumor necrosis factor family were deduced using computer analysis together with comparison to the human TNF and CD40 ligand domain structure. In Table I, the domain boundaries of a number of accessory molecule ligand genes is shown. A diagram of these domains for a number of these accessory cell molecule ligands is shown in FIG. 1. The assignments of the domain boundaries are approximate and one of ordinary skill in the art will understand that these boundaries may vary and yet still provide useful identification of domains.

TABLE I

DOMAIN STRUCTURE OF TUMOR NECROSIS FACTOR FAMILY MOLECULES*

|  | Domain I (Cytoplasmic) | Domain II (Transmembrane) | Domain III (Proximal Extracellular) | Domain IV (Distal Extracellular) |
|---|---|---|---|---|
| Human CD40 Ligand | 1–42 | 43–135 | 136–330 | 331–786 |
| Murine CD40 Ligand | 1–42 | 43–135 | 136–327 | 328–783 |
| Bovine CD40 Ligand | 1–42 | 43–135 | 136–330 | 331–786 |
| Human TNF-α | 1–87 | 88–168 | 169–228 | 229–699 |
| Murine TNF-α | 1–87 | 88–168 | 169–237 | 238–705 |
| Porcine TNF-α | 1–87 | 88–168 | 169–228 | 229–696 |
| Human TNF-β | 1–39 | 40–129 | 130–153 | 154–615 |
| Porcine TNF-β | 1–39 | 40–126 | 127–150 | 151–612 |
| Human Fas Ligand | 1–237 | 238–315 | 316–390 | 391–843 |
| Murine Fas Ligand | 1–237 | 238–309 | 310–384 | 385–837 |
| Human CD70 | 1–61 | 62–117 | 118–132 | 133–579 |
| Murine CD70 | 1–73 | 74–123 | 124–138 | 139–585 |
| Human CD30 Ligand | 1–117 | 118–186 | 187–240 | 241–702 |
| Murine CD30 Ligand | 1–135 | 136–201 | 202–255 | 256–717 |
| Human 4-1BBL | 1–69 | 70–174 | 175–210 | 211–762 |
| Murine 4-1BBL | 1–237 | 238–333 | 334–369 | 370–927 |
| Human TRAIL | 1–39 | 40–117 | 118–375 | 376–843 |
| Murine TRAIL | 1–51 | 52–111 | 112–387 | 388–873 |

*The Domains above are identified by the nucleotide boundaries of each domain using the first nucleotide of the initial methionine of the cDNA as nucleotide number 1.

One of ordinary skill in the art will understand that typical chimeric accessory molecule genes would include genes produced by exchanging domains or sub-domain segments between, for example, a mouse CD40 ligand gene and a human CD40 ligand gene. For example, chimeric accessory molecule gene may be constructed by operatively linking Domain I of the human CD40 ligand gene to Domains II–IV of the murine CD40 ligand gene. One of ordinary skill in the art will understand the variety of chimeric accessory molecule ligand genes which may be produced using the accessory molecules identified in Table I. The present invention also contemplates chimeric accessory molecules which are not shown in Table I but which are shown to have a similar domain structure. Other chimeric genes are also contemplated in which smaller segments (sub-domain segments) are exchanged between, for example, a murine CD40 ligand gene and a human CD40 ligand gene or a second murine CD40 ligand gene. One of skill in the art will understand that genes encoding accessory molecules will have at least gene segments which correspond to various functional segments of an accessory molecule ligand such as the murine CD40 ligand encoded by the murine CD40 ligand gene (SEQ ID NO: 2). It will also be apparent to one of skill in the art that the nucleotide boundaries identified in Table I may vary considerably from those identified for the murine CD40 ligand gene (SEQ ID NO: 2) and still define domains which are useful in the present invention.

Figure 2:
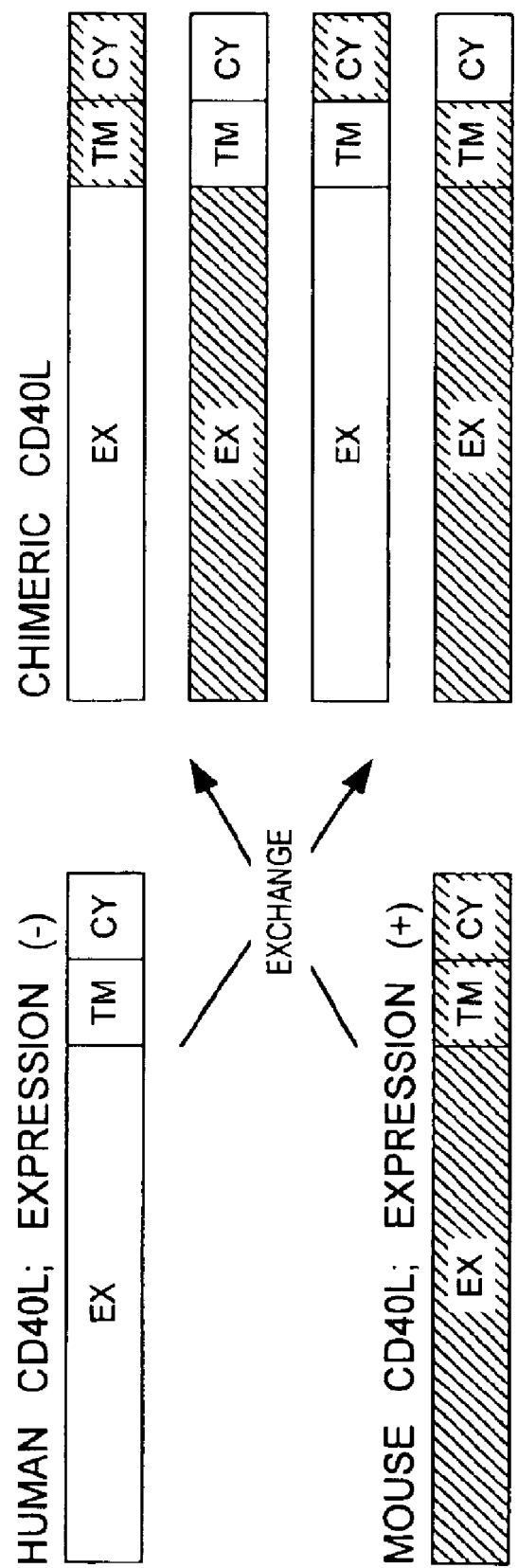
FIG. 2.

In one, preferred embodiment, the chimeric accessory molecule ligand gene is comprised of the nucleotides encoding extracellular domains (Domains III and IV) of human CD40 ligand operatively linked to the nucleotides encoding transmembrane (Domain II) and the nucleotides encoding cytoplasmic domain (Domain I) of the murine CD40 ligand gene. Examples of such preferred chimeric accessory molecules are shown in FIG. 2. An exemplary nucleotide sequence for such a gene is SEQ ID NO: 7. In other chimeric accessory molecule ligand genes of the present invention, the nucleotides encoding the extracellular domains (Domains III and IV) of the murine CD40 ligand gene may be operatively linked to nucleotides encoding the transmembrane (Domain II) and cytoplasmic domain (Domain I) of the human CD40 ligand gene. An exemplary nucleotide sequence for such a gene is SEQ ID NO: 3. In other preferred chimeric accessory molecule ligand genes of the present invention, the nucleotides encoding the extracellular domains (Domains III and IV) and transmembrane domain (Domain II) of human CD40 ligand are coupled to the nucleotides encoding cytoplasmic domain (Domain I) of murine CD40 ligand gene. An exemplary nucleotide sequence for such a gene is SEQ ID NO: 6. Other chimeric accessory molecule genes contemplated by the present invention comprise the nucleotides encoding the extracellular domains (Domains III and IV) and transmembrane domain (Domain%I) of the murine CD40 ligand gene operatively linked to the nucleotides encoding cytoplasmic domain of the human CD40 ligand gene. An exemplary nucleotide sequence for such a gene is SEQ ID NO: 5. Other chimeric accessory molecule ligand genes are contemplated by the present invention in which the human CD40 ligand gene extracellular domains (Domain III and IV) is operatively linked to the murine CD40 ligand gene transmembrane domain (Domain II) which is operatively linked to the human CD40 ligand gene cytoplasmic domain (Domain I). An exemplary nucleotide sequence for such a gene is SEQ ID NO: 4.

One of ordinary skill in the art will understand that many more combinations which utilize domains or other selected segments of any of the accessory molecule ligand genes including the human CD40 ligand genes and the mouse CD40 ligand genes are possible. Such additional chimeric accessory molecule genes would include the following genes: chimeric accessory molecule genes in which the nucleotides encoding Domain I are selected from a particular accessory molecule ligand gene and operatively linked, either directly or by an additional nucleotide sequence to the nucleotides encoding Domain II from a particular accessory molecule ligand gene. These domains then would be operatively linked either directly or by an additional nucleotide sequence to the nucleotides encoding Domain III from a particular accessory molecule ligand gene. This molecule would then be operatively linked either directly or by an additional nucleotide sequence to the nucleotides encoding Domain IV of a particular accessory molecule ligand gene. The chimeric accessory molecule ligand gene constructed in this manner may have additional nucleotides on either end or between domains which are useful to provide different amino acids in these positions. One of ordinary skill in the art will understand that these particular combinations are merely illustrations and that numerous other combinations could be contemplated in which gene segments comprising nucleotides encoding less than the entire domain of an accessory molecule are exchanged between different accessory molecules.

The present invention also contemplates chimeric accessory molecule ligand genes which are comprised of gene segments of mouse or human CD40 ligand in combination with gene segments derived from Fas ligand, $TNF_\alpha$, $TNF_\beta$, CD70, CD30L, 4-1BBL, nerve growth factor or TNF-related apoptosis inducing ligand (TRAIL). Particularly useful chimeric accessory molecule ligand genes comprise at least one gene segment which is derived from a murine CD40 ligand gene together with gene segments or a gene segments derived from a different accessory molecule ligand gene.

The present invention also contemplates chimeric accessory molecule ligand genes in which the accessory molecules produced have been modified to remove amino acids within the chimeric accessory molecule that are used by post-translational mechanisms to regulate the level of expression of the accessory molecule or accessory molecule protein on a particular cell. The sites removed from the chimeric accessory molecules or chimeric molecule may include amino acids or sites which make up protease cleavage sites including metallothionine proteases, serine proteases and other proteases that recognize an amino acid sequence either specifically or nonspecifically. In particular preferred embodiments, amino acids in Domain III which make up potential or actual recognition site(s) used by post-translational regulatory mechanisms have been modified or removed.

The present invention also contemplates chimeric accessory molecule ligand genes in which the domains, subdomain fragments or other amino acid residues have been taken from one accessory molecule ligand gene and moved into a second accessory molecule ligand gene from the same species. For example, in this particular embodiment, the human Domain I, and the human Domain II from the CD40 ligand molecule may be operatively linked to the nucleotides encoding the human Domain III from, for example, the CD70 molecule which is in turn operatively linked to human Domain IV for the CD40 ligand molecule. This chimeric accessory molecule therefore contains human CD40L Domains I, II and IV and human CD70 Domain III. An exemplary nucleotide sequence for such a gene is SEQ ID NO: 19. One of ordinary skill in the art will understand that a number of such combinations using domains from the same species from different accessory molecule ligand genes may create a number of chimeric accessory molecule genes which may all have specific activities and properties.

The present invention contemplates chimeric accessory molecule ligand genes in which the Domain III of a particular accessory molecule ligand gene has been replaced with a Domain III from a different accessory molecule ligand gene. In one particularly preferred embodiment, the mouse Domain III has been used to replace the human Domain III in the CD40 ligand molecule. This chimeric accessory molecule therefore contains the human CD40L Domain I, the human CD40L Domain II, mouse CD40L Domain III, and human CD40L Domain IV. An exemplary nucleotide sequence for such a gene is SEQ ID NO: 20.

The present invention also contemplates the use of chimeric accessory molecules that contain man-made amino acid sequences inserted into or in place of a portion of a domain or other amino acid sequence of an accessory molecule gene. These man-made amino acid segments may be created by selecting any amino acid sequence that may be used to give the accessory molecule a particular function or to remove another undesired function. These man-made amino acid segments are produced by inserting into the accessory molecule ligand gene or chimeric accessory molecule ligand gene the nucleotide sequences required to encode those particular man-made amino acid segments in the desired positions. Further, the chimeric accessory molecule ligand genes may contain nucleotide segments which comprise sub-domain segments of other molecules or small segments in which amino acids have been changed for a desired purpose. The use of sub-domain nucleotide segments allows the introduction of short amino acid sequences derived from other molecules into chimeric accessory molecules of the present invention. The incorporation of such short sub-domain segments or amino acid changes into the accessory molecule ligand allows the introduction of desired or the removal of undesired features of that molecule.

The identification of domain structures within accessory cell molecules is well known in the art and generally requires the identification of cysteine residues within the accessory molecules and the subsequent mapping of disulfide bonds between various cysteine residues. The mapping of various sub-domain segments of an accessory molecule is well known in the art and involves analysis of the amino acid sequence of the accessory molecules and generally :involves a comparison of the crystal structure of tissue necrosis factor with the use of predictive algorithms thereby producing a predicted structure of a chimeric accessory molecule or an accessory molecule. This predicted structure of these molecules can then be used to select various sub-domain portions of the molecule to be used to construct further chimeric accessory molecules. Examples of such mapping studies include the studies by M. Pitsch and C. V. Jongeneel, *International Immunology*, 5:233–238 (1993) and the analysis shown in FIG. 1.

The present invention also contemplates accessory molecule ligand genes and chimeric accessory molecule ligand genes which are truncated and encode less than the full length of the amino acid sequence found in the native accessory molecule ligand. These truncations may alter the properties of the accessory molecule ligand gene but some identified activity is maintained. Such truncations may be made by removing a gene segment or gene segments from the accessory molecule gene and typically would be performed by removing nucleotides encoding domains which are not directly involved in the binding of the accessory molecule ligand with its accessory molecule. These truncated accessory molecule ligand genes or chimeric truncated accessory molecule ligand genes may contain further gene segments which encode amino acid segments or domains which replace the domains removed from that truncated accessory molecule gene. However, such replacement of the portions of the accessory molecule removed by truncation is not necessary.

The chimeric accessory molecule genes of the present invention may be constructed using standard genetic engineering methods to operatively link a particular nucleotide sequence from one accessory molecule ligand gene to a different nucleotide sequence derived from the same or different accessory molecule ligand gene. In addition, standard genetic engineering methods may be used to insert man-made nucleotide sequences or sub-domain nucleotide sequences into the chimeric accessory molecule ligand gene. One of ordinary skill in the art will understand that various methods may be utilized to produce such chimeric accessory molecule genes. For example, a gene conversion method known as "SOEN" may be used to produce a chimeric accessory molecule gene which contains nucleotide segments derived from different chimeric accessory molecules. The methods for using this gene conversion method are well known in the art and have been described for example in Horton, R. M., *Mol. Biotechnol.*, 3:93 (1995); Ali, S. A. and A. Steinkasserer, *Biotechniques*. 18:746 (1995); Vilardaga, J. P., E. Di Paolo, and A. Bollen, *Biotechniques*, 18;604 (1995); Majumder, K., F. A. Fattah, A. Selvapandiyan, and R. K. Rhatnagar, *PCR, Methods Appl.*, 4:212 (1995); Boles, E. and T. Miosga, *Curr. Genet.* 28:197 (1995); Vallejo, A, N., R. J. Pogulis, and L. R. Pease, *PCR. Methods Appl.*, 4:9123 (1994); Henkel, T. and P. A. Baeuerle. *Anal. Biochem.*, 214:351 (1993); Tessier, D. C. and D. Y. Thomas, *Biotechniques*. 15:498 (1993); Morrison, H. G. and R. C. Desrosiers, Biotechniques,14:454 (1993); Cadwell, R. C. and G. F. Joyce, *PCR, Methods Appl.*, 2:28 (1992) ; and, Stappert, J., J. Wirsching, and R. Kemler, Nucleic*Acids Res.*, 20:624 (1992). Alternatively, one of ordinary skill in the art will understand that site-directed mutagenesis may be used to introduce changes-into a particular nucleotide sequence to directly produce or indirectly be used to produce a chimeric accessory molecule gene of the present invention. For example, the mutagen kit provided by BioRad Laboratories may be used together with the methods and protocols described within that kit to produce the desired changes in the nucleotide sequence. These methods were originally described by Kunkel, *Proc. Natl. Acad. Sci. USA*, 82:488–492 (1965) and Kunkel et al., *Meth. Enzol. Mol.*, 154:367–382 (1987). By using the site directed mutagenesis protocols described herein and known within the art, a skilled investigator may induce individual nucleotide changes which result in an altered amino acid sequence or which preserve an amino acid sequence but introduce a desired restriction enzyme recognition sequence into the gene. This new restriction endonuclease recognition site may then be used to cut the gene at that particular point and use it to a gene or segment of another accessory molecule ligand gene. In addition to these methods, one of ordinary skill in the art will understand that an entire ehimeric accessory molecule ligand gene may be synthesized using synthetic methods known in the art. This methodology only requires that the skilled artesian generating nucleotide sequence of a chimeric accessory molecule ligand gene and provide that sequence to a company which is capable of synthesizing such a gene.

B. Genetic Constructs

The present invention contemplates the use of accessory molecule ligand genes or chimeric accessory molecule ligand genes which are present in various types of genetic vectors. A genetic vector refers to a DNA molecule capable of autonomous replication in a cell into which another DNA segment can be inserted to cause the additional DNA segments to replicate. Vectors capable of expressing genes contained in that vector are referred to as "expression vectors." Thus, the genetic vectors and expression vectors of the present invention are recombinant DNA molecules which comprise at least two nucleotide sequences not normally found together in nature.

The genetic vectors useful in the present invention contain an accessory molecule ligand gene which encodes an accessory molecule ligand which is optionally operatively linked to a suitable transcriptional or translational regulatory nucleotide sequence, such as one derived from a mammalian, microbial, viral, or insect gene. Such regulatory sequences include sequences having a regulatory role in gene expression, such as a transcriptional promoter or enhancer, an operator sequence to control transcription, a sequence encoding a ribosomal binding site within the messenger RNA and appropriate sequences which control transcription, translation initiation or transcription termination.

Particularly useful regulatory sequences include the promoter regions from various mammalian, viral, microbial, and insect genes. The promoter region directs an initiation of transcription of the gene and causes transcription of DNA through and including the accessory molecule ligand gene. Useful promoter regions include the promoter found in the Rous Sarcoma Virus (RSV)—long terminal repeat (LTR), human cytomegalovirus (HCMV) enhancer/promoter region lac promoters, and promoters isolated from adenovirus, and any other promoter known by one of ordinary skill in the art would understand to be useful for gene expression in eukaryotes, prokaryotes, viruses, or microbial cells. Other promoters that are particularly useful for expressing genes and proteins within eukaryotic cells include mammalian cell promoter sequences and enhancer sequences such as those derived from polyoma virus, adenovirus, simian virus 40 (SV40), and the human cytomegalovirus. Particularly useful are the viral early and late promoters which are typically found adjacent to the viral origin of replication in viruses such as the SV40. Examples of various promoters which have been used in expression vectors have been described by Okiama and Berg (Mol. Cell. Biol. 3:280, 1983), the pMLSVN SV40 described by Kossman et al., *Nature* 312:768 (1984). one of ordinary skill in the art will understand that the selection of a particular useful promoter depends on the exact cell lines and the other various parameters of the genetic construct to be used to express the accessory molecule ligand gene or the chimeric accessory molecule ligand gene within a particular cell line. In addition, one of ordinary skill in the art will select a promoter which is known to express genes in the target cell at a sufficiently high level to be useful in the present invention.

The genetic vectors and expression vectors of the present invention optionally contain various additional regulatory sequences including ribosome binding sites which allow the efficient translation of the messenger RNA produced from an expression vector into proteins, the DNA sequence encoding various signals peptides which may be operatively linked to the accessory molecule ligand gene or the chimeric accessory molecule ligand gene. The signal peptide, if present, is expressed as a precursor amino acid which enables improved extracellular secretion of translation fusion polypeptide.

The genetic constructs contemplated by the present invention therefore include various forms of accessory molecule ligand genes described above which are operatively linked to either a promoter sequence or a promoter and enhancer sequence and also operatively linked to a polyadenylation sequence which directs the termination and polyadenylation of messenger RNA. It is also contemplated that the genetic constructs of the present invention will contain other genetic sequences which allow for the efficient replication and expression of that construct within the desired cells. Such sequence may include introns which are derived from native accessory molecule ligand genes or, for example, from a virus gene.

The present invention also contemplates gene therapy vectors which are able to directly infect mammalian cells so as to introduce the desired accessory molecule ligand gene or chimeric accessory molecule ligand gene into that cell. These gene therapy vectors are useful for directly infecting cells which have been isolated from an animal or patient, or can be directly introduced into an animal or patient and thereby directly infect the desired cell within that animal or patient.

Many types of gene therapy vectors which are able to successfully transfer genes and cause the expression of desired foreign DNA sequences have been developed and described in the literature. For example, the article entitled "Gene Transfer Vectors for Mammalian Cells" in *Current Comm. Mol. Biol.*, Cold Springs Harbor Laboratory, New York (1987). Further, naked DNA can be physically introduced into eukaryotic cells including human cells by transvection using any number of techniques including calcium phosphase transfection (Berman et al., *Proc. Natl. Acad. Sci. USA*, 81:7176 (1984)), DEAE-Dextran Transfection, protoplast fusion (Deans et al., *Proc. Natl. Acad. Sci. USA*, 81:1292 (1984)), electroporation, liposome fusion, polybrene transfection and direct gene transfer by laser micropuncture of the cell membrane. In addition, one of ordinary skill in the art will understand that any technique which is able to successfully introduce the DNA into a cell in such a manner as to allow it to integrate into the genome of a cell and allow the expression of the desired gene would be useful in the present invention.

Specifically, gene therapy vectors which utilize recombinant infectious virus particles for gene delivery have been widely described. See, for example, Brody, S. L. and R. G. Crystal, *Ann. N. Y. Acad. Sci.*, 716:90 (1994); Srivastava, A., *Blood, Cells*, 20:531 (1994); Jolly, D., *Cancer Gene Ther.*, 1:51 (1994); Russell, S. J., *Eur. J. Cancer*, 30A:1165 (1994); Yee, J. K., T. Friedmann, and J. C. Burns, *Methods Cell Biol.*, 43 Pt A:99 (1994); Boris-Lawrie, K. A. and H. M. Temin, *Curr. Opin. Genet. Dev.*, 3:102 (1993); Tolstoshev, P., *Annu. Rev. Pharmacol. Toxicol.*, 33:573 (1993); and, Carter, B. J., *Curr. Opin. Biotechnol.*, 3:533 (1992). The present invention contemplates the use of gene therapy vectors to carry out the desired methodology of the present invention by introducing a gene encoding an accessory molecule ligand gene or a chimeric accessory molecule ligand gene into the cell. Many viral vectors have been defined and used as gene therapy vectors and include virus vectors derived from simian virus 40 (SV40), adenoviruses, adeno-associated viruses, and retroviruses. One of ordinary skill in the art will understand that useful gene therapy vectors are vectors which are able to directly introduce into the target cells the DNA which encodes the accessory molecule ligand and allow that DNA to persist in the cell so as to express the accessory molecule ligand in the desired manner within the cell.

The gene therapy vectors of the present invention are useful for introducing accessory molecule ligand genes into a variety of mammalian cells including human cells. The particular cells infected by the gene therapy vector will depend on the various specifics of the vector and such vectors can be used to introduce the accessory molecule ligand genes of the present invention into hematopoietic or lymphoid stem cells, antigen presenting cells, embryonic stem cells, and other cells which are capable of presenting antigen within the immune system including cells which have CD40 on their surface. Further, such gene therapy vectors are able to introduce a gene encoding an accessory molecule ligand gene into a human neoplastic cell such as a lymphoma, leukemia, AML, CLL, CML, AMML, CMML, breast cancer, lung cancer, ovarian cancer or any tumor capable of acting as antigen presenting cells or cells which can stimulate bystander antigen presenting cells. Further, the contemplated gene therapy vectors may be used to introduce the accessory molecule ligand genes of the present invention into cells which have been engineered to make those cells capable of presenting antigen to the immune system.

III. Cells Containing Genetic Constructs Encoding an Accessory Molecule Ligand or Chimeric Accessory molecule Ligand The present invention also contemplates various cells which contain the genetic constructs of the present invention. These cells contain the constructs which encode the accessory molecule ligand gene and thus contain the various genetic elements described in Section II.B. above. These cells may be microbial cells, eukaryotic cells, insect cells, and various mammalian cells including human cells. In preferred embodiments of the present invention, these cells include various neoplastic cells including human neoplastic cells. These neoplastic cells may be of any cell type and include cells of the immune system, and other blood cells. Particularly preferred are any neoplastic cells which may function as an antigen presenting cells within the immune system or which may stimulate bystander antigen presenting cells by expression of a transgenic accessory cell molecule of the present invention. Typically these neoplastic which are able to function to present antigen to the immune system have or have had an accessory molecule, such as the CD40 molecule, on the cell surface. Generally, these cells are naturally capable of presenting antigen to the immune system, but the present invention also contemplates the introduction of accessory molecule ligand genes into a cell which is not naturally able to present antigen to the immune system but which has been genetically engineered to make that cell capable of presenting antigen to the immune system. Typically, these cells include various known cell types such as monocytes, macrophages, B cells, Langerhans cells, interdigitating cells, follicular dendritic cells or Kupffer cells and the like which have become neoplastic. In addition, the present invention also contemplates cells from various carcinomas, breast, ovarian and lung cancers which contain the genetic constructs described herein. In other preferred embodiments, an accessory molecule ligand gene of the present invention is placed into cells which may be injected into a treatment site such as a tumor bed or joint. For example, the accessory molecule ligand gene of the present invention may be inserted into a fibroblast cell and the accessory molecule ligand expressed on the surface of that cell. The fibroblasts are then injected into the treatment site and cause the desired immune effect due to the presence of the accessory molecule ligand on the surface of those cells. These cells stimulate other immune cells present in that treatment site (bystander cells). This process then results in the desired effect on the immune system.

IV. Methods Utilizing Genetic Vectors and Constructs Containing an Accessory Molecule Ligand Gene The present invention contemplates methods of altering the immunoreactivity of human cells using a method which includes introducing a gene encoding an accessory molecule ligand gene into the human cells so that the accessory molecule ligand encoded by that gene is expressed on the surface of those cells. The present invention is useful for any human cells which participate in an immune reaction either as a target for the immune system or as part of the immune system which responds to the foreign target. A large variety of methods are contemplated in which the final result is that the accessory molecule ligand gene is introduced into the desired cells. These methods include ex viva methods, in-vivo methods and various other methods which involve injection of DNA, genetic vectors or gene therapy vectors into the animal or human, including injection directly into the tumor bed present in any animal or human.

Ex vivo methods are contemplated wherein the cells into which the accessory molecule ligand gene is to be introduced are isolated from the animal or patient and then the gene is introduced into those isolated cells using suitable methods. Examples of useful ex vivo methods have been described for example by Raper, S. E., M. Grossman, D. J. Rader, J. G. Thoene, B. J. Clark, D. M. Kolansky, D. W. Muller, and J. M. Wilson, *Ann. Surg.*, 223:116 (1996); Lu, L., R. N. Shen, and H. E. Broxmeyer, *Crit. Rev. Oncol. Hematol.*, 22:61 (1996) ; Koc, O, N., J. A. Allay, K. Lee, B. M. Davis, J. S. Reese, and S. L. Gerson, *Semin., Oncol.*, 23:46 (1996); Fisher, L. J. and J. Ray, *Curr. Opin. Neurobiol.*, 4:735 (1994); and, Goldspiel, B. R., L. Green, and K. A. Calis, *Clin. Pharm.*, 12:488 (1993). D. Dillco et al., in *Blood* 90:1927–1933 (1997), describe a method, using CD40L-activated cells, for treating B-acute lymphoblastic leukemia (ALL). They cocultured leukemia cells with fibroblasts infected with a retroviral vector encoding CD40L, then injected the cell mix into mice. Such an approach, if taken in humans, would differ from that contemplated here in that the therapeutic cells are stimulated in-vitro, by another cell line expressing the accessory molecule ligand. Schultze, J. L. et al., in *Blood* 89: 3806–3816 (1997), describe a method for stimulating T-TILs (tumor-infiltrating T cells) cytotoxic for follicular lymphoma (FL) cells by exposing them, in vitro, to FL B cells which were previously cultured with CD40L-expressing fibroblasts. They propose an adoptive immunotherapy in which T-TILS stimulated in this manner are transfused into patients. This method also requires in vitro stimulation, of the cells to be transfused, with another cell line expressing an accessory molecule.

Following the introduction of the gene, including any optional steps to assure that the accessory molecule ligand gene has been successfully introduced into those isolated cells, the isolated cells are introduced into the patient either at a specific site or directly into the circulation of the patient. In preferred embodiments of the present invention, cell surface markers, including molecules such tumor markers or antigens identify the cells are used to specifically isolate these molecules from the patient. One of ordinary skill in the art will understand that such isolation methods are well known and include such methodologies as fluorescence activated cell sorting (FAGS), immunoselection involving a variety of formats including panning, columns and other similar methods.

The present invention also contemplates introducing the accessory molecule ligand gene into the desired cells within the body of an animal or human patient without first removing those cells from the patient. Methods for introducing genes into specific cells in vivo, or within the patient's body are well known and include use of gene therapy vectors and direct injection of various genetic constructs into the animal or patient. Examples of useful methods have been described by Danko, I. and J. A. Wolff, *Vaccine*, 12:1499 (1994); Raz, E., A. Watanabe, S. M. Baird, R. A. Eisenberg, T. B. Parr, M. Lotz, T. J. Kipps, and D. A. Carson, *Proc. Natl. Acad. Sci. U.S.A.*, 90:4523 (1993); Davis, H. L., R. G. Whalen, and B. A. Demeneix, *Hum. Gene Ther.*, 4:151 (1993); Sugaya, S., K. Fujita, A. Kikuchi, H. Ueda, K. Takakuwa, S. Kodama, and K. Tanaka, *Hum. Gene Ther.*, 7:223 (1996); Prentice, H., R. A. Kloner, Y. Li, L. Newman, and L. Kedes, *J. Mol. Cell Cardiol.*, 28:133 (1996); Soubrane, C., R. Mouawad, O. Rixe, V. Calvez, A. Ghoumari, O. Verola, M. Weil, and D. Khayat, *Eur. J. Cancer*. 32A:691 (1996); Kass-Eisler, A., K. Li, and L. A. Leinwand, *Ann. N. Y. Acad. Sci.*, 772:232 (1995); DeMatteo, R. P., S. E. Raper, M. Ahn, K. J. Fisher, C. Burke, A. Radu, G. Widera, B. R. Claytor, C. F. Barker, and J. F. Markmann, *Ann. Surg.*, 222:229 (1995); Addison, C. L., T. Braciak, R. Ralston, W. J. Muller, J. Gauldie, and F. L. Graham, *Proc. Natl. Acad. Sci. U.S.A.*, 92:8522 (1995); Hengge, U. R., P. S. Walker, and J. C. Vogel, *J. Clin. Invest.*, 97:2911 (1996); Felgner, P. L., Y. J. Tsai, L. Sukhu, C. J. Wheeler, M. Manthorpe, J. Marshall, and S. H. Cheng, *Ann. N. Y. Acad. Sci.*, 772:126 (1995); and, Furth, P. A., A. Shamay, and L. Hennighausen, *Hvbridoma*, 14:149 (1995). In a typical application, a gene therapy vector containing an accessory molecule ligand gene is introduced into the circulation or at a localized site of the patient to allow the gene therapy vector to specifically infect the desired cells. In other preferred embodiments the gene therapy vector is injected directly into the tumor bed present in an animal which contains at least some of the cells into which the accessory molecule ligand gene is to be introduced.

The present invention also contemplates the direct injection of DNA from a genetic construct which has a promoter and accessory molecule ligand gene followed by a polyadenylation sequence into a patient or animal. Examples of such useful methods have been described by Vile, R. G. and I. R. Hart, *Ann. Oncol.*, 5 Suppl 4:59 (1994). The genetic construct DNA is directly injected into the muscle or other sites of the animal or patient or directly into the tumor bed of the animal or patient. Alternatively, DNA from a genetic construct containing at least an accessory molecule ligand gene is used and directly injected into the animal.

In preferred embodiments of the present invention, the immune reaction or response of a human patient or animal is altered by introducing the accessory molecule ligand gene into cells, including human cells which have an accessory molecule present on the cell surface. Such cells include human cells, human antigen presenting cells and optionally these cells may be neoplastic antigen presenting cells which have the capacity to express the accessory molecule on the surface of the cell or cells which are capable of stimulating. In some embodiments, the amount of accessory molecule present on the surface of the cells into which the accessory molecule ligand gene is to be introduced is very small and such small amounts of the accessory molecule may result from down-regulation of that accessory molecule on the surface of such cells. In some embodiments, the cells into which the accessory molecule ligand gene is introduced have at least low levels of the CD40 molecule present on the cell surface or are derived from cells. which did express the CD40 ligand molecule on the cell surface but have reduced or eliminated that expression.

The preferred methods of altering the immunoreactivity of a particular cell are applicable to mammalian cells including human cells. These human cells may include neoplastic human cells such as human lymphomas, leukemias, and other malignancies including breast, lung and ovarian cancers. In some preferred embodiments the cells are normal antigen presenting cells of a human patient such as monocytes, macrophages, B cells, Langerhans cells, interdigitating cells, follicular dendritic cells, Kupffer cells, and other similar cells. In preferred embodiments, the cells are lymphocytes which acquire altered immunoreactivity when the accessory molecules of the present invention are introduced into those cells. In other preferred embodiments, the cells may be neoplastic or normal cells which are capable of stimulating bystander antigen presenting cells when the accessory molecule ligand genes of the present invention are introduced into these cells. The present invention also contemplates that cells which are not naturally capable of presenting antigen to the immune system may be genetically engineered to introduce the genes encoding the molecules required for antigen presentation, including genes encoding an accessory molecule, and thus allow these cells to act as artificial antigen presenting cells. The accessory molecule ligand gene may then be introduced into these artificial antigen presenting cells. Various tests are well known in the literature to determine whether a particular cell is able to function as an antigen presenting cell, such as cell proliferation or the production of lymphokines and therefore this aspect of the present invention may be easily determined.

In addition to the above normal human cells, the present invention also contemplates introducing the accessory molecule ligand gene into various neoplastic or malignant cells which optionally are antigen presenting cells. Such human neoplastic cells which are contemplated include leukemias, lymphomas, AML, AMML, or CMML, CML, CLL and any neoplastic cell which is capable of stimulating bystander antigen presenting cells when an accessory molecule ligand is introduced into that cell. Also contemplated are neoplastic cells such as a breast, ovarian or lung cancer cell which is capable of or is engineered to act as an antigen presenting cell. However, the present immunomodulation also applicable to other malignancies not specifically identified and thus would include any tumor of any cell capable of presenting antigen within the animal or human immune system or any cell which is capable of acting as an antigen presenting cell or capable of stimulating bystanding antigen presenting cells after an accessory molecule ligand gene has been introduced into those cells. Generally these antigen presenting cells have accessory molecules on the surface of the cells.

The present methods of altering the immunoreactivity of a human or animal cell contemplate the introduction of an accessory molecule ligand gene into the cells for which altered immunoreactivity is desired. The genes useful in the present invention include the wide range of accessory molecule ligand genes and chimeric accessory molecule ligand genes identified above and in preferred embodiments include at least a portion of the murine CD40 ligand gene. In particularly preferred embodiments, the accessory molecule ligand gene introduced into the cells using the methods of the present invention is selected to correspond to the accessory molecule present on the surface of the cells for which altered immunoreactivity is desired. In one particular application of the present invention, the immunoreactivity of a cell which expresses the CD40 molecule on the cell surface would be accomplished by introducing the gene which encodes the CD40 ligand molecule and more preferably the murine CD40 ligand molecule.

The present invention also contemplates altering the immunoreactivity of human or animal cells by introducing an accessory molecule ligand gene which is a chimeric accessory molecule ligand gene into the cell. The various useful chimeric accessory molecule ligand genes were identified above and could include a wide variety of molecules and allow the unique properties of those chimeric accessory molecule ligand genes to be utilized to alter the immunoreactivity of the target cells. In preferred embodiments, useful chimeric accessory molecule ligand genes are genes which encode at least a portion of the accessory molecule ligand which is capable of binding the accessory molecule present on the surface of the cells for which altered immunoreactivity is desired.

The methods of the present invention for altering the immunoreactivity contemplate the use of genetic vectors and genetic constructs including gene therapy vectors which encode an accessory molecule ligand and therefore contain an accessory molecule ligand gene. Typically, the genetic vectors and genetic constructs including the gene therapy vectors of the present invention have a promoter which is operatively linked to the accessory molecule ligand gene followed by a polyadenylation sequence. In other embodiments, the only requirement is that the genetic vectors, genetic constructs, and gene therapy vectors of the present invention contain the accessory molecule ligand gene or the chimeric accessory molecule ligand gene.

V. Methods of Treating Neoplasia

The present invention also contemplates methods of treating human neoplasia comprising inserting into a human neoplastic cell a gene which encodes an accessory molecule ligand so that the accessory molecule ligand is expressed on the surface of the neoplastic cells. The present invention contemplates treating human neoplasia both in vivo, ex vivo and by directly injecting various DNA molecules containing a gene which encodes an accessory molecule ligand into the patient. However, at a minimum, the present methods for treating human neoplasia involve inserting the gene encoding the accessory molecule ligand into the neoplastic cells in such a way as to allow those neoplastic cells to express the accessory molecule ligand on the cell surface. The expression of the accessory molecule ligand gene in these neoplastic cells modulates the immune system to cause the neoplasia to be reduced or eliminated.

In a preferred method of treating human neoplasia, the method further comprises the steps of first obtaining the human neoplastic cells from a human patient and then inserting into the isolated human neoplastic cells a gene which encodes an accessory molecule ligand so that the accessory molecule ligand is expressed on the surface of the neoplastic cells. The human neoplastic cells having the accessory molecule ligand on the surface of that cell are then infused back into the human patient. One of ordinary skill in the art will understand that numerous methods are applicable for infusing the altered human neoplastic cells containing the gene encoding the accessory molecule ligand back into the patient and that these methods are well known in the art.

The contemplated methods of treating human neoplasia are applicable to a wide variety of human neoplasias including lymphomas, leukemias, and other malignancies. In preferred embodiments the human neoplasia is a neoplasia which involves the antigen presenting cells of the human immune system and includes monocytes, macrophages, B cells, Langerhans cells, interdigitating cells, follicular dendritic cells, Kupffer cells, and the like. In other preferred embodiments, the human neoplasia is a leukemia, a lymphoma, AML, AMML, CMML, CML or CLL, lung cancer, breast cancer, ovarian cancer and other similar neoplasias.

The genetic vectors, genetic constructs and gene therapy vectors useful in the methods of treating human neoplasia of the present invention have been disclosed above and include constructs in which a promoter is operatively linked to the accessory molecule ligand gene or the chimeric accessory molecule ligand gene which is in turn operatively linked to a polyadenylation sequence. The methods of treating human neoplasia contemplate the use of genetic constructs, genetic vectors and gene therapy vectors as described in this specification. In addition, the present invention contemplates the use of DNA which contains at least a gene encoding an accessory molecule ligand gene. This gene may or may not contain a promoter and other regulatory sequences.

In preferred embodiments of the present invention, the cells comprising the human neoplasia are located in at least one defined site termed a tumor bed within the tumor patient. This tumor bed typically contains the tumor or neoplastic cell together with a number of other cells which are associated with the tumor or neoplastic cells. The present invention contemplates methods of treating such human neoplasia present in a tumor bed by injecting into the tumor bed of the patient, a gene which encodes an accessory molecule ligand so that the accessory molecule ligand is expressed on the surface of the tumor cells thereby causing the cells by participate in an immune reaction. The gene which encodes the accessory molecule ligand may be present as part of a gene therapy vector, genetic construct or genetic vector.

In preferred embodiments, the accessory molecule ligand gene is a chimeric accessory molecule ligand gene which has at least a portion of the murine CD40 ligand gene is used. In other preferred embodiments, the accessory molecule ligand encoded is capable of binding an accessory molecule present on the human neoplasia to be treated.

The various gene therapy vectors used in the treatment methods of the present invention includes vectors which are capable of directly infecting human cells. Such vectors have been described in the literature and are readily adaptable to the methods described in the present invention.

The present invention contemplates the use of any type of gene therapy including the method of Raper, S. E. et al., *Ann. Surg.*, 223:116 (1996); Lu, L. et al., *Crit. Rev. Oncol. Hematol.*, 22:61 (1996); Koc, O. N. et al., *Semin. Oncol.*, 23;46 (1996); Fisher, L. J. et al., *Curr. Opin. Neurobiol.*, 4:735 (1994); Goldspiel, B. R. et al., *Clin. Pharm.*, 12:488 (1993); Danko, I. et al., *Vaccine*, 12:1499 (1994); Raz, E. et al., *Proc. Natl. Acad. Sci. U.S.A.*, 90:4523 (1993); Davis, H. L. et al., *Hum. Gene Ther.*, 4:151 (1993); Sugaya, S. et al., *Hum. Gene Ther.*, 4:151 (1993); Sugaya, S. et al., *J. Mol. Cell Cardiol.*, 28:133 (1996); Soubrane, C. et al., *Eur. J. Cancer*, 32A:691 (1996); Kass-Eisler, A. et al., *ann. N. Y. Acad. Sci.*, 772:232 (1995); DeMatteo, R. P. et al., *Ann. Surg.*, 222:229 (1995); Addison, C. L. et al., *Proc. Natl. Acad. Sci, U.S.A.*, 92:8522 (1995); Hengge, U. R. et al., *J. Clin. Invest.*, 97:2911 (1996); Felgner, P. L. et al., *Ann. N. Y. Acad. Sci.*, 772:126 (1995); Furth, P. A. *Hybridoma*, 14:149 (1995); Yovandich, J. et al., *Hum. Gene Ther.*, 6:603 (1995); Evans, C. H. et al., *Hum. Gene Ther.*, 7:1261.

VI. Methods of Vaccination

The present invention contemplates methods of vaccinating an animal against a predetermined organism comprising administering to that animal a vaccine containing immunogenic animal antigens capable of causing an immune response in that animal against the desired organism together with a vector containing a gene encoding an accessory molecule ligand. The present invention also contemplates methods of vaccinating an animal which include administering the genes which encode the immunogenic antigen capable of causing a desired immune response or altering the immune response to a particular antigen together with a vector containing a gene including the accessory molecule ligand gene. In this particular embodiment, the vector or vectors introduced encode the immunogenic antigens desired and the desired accessory molecule ligand. The present invention also contemplates that the gene or genes encoding the immunogenic peptide or peptides may be present on the same vector as is the gene or genes encoding the accessory molecule ligand.

The vaccination methods of the present invention are general in that they may be used to produce a vaccination against any predetermined organism, such as a virus, a bacteria, a fungus or other organism. In addition, the present vaccination methods may be used to produce an immune response against a neoplastic cell.

In other preferred embodiments, the vaccination methods of the present invention utilize a genetic vector, a genetic construct or a gene therapy vector which contains an accessory molecule ligand gene which is a chimeric accessory molecule ligand gene. That chimeric accessory molecule ligand gene preferably contains at least a portion of the murine CD40 ligand gene. In other preferred embodiments, the vaccination method utilizes a DNA molecule which encodes at the minimum the accessory molecule ligand gene or a chimeric accessory molecule ligand gene. This particular DNA may or may not include a promoter sequence which directs the expression of the accessory molecule ligand gene.

The present invention also contemplates that the vaccination method may utilize a genetic vector which is capable of expressing an accessory molecule ligand within a particular cell or organism together with a vector which is capable of expressing at least a single polypeptide from an andovirus. This andovirus polypeptide maybe expressed from the same or different vector which expresses the accessory molecule ligand in that cell. In this particular embodiment, the andovirus polypeptide is also expressed in at least one cell type within the organism and serves to modulate the immune response found in response to this vaccination protocol.

The present invention also contemplates the introduction of an accessory molecule ligand gene into cells which are present in the joints of patients with rheumatoid arthritis. In preferred embodiments, the accessory molecule ligand gene introduced comprises at least a portion of the Fas ligand gene and upon expression the accessory ligand induces the cell death of cells expressing Fas on the cell surface. This process leads to the reduction of the destructive inflammatory process.

The following examples are provided to illustrate various aspects of the present invention and do not limit the scope of that invention.

VII. Methods of Treating Arthritis

The present invention also contemplates methods of treating arthritis comprising inserting into a joint, cells which have been transformed with an accessory molecule, such as the Fas ligand. In preferred embodiments, the expression of that accessory molecule ligand or the stability of that molecule on the surface of the cells has been altered. In these preferred embodiments, the accessory molecule ligand functions in an enhanced manner to aid in the treatment of arthritis within the joint. The present invention contemplates treating human arthritis both in vivo, ex vivo, and by directly injecting various DNA molecules containing genes which encode the useful accessory molecule ligand into the patients. Various useful protocols may be designed to rheumatoid arthritis including those described in the example section below.

The present invention contemplates the treatment of arthritis utilizing accessory molecule ligand genes which may be chimeric accessory molecule ligand genes comprised of portions of that gene being derived from two different accessory molecule ligand genes. In other embodiments, the chimeric accessory molecule ligands may be produced by utilizing domains from the same accessory molecule ligand gene. The resulting chimeric accessory molecule ligands have an altered stability on the surface of cells upon which they are expressed. This altered stability modulates the function of the immune system in the local environment around the cells in which these chimeric accessory molecule ligands are expressed. For example, in certain preferred embodiments, Fas ligand stability is altered on the surface of cells within a joint of a patient suffering from arthritis. This altered stability modulates the immune system and causes the cells to be targeted for apoptosis and thus reducing the immune response within the inflamed joint. In other embodiments, the accessory molecule ligand genes described within are altered such that the resulting accessory molecule ligand has an altered stability and causes an immunodulatory effect which can be useful in the treatment of arthritis.

The present invention contemplates in preferred embodiments that chimeric accessory molecule ligands genes be utilized in the treatment of arthritis. These chimeric accessory molecule ligand genes preferably contain at least a portion of the Fas ligand gene Domain IV, which carries the effect or function for Fas ligand. In preferred embodiments, at least in the portion of that domain, is present which allows Fas ligand to have its biologic effects. In other preferred chimeric accessory molecule ligands, those ligands contain domains from other accessory molecule ligand genes of the present invention or from a different domain of the same accessory molecule ligand. Particularly preferred are Fas chimeric accessory molecule ligand genes made up on Domain IV of the human Fas ligand operatively linked with Domain III of the mouse Fas ligand. This particular combination results in more stable Fas ligand with Domain III of the mouse ligand, the activity of the human Fas ligand gene is altered.

Alternatively, in other preferred embodiments, the murine Fas ligand gene is used to encode the murine Fas ligand on the surface of cells in place of the human Fas ligand. The murine Fas ligand is more stable than the human Fas ligand and thus, alters the Fas ligand activity in the joint. The resulting alter Fas ligand activity is useful in the treatment of rheumatoid arthritis.

Further preferred embodiments include embodiments in which the effect or function present on Domain IV of the human Fas ligand is combined with other domains from other accessory molecule ligands. For example, CD70 Domain III is more stable than Domain III of the human Fas ligand and thus the chimeric accessory molecule ligand made up of Domain III from the human CD70 and Domain IV of the Fas ligand together with other supporting domains would be more stable. The increased stability leads to increase Fas ligand activity. In other preferred embodiments, Domain III of the Fas ligand is replaced with multiple copies of a domain or domains. Such multiple copies of domains include domains made up of two or more copies of other domains such as Domains III or I of the CD70 molecule.

In other preferred embodiments, the present invention contemplates accessory molecule ligand genes, such as Fas ligand genes, in which a cleavage site for matrix-metalloproteinase (MMP), have been removed from the accessory molecule ligand. MMP cleavage and recognition sites, charted in FIG. 28, are discussed in Smith, M. M. et al., Journal of Biol. Chem. 270:6440–6449 (25) and Nagase, H., and G. B. Fields, Biopolymers (Peptide Science) 40:399–416 (96). In preferred embodiments, at least one MMP site has been removed from at least Domain III of the Fas ligand gene. The removal of the MMP site from the Fas ligand gene makes the Fas ligand more stable and thus, more effective in the treatment of arthritis.

In other preferred embodiments, chimeric accessory molecule ligand genes are comprised of portions of the human Fas ligand gene with other domains from other human accessory molecule ligands or domains from accessory molecules derived from other species. For example, the present invention contemplates the use of domains from CD40 ligand, CD70 ligand, CD30 ligand, TNF-related apoptosis inducing ligand (TRAIL), TNF-α as well as mutants of human Fas ligand and murine Fas ligand. Production of such chimeric accessory molecule ligands is easily accomplished by manipulating and producing accessory molecule ligand genes which are chimeric and thus has portions derived from at least two different accessory molecule ligand genes.

EXAMPLES

1. Expression of Human and Mouse Accessory Molecule Ligand in Human CLL Cells a. Construction of a Genetic Construct and Gene Therapy Vector Containing a Human and Mouse Accessory Molecule Ligand Gene Either the human accessory molecule ligand gene (human CD40 ligand) or the murine accessory molecule ligand gene (murine CD40 ligand) was constructed utilizing the respective human and murine genes. Each of these genes was cloned in the following manner.

i. Murine CD40-L cloning

Total RNA was isolated using the RNA STAT-60 kit (Tel-Test "B" Inc., Friendswood, Tex.) from $1\times10^7$ B6 mouse splenocytes that were previously activated for 8 hours with immobilized CD3-specific mAb. cDNA was then synthesized with the Superscript cDNA synthesis kit (Gibco BRL, Grand Island, N.Y.) using oligo-dT primers. The murine CD40 ligand (mCD40-L) gene was then amplified from the cDNA by PCR using the following mCD40-L specific primers. 5'-GTTAAGCTTTTCAGTCAGCATGATAGAA (SEQ ID NO:26), 5'-GTTTCTAGATCAGAGTTTGAGTAAGCC (SEQ ID NO: 27). The amplified mCD40-L PCR product was subcloned into the HindIII and XbaI sites of the eukaryotic expression vector pcDNA3 (Invitrogen, San Diego, Calif.). A DNA fragment encompassing the CMV promoter, mCD40-L gene, and polyadenylation signal was released from this plasmid construct after restriction digestion with BglII and XhoI enzymes. This DNA fragment was then subcloned into the shuttle plasmid MCS(SK)pXCX2 (Spessot R, 1989, *Virology* 168:378) that was designated mCD40-L pXCX2. This plasmid was used for adenovirus production as described below.

ii. Human CD40-L Cloning

A plasmid containing the gene for human CD40-L was used to produce the human CD40-L gene used herein. The sequence of this gene is available and thus this source of the gene was used merely for convenience. See GenBank accession no. X67878. This plasmid was used for PCR amplification of the human CD40-L gene using the specific primers, sense primer 5' CCAAGACTAGTTAACACAGCATGATC-GAAA 3' (SEQ ID NO: 28) and antisense primers 5' CCAATGCGGCCGCACTCAGAATTCAACCTG 3' (SEQ ID NO: 29).

These primers contain flanking restriction enzyme sites for subcloning into the eukaryotic expression plasmid pRc/CMV (Invitrogen). The PCR amplified CD40-L fragment was subcloned into the SpeI and NotI sites of pRc/CMV and designated hCD40-L pRc/CMV. A BglII and XhoI fragment encompassing the CMV promoter, hCD40-L gene, and polyadenylation signal was then released from this plasmid and subcloned into the shuttle plasmid MCS (SK)pXCX2 as described above. This plasmid was designated hCD40-L pXCX2. This plasmid was used for adenovirus production as described below.

iii. Adenovirus Synthesis

Either mCD40-L pXCX2 or hCD40-L pXCX2 plasmids were co-transfected with pJM17 (Graham and Prevec, 1991, Methods in Molecular Biology, Vol 7) into 293 cells (American Type Culture Collection, Rockville, Md.) using the calcium phosphate method (Sambrook, Fritsch, and Maniatis, 1989, *Molecular Cloning, A Laboratory Manual*, 2nd edition, chapter 16:33–34). Isolated adenovirus plaques were picked and expanded by again infecting 293 cells. High titer adenovirus preparations were obtained as described (Graham and Prevec, 1991, Methods in Molecular Biology, Vol 7), except for the following modifications. The cesium chloride gradient used for concentrating viral particles was a step gradient, with densities of 1.45 g/cm$^3$ and 1.2 g/cm$^3$. The samples were spun in a SW41 rotor (Beckman, Brea, Calif.) at 25,000 rpm at 4° C. The viral band was desalted using a Sephadex G25 DNA grade column (Pharmacia, Piscataway, N.J.). The isolated virus was stored at 70° C. in phosphate buffered saline with 10% glycerol. The virus titer was determined by infecting 293 cells with serial dilutions of the purified adenovirus and counting the number of plaques formed. Viral titers typically ranged from $10^{10}$ to $10^{12}$ plaque forming units/ml (PFU/ml).

b. Introduction of a Murine and Human Accessory Molecule Ligand Gene into CLL Cells and HeLa Cells For adenovirus infection, $10^6$ freshly thawed and washed CLL cells or HeLa cells were suspended in 0.5 to 1 mL of culture medium for culture at 37° C. in a 5% $CO_2$-in-air incubator. Adenovirus was added to the cells at varying multiplicity of infection (MOI), and the infected cells were cultured for 48 hours, unless otherwise stated, before being analyzed for transgene expression.

c. Expression of an Accessory Molecule Ligand Gene in CLL Cells and HeLa Cells

The CLL and HeLa cells which were infected with the adenovirus vector containing either mouse or human CD40 ligand genes prepared in Example 1b. were then stained with commercially available monoclonal antibodies immunospecific for either human or mouse CD40 ligand (Pharmingen, San Diego, Calif.) using the manufacturer's directions. The CLL and HeLa cells were washed in staining media (SM) consisting of RPMI-1640, 3% fetal calf serum and 0.05% sodium azide and containing propidium iodide and then analyzed on a FACScan (Becton Dickinson, San Jose, Calif.). Dead cells and debris were excluded from analysis by characteristic forward and side light scatter profiles and propidium iodide staining. Surface antigen expression was measured as the mean fluorescence intensity ratio (MFIR). MFIR equals the mean fluorescence intensity (MFI) of cells stained with a specific FITC-conjugated MoAB, divided by the MFI of cells stained with a control IgG-FITC. This method controls for the nonspecific increases in autofluorescence seen in larger, more activated cells.

Figure 3:
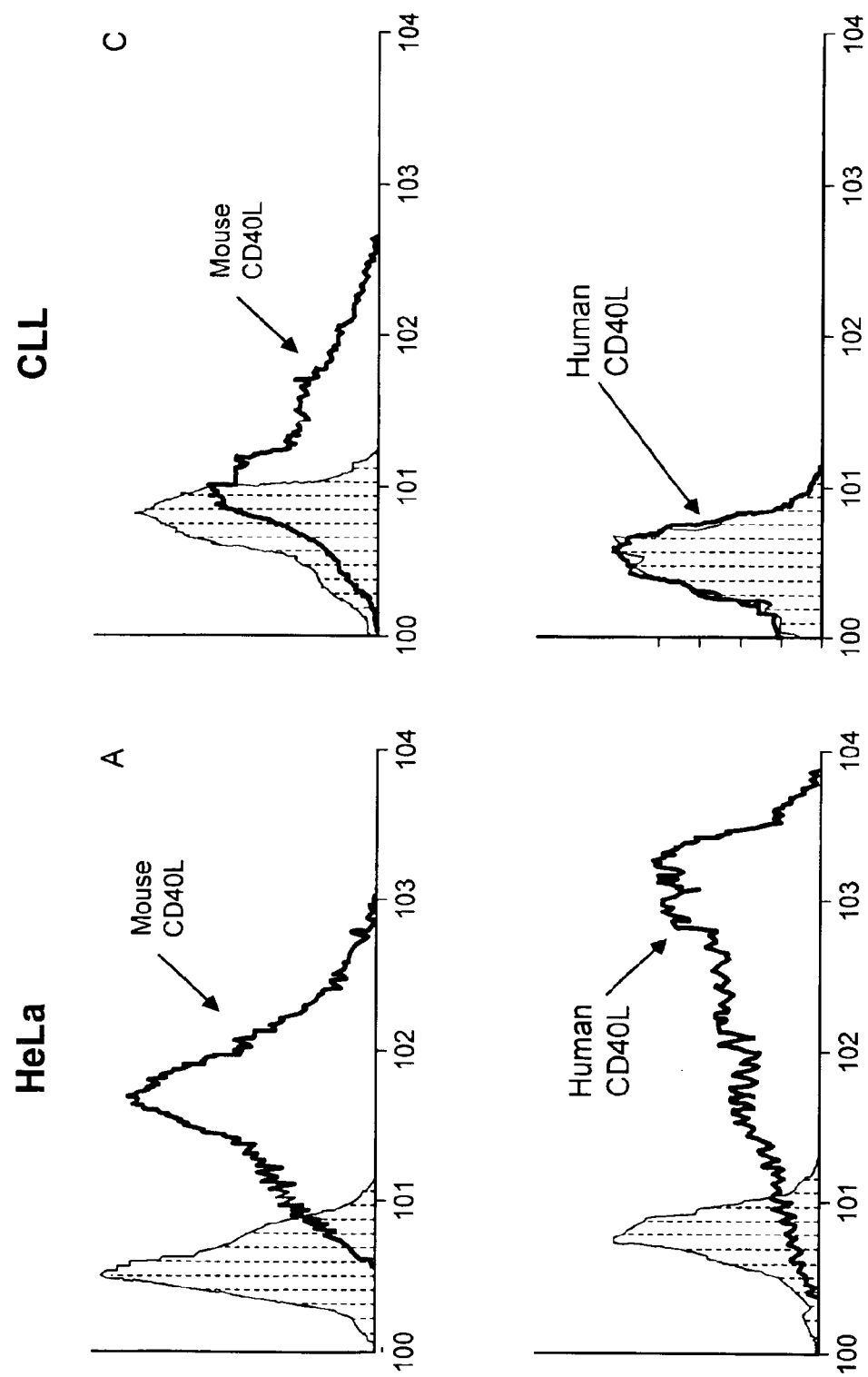
FIG. 3.

The histograms, generated for the CLL cells and HeLa cells containing either a genetic vector containing the human CD40 ligand gene or the murine CD40 ligand gene and the appropriate controls, are shown in FIG. 3A–3D. The expression of both the murine and human accessory molecule ligand gene (CD40 ligand) in HeLa cells is shown in FIGS. 3A and 3B, respectively. The expression of the murine and human accessory molecule ligand in CLL cells is shown in FIGS. 3C and 3D. The expression of an accessory molecule ligand gene in CLL cells and the expression of murine CD40 ligand on the surface of the CLL cells is shown in FIG. 3C. The failure of the human accessory molecule ligand to be expressed on the surface of the CLL cells is shown in FIG. 3D.

Figure 8:
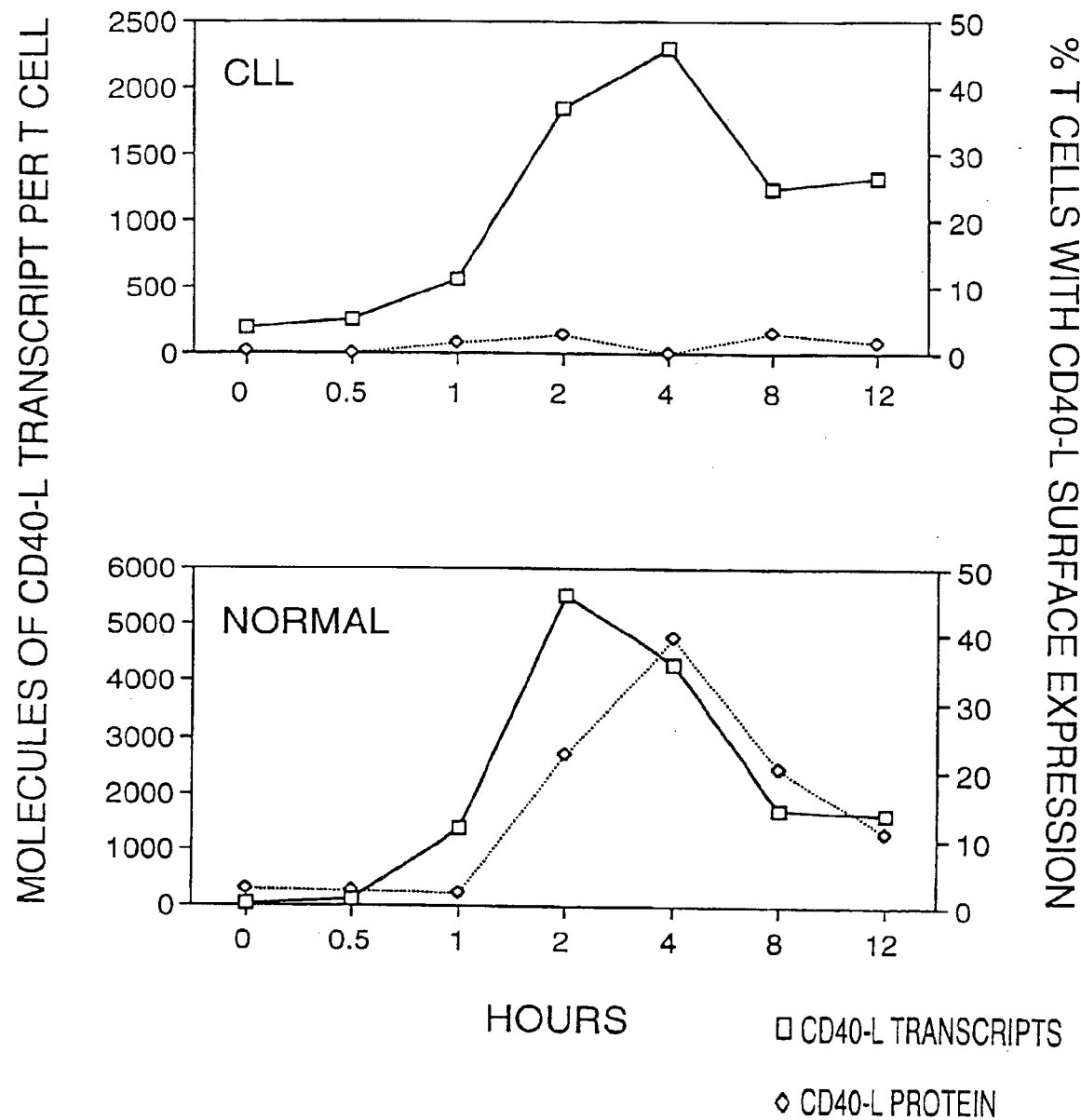
FIG. 8.

FIG. 8 shows data from an experiment done to examine whether the CD4$^+$ T cells of CLL patients could be induced to express the accessory molecule ligand mRNA after CD3 ligation. An ELISA-based quantitative competitive RT-PCR was used to measure CD40 ligand transcript levels. In this experiment, CD40 ligand and RNA transcribed from the CD40 ligand gene in CLL cells are compared with levels of CD40 ligand and RNA made in normal donor cells, after induction by CD3 ligation. For CD3 activation, plate coats of CD3 mAb were made and incubated with plated CLL or normal donor mononuclear cells for the indicated amount of time, after which cells were analyzed for expression of surface antigens or CD154 RNA message levels. CLL or normal donor serum was added to the cells at the beginning of the activation assay for examination of modulation of CD40 ligand surface expression.

For quantitative CD154 RT-PCR ELISA, total RNA was extracted and competitor RNA was generated from the insert containing CD40 ligand (CD154) cDNA. Varying amounts of competitor RNA were added to separate wells of isolated total RNA that subsequently were converted into cDNA. CD3 activation, ELISAs and PCR reactions were performed as described in Cantwell, M. et al., *Nature Medicine* 3:984–989 (1997). Biotinylated PCR products were captured onto microtiter plates (Becton Dickinson, Oxnard, Calif.) coated with streptavidin (Sigma), and incubated. The plate was treated with NaOH to remove the sense strands and subsequently washed. The DNA was then hybridized with either wild-type gene-specific or competitor-specific oligonucleotides. Using terminal transferase, each probe was labeled with a molecule of digoxigenin-11-dideoxyUTP (Boehringer Mannheim). The plate was incubated and washed with HYBE buffer and blocking buffer, then peroxidase-conjugated anti-digoxigenin antibody (150 U/ml; Boehringer Mannheim) in blocking buffer was added. TMB (tetramethylbenzidine) and peroxidase (Kirkegaard and Perry Laboratories, Gaithersburg, Md.) were added for color development, and optical densities were measured at 450 nm and Deltasoft II (Biometallics, Princeton, N.J.) was used for data analysis.

Standard curves plotting the moles of RNA product versus the optical density were made for the standard cDNA reactions. The equations describing these standard curves were then used to calculate the moles of wild-type or competitor DNA present in the unknown PCR reactions based on the optical densities obtained in the ELISA readings. The radio of the quantity of wild-type DNA to the amount of competitor DNA was then plotted against the known quantity of competitor RNA added in the initial samples. The ratio of 1 was taken for the extrapolation of the amount of unknown moles of target RNA in the sample (a ratio of 1 means the amount of target RNA versus competitor RNA are equal). The molecules of target RNA per CD4 cell was then calculated based on the following formula: [(mole target CD154 RNA)×($6\times10^{23}$ molecules/mole)×(dilution factor of test RNA)]/(% of CD4 T cells in total cell population).

The upper graph in FIG. 8 shows that T cells of patients with CLL do not express detectable CD40 ligand after CD3 ligation. CD40 ligand RNA is produced, but it is not stable. Although both CD40 ligand and CD40 ligand RNA are expressed in normal donor T cells (lower graph), the levels of neither the protein or RNA are stably maintained.

Figure 9:
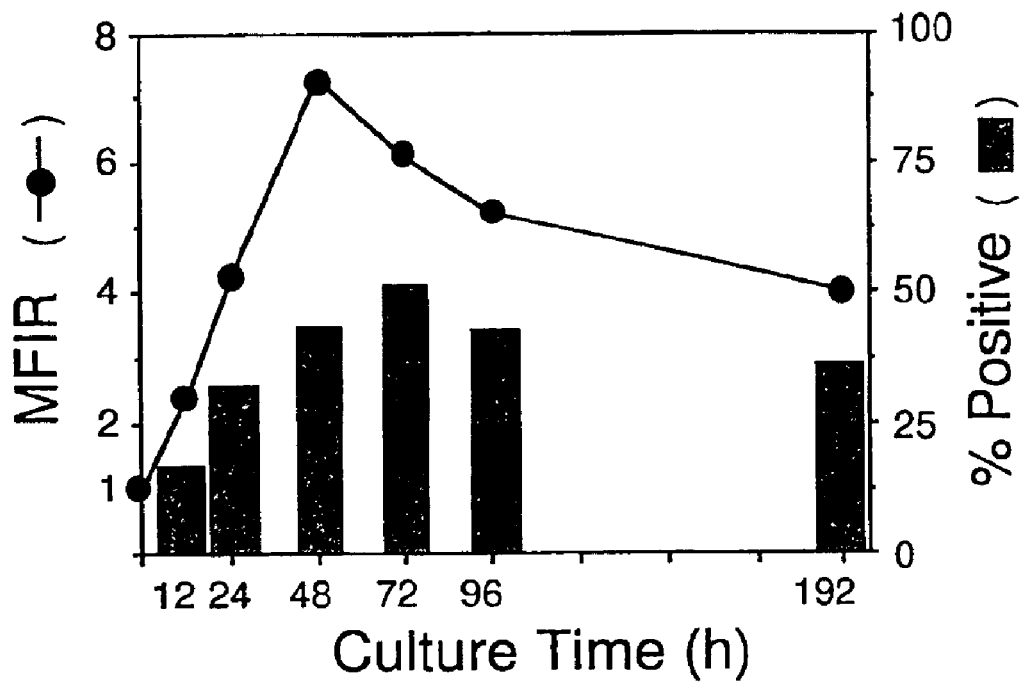
FIG. 9.

FIG. 9 shows a time course for surface expression of CD40 ligand. Expression reached a peak level at 48 hours after infection and persisted at high levels for at least 6 days thereafter. In this experiment, CLL B cells were infected with a gene therapy vector containing an accessory molecule ligand, at a MOI of 1000 at time zero, and then assessed by flow cytometry at a various times thereafter. At each time point listed on the abscissa, the proportions of viable CLL B cells that expressed detectable CD154 are indicated by the vertical bars corresponding to the percentage scale depicted on the right-hand ordinate.

d. Function of the Human and Murine Accessory Molecule Ligands i. Induction of CD80 and CD54 on Cells Containing a Gene Therapy Vector Encoding an Accessory Molecule The CLL cells infected with the murine accessory molecule ligand gene prepared in Example 1b. were then cultured in tissue culture plates. The CLL cells were then analyzed using multiparameter FACS analysis to detect induction of CD80 and CD54 expression using fluorescein isothiocyanate-conjugated monoclonal antibodies immunospecific for each of these respective surface antigens. Non-infected CLL cells were used as a control. The cells were subjected to the appropriate FACS analysis and histograms were generated. CD80 mAb was obtained from Dr. Edward Clark and CD54 mAb was purchased from CALTAG Inc. The CD80 was conjugated using standard methods which have been described in Kipps et al., *Laboratory Immunology II*, 12:237–275 (1992).

Figure 4:
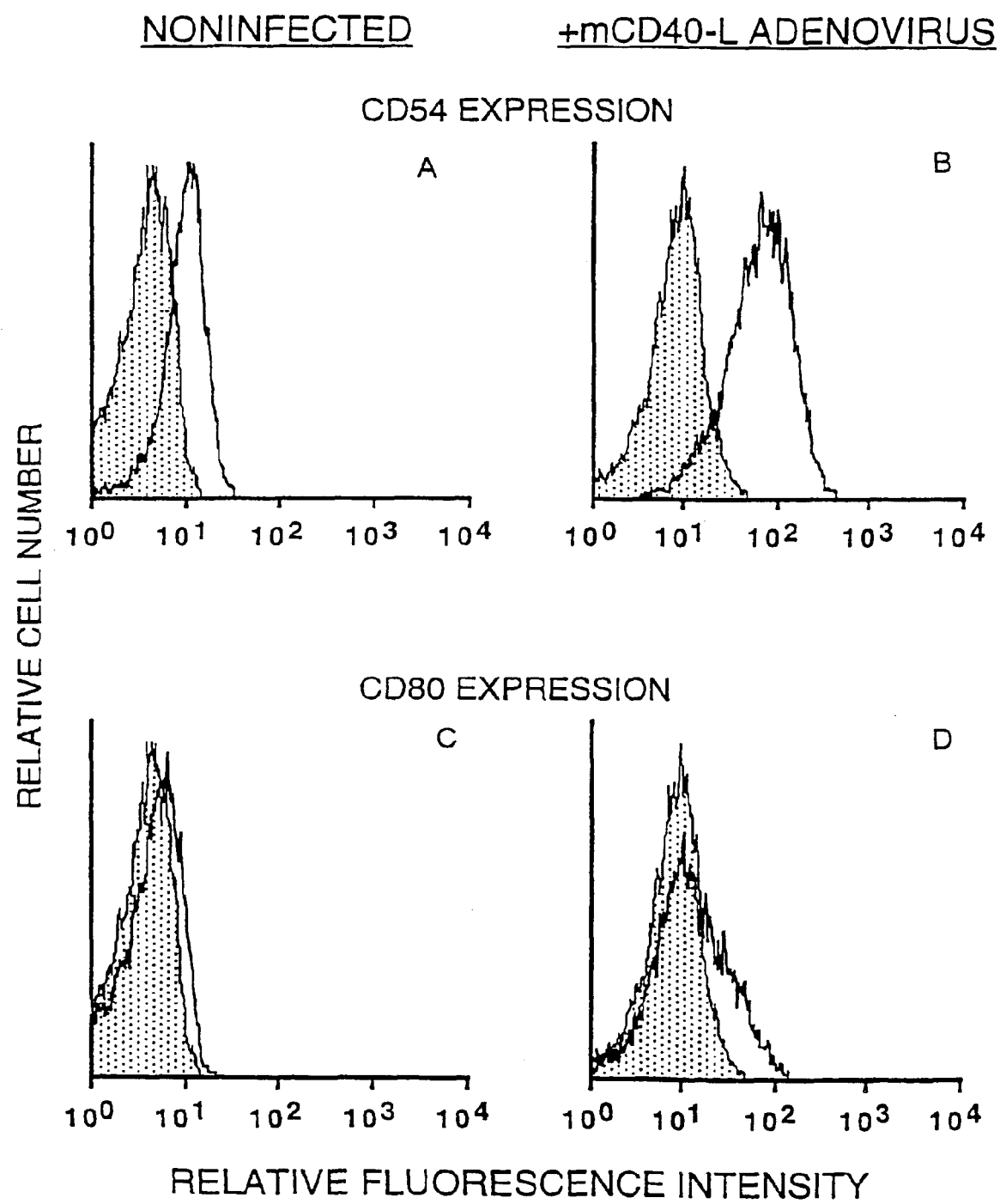
FIG. 4.

The results of this analysis are shown in FIG. 4A–4D. FIGS. 4A–4B compare the amount of CD54 expression in CLL cells which have not been transfected (FIG. 4A) or CLL cells into which a gene therapy vector containing the murine CD40 ligand gene was introduced (FIG. 4B). The shaded graph indicates the isotype control for FACS staining and the open graph indicates the cells stained with the anti-CD54 antibody. These results show that the level of expression of CD54 is increased in CLL cells into which the gene therapy vector containing the murine CD40 ligand was introduced.

FIGS. 4C and 4D compare the amount of CD80 expression in CLL cells which have not been transfected (FIG. 4C) or CLL cells into which a gene therapy vector containing the murine CD40 ligand gene was introduced (FIG. 4D). The shaded graph indicates the isotype control for FACS staining and the open graph indicates the cells stained with the anti-CD80 antibody. These results show that the level of expression of CD80 is increased in the CLL cells into which the gene therapy vector containing the murine CD40 ligand was introduced.

Figure 10:
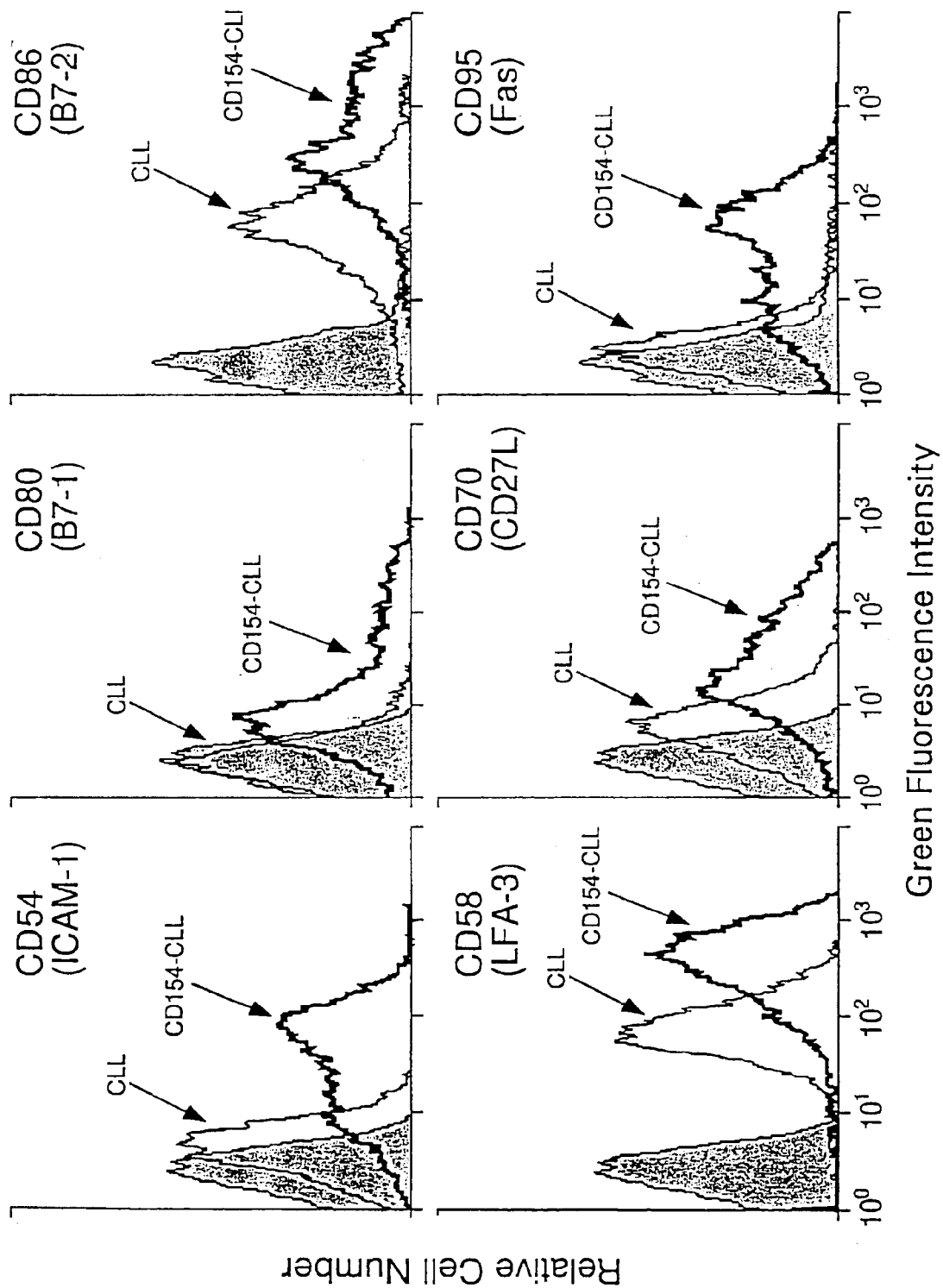
FIG. 10.
Figure 11:
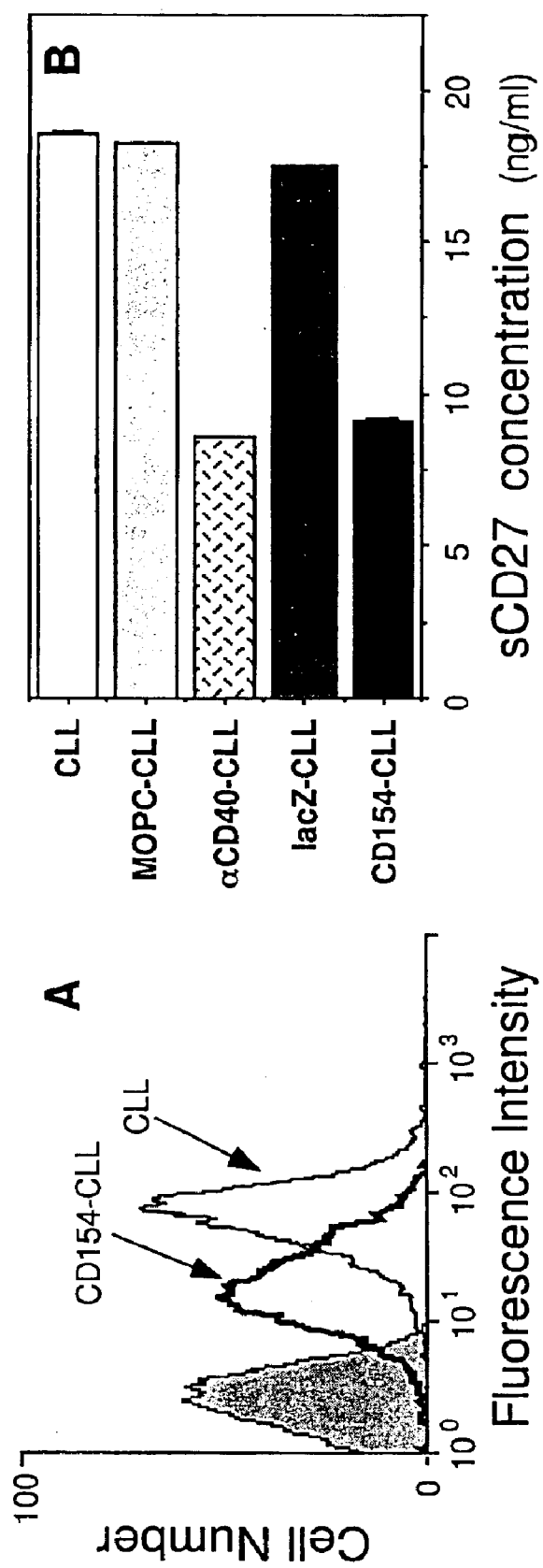
FIG. 11.

In an additional experiment, CLL cells infected with a gene therapy vector containing the murine accessory molecule ligand gene were evaluated by flow cytometry for induced expression of not only CD54 and CD80, but also CD86, CD58, CD70 and CD95. Fluorescein-conjugated mAb specific for human CD54 and CD70 were purchased from CALTAG. Fluorescein-conjugated mAb specific for human CD27, CD58, CD80, CD86, or CD95, and phycoerythrin-conjugated mAb specific for human or mouse CD40 ligand, were obtained from PharMingen. Shaded histograms represent staining of CLL B cells with FITC-conjugated isotype nonspecific mAb. In contrast to uninfected CLL cells (FIG. 10, thin-lined histograms), or Ad-lacZ-infected CLL cells (data similar to that obtained with uninfected cells, but not shown), CLL cells infected with the adenovirus vector encoding the CD40 ligand (CD154) expressed high levels of CD54 (FIG. 10, top left), CD80 (FIG. 10, top middle), CD86 (FIG. 10, top right), CD58 (FIG. 10, bottom left), CD70 (FIG. 10, bottom middle), and CD95 (FIG. 10, bottom right). On the other hand, CD40 ligand-CLL (CD154 CLL) expressed significantly lower levels of both surface membrane CD27 (FIG. 11A, thick-lined histogram) and soluble CD27 (FIG. 11B) than uninfected (FIG. 11A, thin-lined histogram) ($P<0.01$, Bonferroni t-test) or Ad-lacZ-infected CLL cells (data similar to that obtained with uninfected cells, but not shown). In the experiment shown in FIG. 11A, the CLL B cells were examined for expression of CD27 via flow cytometry, three days after infection. Shaded histograms represent staining of CLL B cells with FITC-conjugated isotype control mAb. In FIG. 11B, cell-free supernatants were collected, after the infection or stimulation of CLL B cells, for 72 hours and tested for the concentration of human CD27 by ELISA. The reduced expression of CD27 (FIG. 11B) is similar to that noted for leukemia B cells stimulated via CD40 cross-linking with aAb G28-5 presented by CD32-expressing L cells, as described in Rassenti, L. Z. and T. J. Kipps, *J. Exp. Med.* 185:1435–1445.

ii. Allogeneic T Cell Responses to CLL Cells Into Which a Genetic Therapy Vector Containing a Murine CD40 Ligand Gene Has Been Introduced The ability of CLL cells which have been inflected with a gene therapy vector containing the murine CD40 ligand gene to stimulate allogeneic T cells (i.e., from another individual) was analyzed using cell proliferation assays. Briefly, the test cells were co-cultured with the genetic therapy vector containing the lac-Z gene or the murine CD40 ligand gene at a multiplicity of infection of 1,000 in the presence of IL-4 at a concentration of 10 ng/ml. In other samples, the CLL cells were stimulated with MOPC21 (a control IgG) or G28-5 (an anti-CD40 monoclonal antibody) or were preincubated on CD32-L cells and at the same time treated with IL-4. The preincubation with the CD32-L cells together with IL-4 treatment have been shown to be an efficient form of cross-linking the CD40 molecule other than direct gene transfection.

Figure 5:
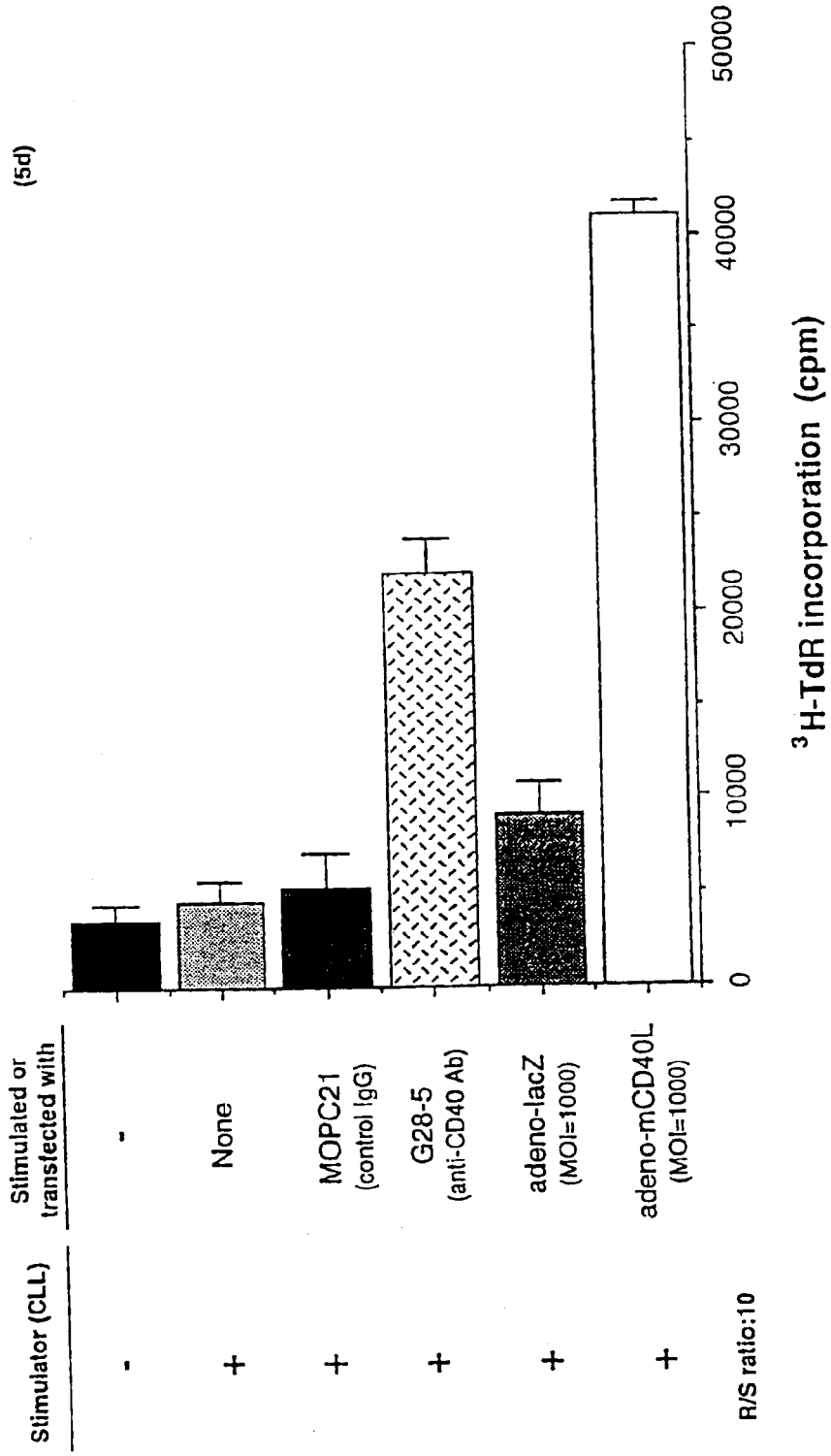
FIG. 5.

After these days of culture at 37° C., these cells were treated with mitomycin C to prevent their proliferation and then used to stimulate allogeneic T cells. Prior to this co-culture, the different aliquots of CLL cells had either been treated with the anti-CD40 monoclonal antibody or had been infected with the gene therapy vector containing either the lac-Z or murine CD40 ligand gene at a stimulator ratio of 1:10. After two days of culture at 37° C., interferon gamma (IFNγ) production was measured by ELISA assay. After five days of co-culture at 37° C., the incorporation of $^3$H-thymidine into replicating cells was measured after an eight hour pulse label. The results of this assay are shown in Table II below and in FIG. 5.

In another experiment, CLL B cells infected with the gene therapy vector containing the CD40 ligand gene were evaluated for their ability to act as stimulator cells in an allogeneic mixed lymphocte T cell reaction (MLTR). In parallel, the stimulatory capacity of control lac-Z-vector-infected CLL cells and CLL B cells that had been cultured with Cd32-L cells and an anti-CD40 mAb (G28-5) or an isotype control Ig, was also examined as described in Ranheim, E. A. and T. J. Kippa, *J. Exp. Med.,* 177:925–935 (1993), Clark, E. A. and J. A. Ledbetter, *Proc. Natl. Acad. Sci. USA,* 83:4494–4498 (1986), and Banchereau, J. et al., *Science* 251:70–72 (1991). Effector T cells from a non-related donor were co-cultured with the CLL stimulator cells at an effector to target ratio of 4:1. After 18 h culture at 37° C., over 30% of the allogeneic CD3$^+$ cells were found to express the activation-associated antigen CD69 when cultured with CD154-CLL cells (data not shown). In contrast, less than 4% of the T cells expressed CD69 when co-cultured with uninfected or Ad-lacZ-infected CLL cells (data not shown).

Two days after the initiation of the MLTR, the concentrations of IFNγ in the culture supernatants were assayed by ELISA. The supernatants of the MLTR stimulated with CLL cells infected with the accessory molecule ligand CD40L (FIG. 12A, CD154-CLL) contained significantly higher levels of IFNγ (306±5 ng/ml, m±SE, n=3) than that of MLTR cultures stimulated with the anti-CD40 mAb (FIG. 12A, αCD40-CLL) (23±3 ng/ml) (P<0.05, Bonferroni t-test). The latter was not significantly different from that of MLTR cultures stimulated with control Ad-lacZ-infected CLL cells (FIG. 12A, lacZ-CLL) (43±10 ng/ml) (P>0.1, Bonferroni t-test). The supernatants of effector cells alone, or of MLTR cultures stimulated with uninfected CLL cells (FIG. 12A, CLL) or control Ig treated CLL cells (FIG. 12A, MOPC-CLL), did not contain detectable amounts of IFNγ(<2 ng/ml). Similarly, none of the leukemia B cell populations produced detectable amounts of IFNγ when cultured alone, without added effector T cells (data not shown).

Figure 12:
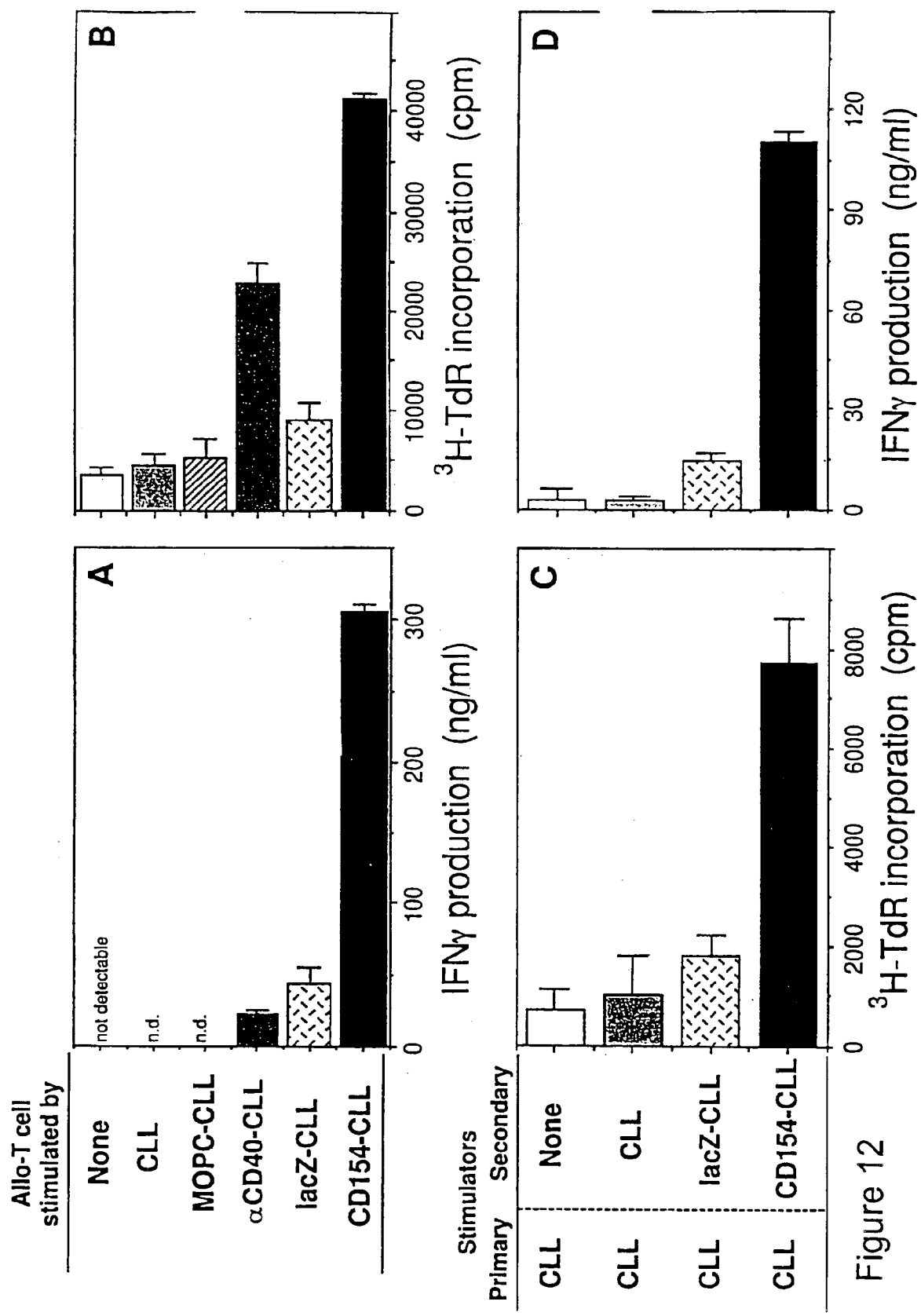
FIG. 12.

After 5 days, cell proliferation was assessed by incorporation of $^3$H-thymidine. Cultures with isotype control IgG-treated (FIG. 12B, MOPC-CLL) or uninfected (FIG. 12B, CLL) stimulator cells did not incorporate more $^3$H-thymidine than cultures without added leukemia-stimulator cells (FIG. 12B, None). Ad-lacZ-infected CLL B cells (FIG. 12B, lacZ-CLL) also were unable to stimulate allogeneic T cells to incorporate amounts of $^3$H-thymidine that were much greater than that of control cultures. In contrast, anti-CD40-stimulated leukemia cells or CD154-CLL cells each induced significant effector cell proliferation (FIG. 12B, αCD40-CLL or CD154-CLL) (P<0.05, Bonferroni t-test). Moreover, the amount of $^3$H-thymidine incorporated by cultures stimulated with CD154-CLL cells (41, 004±761 cpm (m±SE), n=3) was significantly greater than that of cultures stimulated with equal numbers of αCD40-CLL cells (22,935±1,892 cpm; n=3) (P<0.05, Bonferroni t test). However, neither of these mitomycin-C-treated leukemia cell populations incorporated $^3$H-thymidine when cultured without effector T cells (data not shown). Also, as described for the MLTR between allogeneic T cells and CD40-stimulated CLL cells {6549, 71676, 7168,}, allogeneic T cell proliferation in response to CD154-CLL could be inhibited by CTLA-4-Ig or CD11a mAb when added at the initiation of the MLTR, indicating that respective interactions between CD80/CD86 and CD28, or CD54 and CD11a/CD18, contribute to the noted allogeneic T cell reaction (data not shown).

TABLE II

Allogeneic T cell responses to CLL cells infected with mCD40-L adenovirus

| | % positive cells | | Allogeneic response (mean ± SEM) | |
|---|---|---|---|---|
| Stimulators | mCD40-L | Human CD80 | 3H-TdR uptake (cpm) | IFNy production (ng/ml) |
| None (t cells only) | — | — | 3577 ± 821 | n.d.* |
| CLL with: | | | | |
| No activation | 0 | 1.4 | 4577 ± 1097 | n.d. |
| MOPC21 | 0 | 1.0 | 5259 ± 1788 | n.d. |
| G28-5 | 0 | 26.7 | 22935 ± 1892 | 22.3 ± 1.6 |
| lac-Z adeno | 0 | 4.8 | 9037 ± 1781 | 43.2 ± 10.5 |
| mCD40-L adeno | 17.5 | 19.7 | 41004 ± 761 | 305.7 ± 4.5 |

Figure 6:
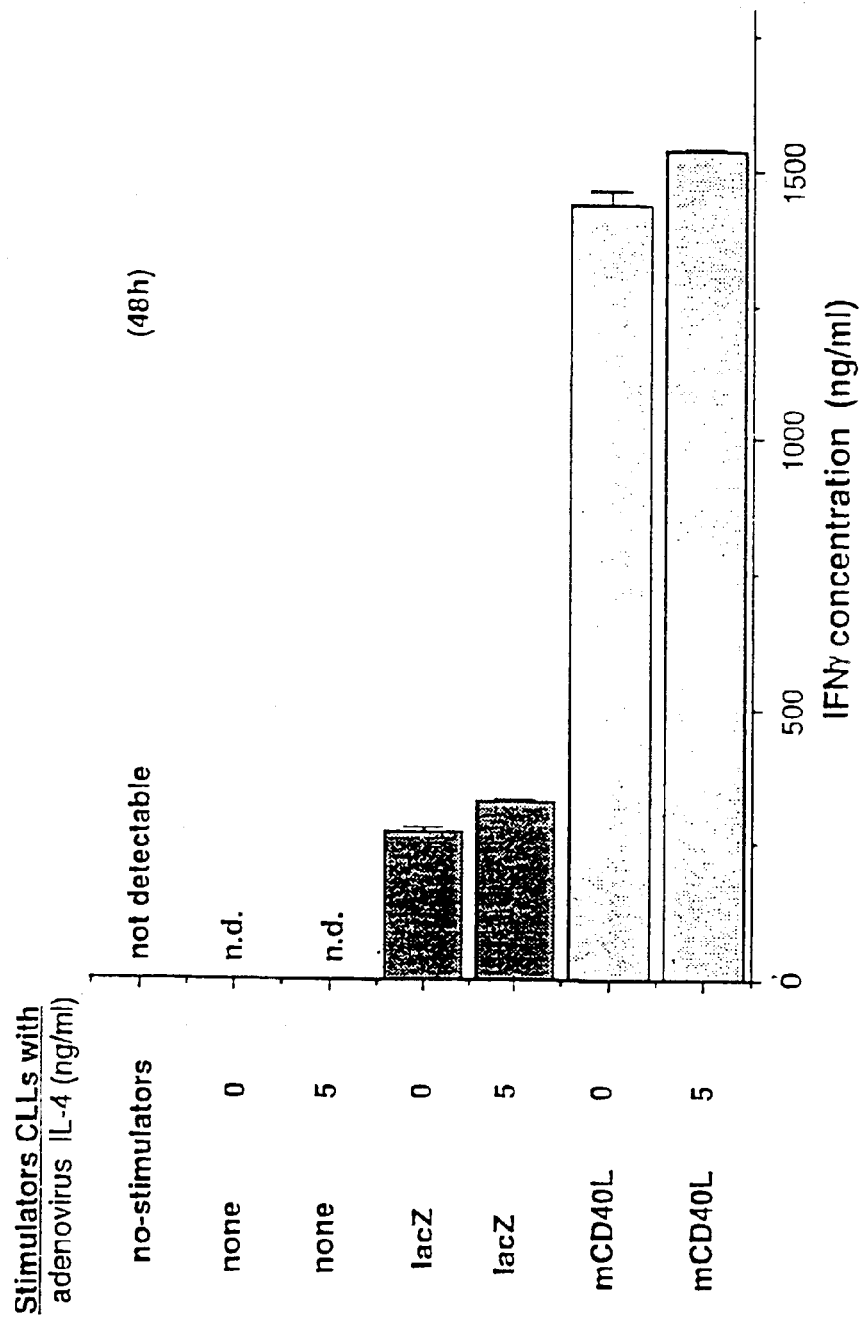
FIG. 6.

*n.d. - not detectable iii. Stimulation of Gamma Interferon by CLL Cells Containing an Accessory Molecule Ligand Gene The function of CLL cells containing an accessory molecule ligand gene (mouse CD40 ligand) was analyzed by determining the ability of those cells to activate T lymphocytes. The procedure was performed as follows: allogeneic T lymphocytes from a healthy donor (greater than 90% CD3$^+$) were purified using magnetic beads and monoclonal antibodies specific for the Cd14 and CD19 antigen. These allogeneic T lymphocytes then were cultured together with MMC-treated CLL cells which were infected with the accessory molecule ligand gene (murine CD40 ligand) or the lac-Z gene. This co-culture was performed in RPMI-1640 medium containing 10% fetal calf serum. After culture for 24 hours, the cells were collected and analyzed to determine the expression of the antigen CD69 on the T lymphocytes using a standard FACS sorting protocol. The cell culture supernatants were collected after two days in culture and tested to determine the concentration of human interferon gamma using an ELISA assay. A portion of the CLL cells containing an accessory molecule ligand gene (murine CD40 ligand) and a portion of the cells containing the adenovirus expressing the lac-Z were cultured in the presence of human interleukin 4 IL-4 (5 ng/mL). The production of interferon gamma by allogeneic T lymphocytes in the presence of this amount of human interleukin 4 was also analyzed. The results from these analyses are shown in FIG. 6.

Figure 13:
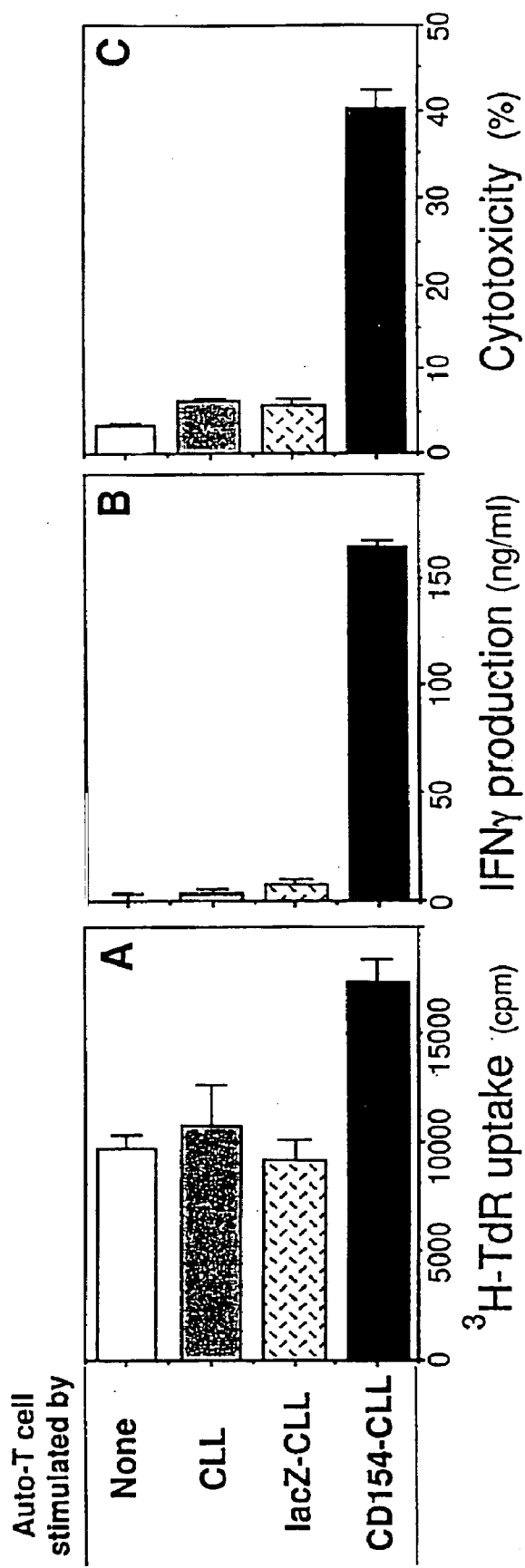
FIG. 13.

As can be seen, the human CLL cells containing the accessory molecule ligand gene (murine CD40) produced substantially higher concentrations of interferon gamma in the cell culture supernatant when compared to CLL cells which contained the lac-Z gene. The increased production of interferon gamma (IFNγ) by T lymphocytes exposed to CLL cells containing the accessory molecule ligand gene indicates that these CLL cells containing the accessory molecule ligand genes were effective in producing an enhanced immune response.

iv. Stimulation of Allogeneic T Cells Pre-Exposed to Non-Modified CLL B Cells Containing an Accessory Molecule Ligand Gene Prior Studies indicated that antigen presentation to T cells, in the absence of the signals derived from costimulatory molecules such as CD28, can lead to specific T cell clonal anergy. For this reason, allogeneic T cells that had previously been cultured, with non-modified CLL B cells lacking expression of CD80 and other immune accessory molecules, were tested for their ability to respond to CLL cells containing the CD40 ligand gene. Allogeneic effector cells did not incorporate more $^3$H-thymidine in response to non-modified CLL cells (FIG. 12C, cLL), or control CLL cells infected with Ad-lacZ (FIG. 12C, lacZ-CLL), than when they were cultured alone (FIG. 12C, None). In contrast, even after prior co-culture with non-modified CLL B cells, allogeneic effector cells could still be induced to proliferate (FIG. 12C, CD154-CLL) or to produce IFNγ (FIG. 12D, CD154CLL) in response to cells expressing an accessory molecule ligand. Although modest amounts of IFNγ were detected in the supernatants of such secondarycultures when Ad-lacZ-infected leukemia cells were used as stimulator cells (FIG. 12D, lacZ-CLL), this level was significantly lower than that noted for secondarycultures with Ad-CD40-ligand-infected CLL cells (FIG. 12D, CD154-CLL) (P<0.05, Bonferroni t-test). Similarly, the supernatants of the leukemia cells alone (data not shown), and the effector cells alone (FIG. 12D, None), of the MLTR cultures stimulated with uninfected CLL Cells (FIG. 12D, CLL), contained negligible amounts of IFNγ (<2 ng/ml). These results indicate that allogeneic effector cells cultured with nonmodified CLL B cells are not precluded from responding to CLL B cells infected with a gene therapy vector containing the accessory molecule ligand gene.

v. Autologous T Cell Responses to CLL Cells Into Which a Gene Therapy Vector Encoding a Murine Accessory Molecule Ligand Gene Has Been Introduced T cells isolated from the blood of CLL patients were examined for their ability to respond in vitro to autologous CLL B cells containing a gene therapy vector which encodes the murine accessory molecule, CD40 ligand. T cells were isolated to >95% purity, and then co-cultured with mitomycin-C-treated autologous leukemia cells in serum-free AIM-V medium supplemented with exogenous interleukin-2 at 25 U/ml. Modest $^3$H-thymidine incorporation ($\leq$10,000 cpm) was detected in cultures without added stimulator cells, secondary in part to the exogenous IL-2 (FIG. 13A, and data not shown). The level of T cell proliferation, however, did not increase in response to uninfected CLL cells (FIG. 13A, CLL) or Ad-lacZ-infected CLL cells (FIG. 13A, lacZ-CLL). In contrast, CLL cells infected with a gene therapy vector containing the accessory molecule ligand (FIG. 13A, CD154-CLL) induced autologous T cells to incorporate significantly more $^3$H-thymidine (17,368±1,093 cpm, n=3) than any of the control cultures (P<0.05, Bonferroni t-test). Furthermore, the MLTR stimulated with CLL cells infected with a vector encoding an accessory molecule ligand (CD40L) also generated significantly more IFNγ (165±3 ng/ml, n=3) than any of the other cultures (FIG. 13B) (P=0.05, Bonferroni t-test).

Figure 14:
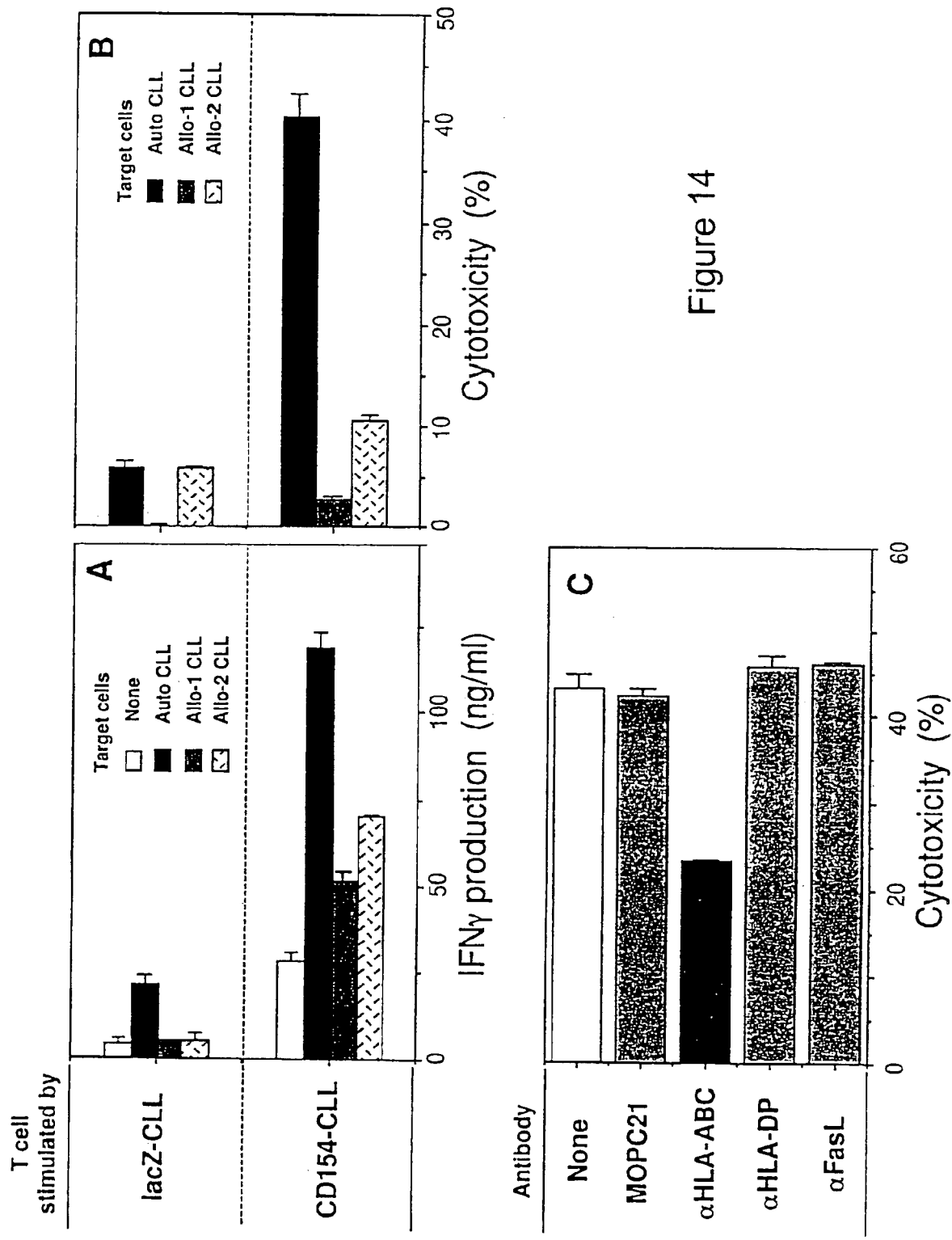
FIG. 14.
Figure 15:
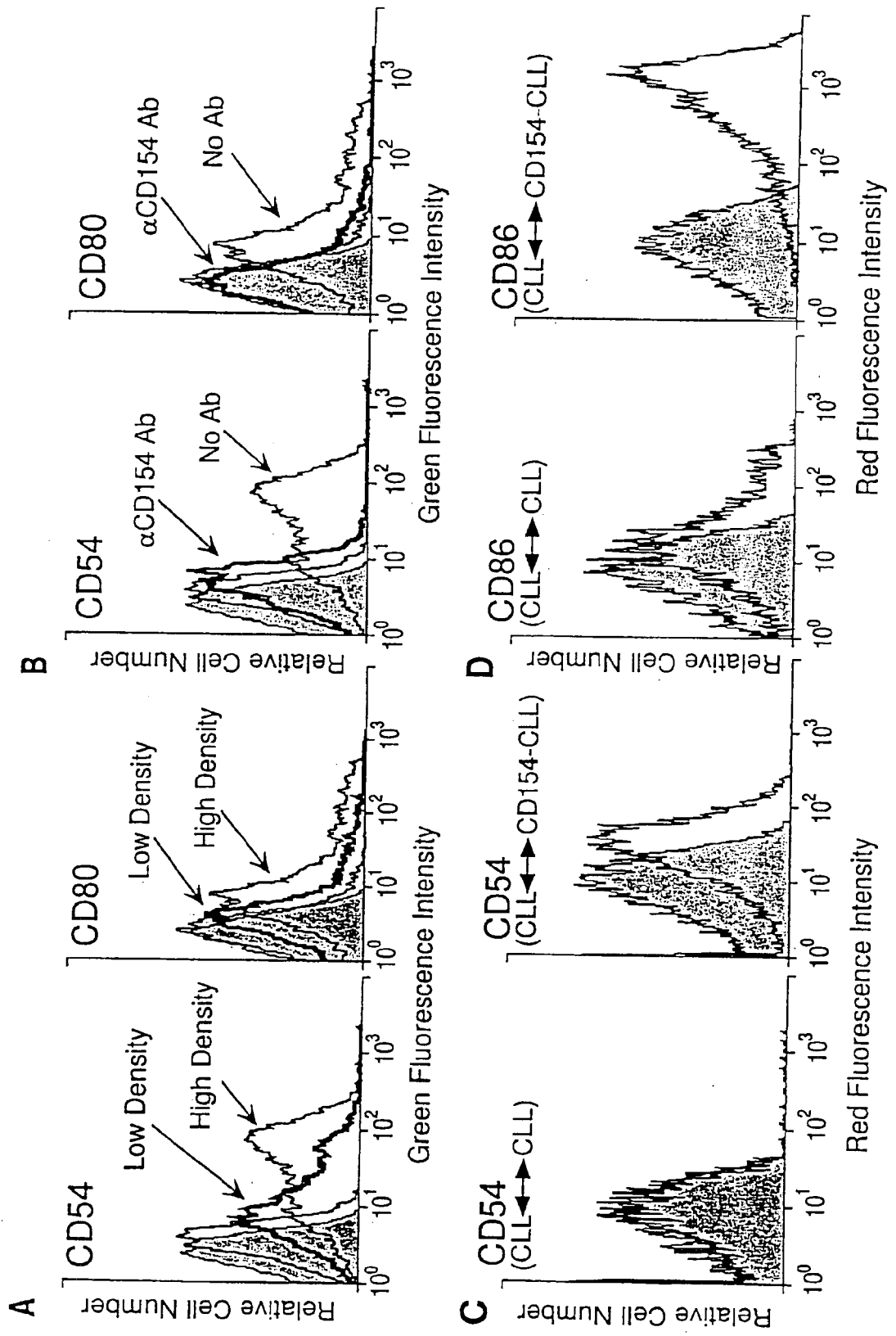
FIG. 15.

The T cells were harvested after 5 days from the autologous MLTR and assessed for CTL activity against autologous CLL B cells. T cells co-cultured with autologous CD40-ligand-CLL cells developed CTL activity for non-modified CLL B cells, effecting 40.1% lysis (±2.3%) at an E:T ratio of 2:1 (FIG. 13C, CD154). However, such T cells did not develop detectable CTL activity for the same target cells in the control reactions, when co-cultured with uninfected or Ad-lacZ-infected CLL cells (FIG. 13C).

vi. Specificity of CTL Stimulated by Autologous CD40-Ligand-CLL B Cells for Allogeneic CLL B Cells Effector cells stimulated with autologous CD40-ligand-CLL were evaluated for their ability to secrete IFNγ or manifest CTL activity against allogeneic CLL B cells (FIG. 14). After 5 days of autologous MLTR with CD154-CLL or lacZ-CLL, T cells were isolated by Ficoll density gradient centrifugation, washed extensively, and then cultured in media for 24 h. Washed T cells were mixed with autologous ("Auto CLL", solid bar) or allogeneic ("Allo-1 CLL" or "Allo-2 CLL", shaded or hatched bars) target CLL B cells. T cells stimulated in the autologous MTLR with CD40-ligand-CLL cells, but not with lacZ-CLL cells, produced significantly more IFNγ in response to secondary culture with non-modified autologous CLL B cells than will allogeneic CLL B cells (FIG. 14A) (P<0.05, Bonferroni t-test). Furthermore, T cells stimulated with CD40-ligand-CLL cells, but not with lacZ-CLL cells, were cytotoxic for autologous CLL cells, but not allogeneic CLL cells (FIG. 14B). Similar results were obtained with the autologous MLTR-activated T cells of the allogeneic donor, again demonstrating specific cytotoxicity for autologous CLL B cells (data not shown). Finally, W6/32, a mAb to class I major histocompatibility complex (MHC I) antigens could significantly inhibit the cytotoxicity of T cells stimulated with CD40-ligand-CLL cells for autologous CLL B cells (FIG. 14C, αHLA-class I)) (P<0.05, Bonferroni t-test). Such inhibition was not observed with mAb specific for MHC class II antigen (FIG. 14C, αHLA-DP), mAb specific for the Fas-ligand (FIG. 14C, αFasL), or an isotype control mAb of irrelevant specificity (FIG. 14C, MOPC-21). Collectively, these studies indicate that Ad-CD40-ligand-infected CLL cells can induce an autologous anti-leukemia cellular immune response in vitro, leading to the generation of MHC-class I-restricted CTL specific for autologous non-modified leukemia B cells.

e. Transactivation of Non-Infected Bystander Leukemia B Cells by Ad-CD40L CLL Cells To address whether the changes in tumor marker expression (described in section 1d.) resulted from intracellular versus intercellular stimulation, the effect of culture density on the induced expression of CD54 and CD80 following infection with adenovirus gene therapy vector encoding the accessory molecule ligand (CD40L, or CD154) was examined. After infection, CLL cells were cultured at standard high density (e.g. $1\times10^6$ cells/ml) or low density (e.g. $2\times10^5$ cells/ml) for 3 days at 37° C. Cells plated at high density contained homotypic aggregates, whereas cells plated at low density remained evenly dispersed and without substantial cell-cell contact (data not shown). Despite expressing similar levels of heterologous CD154, CD154-CLL B cells cultured at high density were induced to express higher levels of CD54 and CD80 than CD154-CLL cells cultured at low density (FIG. 15A). The stimulation achieved at high density could be inhibited by culturing the cells with a hamster anti-mouse CD154 mAb capable of blocking CD40<–>CD154 interactions (FIG. 15B, αCD154 Ab). Collectively, these studies indicate that CD154-CLL cells can activate each other in trans and that surface expression of CD154 is necessary for optimal leukemia cell stimulation.

Figure 24:
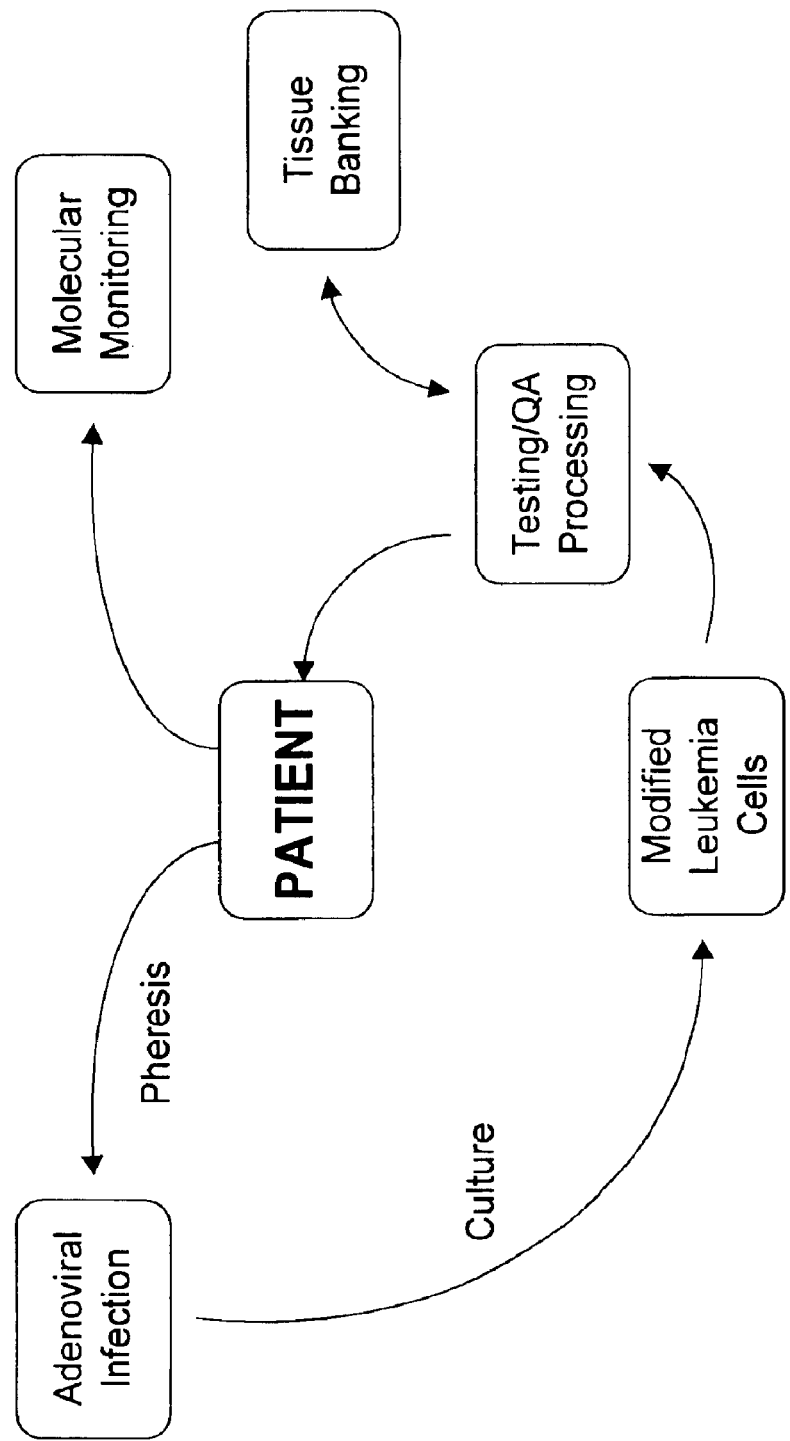
FIG. 24.

In addition, Ad-CD154-infected, uninfected, Ad-lacZ-infected, or G28-5-stimulated CLL cells were labeled with a green-fluorescence dye to examine whether CD154-CLL could stimulate non-infected bystander leukemia cells. Dye-labeled cells were used as stimulator cells for equal numbers of non-labeled syngeneic CLL B cells. After 2 days' culture, stimulator cells cultured by themselves retained the green-fluorescence dye, allowing such cells to be distinguished from non-labeled CLL cells by flow cytometry. Bystander (green-fluorescence-negative) $CD19^+$ CLL B cells were induced to express CD54 (FIG. 15C, right histogram) or CD86 (FIG. 15D, right histogram) when co-cultured with Ad-CD154-infected leukemia B cells, but not with mock infected CLL cells (FIGS. 15C and 15D, left histograms), G28-5-stimulated CLL cells, or Ad-lacZ-infected CLL cells (data not shown). As expected, these bystander (green-fluorescence-negative) CLL cells also were negative for heterologous CD154.

f. Treatment of Leukemia with Gene Therapy Vectors Encoding an Accessory Molecule Ligand FIG. 24 shows an outline for a clinical trial for testing treatment of B cell CLL with adenovirus gene therapy vectors encoding modified CD40 ligand. Leukemia cells harvested by pheresis are infected with replication-defective vectors that encode the modified CD40 ligand. Following expression of this protein, the cells will be administered back to the patient for the purpose of stimulating a host anti-leukemia-cell immune response. This strategy is far superior to one that uses gene therapy to affect expression of only one immune stimulatory molecule on the leukemia cell surface. Indded, this strategy results in the leukemia cells expressing an array of immune-stimulatory accessory molecules and cytokines, as well as a molecule that can affect the same changes in leukemia cells of the patient that were never harvested.

2. Expression of Chimeric Accessory Molecule Ligand Genes

The chimeric accessory molecule ligand genes described below are prepared using standard techniques as described herein.

a. Preparation of Chimeric Accessory Molecule Ligand Genes Utilizing Domains from Two Different Accessory Molecule Genes The human CD40 ligand gene was isolated from RNA prepared from T cells which had been activated by an anti-CD3 monoclonal antibody using 5' and 3' primers together with well known PCR methods. Chimeric accessory molecule genes of human CD40 ligand and murine CD40 ligand are constructed from the newly cloned human CD40 ligand gene and mouse CD40 ligand gene described herein as SEQ ID NOS:1 and 2. The transmembrane and cytoplasmic domains of human CD40 ligand genes are exchanged with those of the murine CD40 ligand gene and designated H(Ex)-M(Tm-Cy) CD40 ligand. These chimeric accessory molecule ligand genes are produced using the gene conversion technique described as SOEN which has been previously described by Horton, *Mol. Biotechnol.*, 3:93 (1995). A diagram depicting the chimeric accessory molecule ligand genes which are produced is shown in FIG. 2. The nucleotide sequences of each of these respective chimeric accessory molecule ligand genes is designated SEQ ID NOS: 3–7 as indicated in the Table below.

TABLE III

| Chimeric Accessory Molecule Ligand Gene | SEQ ID NO: |
|---|---|
| HuIC/HuTM/MuEX CD40-Ligand | SEQ ID NO: 3 |
| HuIC/MuTM/HuEX CD40-Ligand | SEQ ID NO: 4 |
| HuIC/MuTM/MuEX CD40-Ligand | SEQ ID NO: 5 |
| MuIC/HuTM/HuEX CD40-Ligand | SEQ ID NO: 6 |
| MuIC/MuTM/HuEX CD40-Ligand | SEQ ID NO: 7 |

Adenovirus vectors encoding each of the chimeric accessory molecules shown in FIG. 2 are constructed using the methods described in Example 1. Each of these constructs are then transfected into either HeLa cells or CLL cells according to the methods of Example 1.

b. Expression of Chimeric Accessory Molecule Ligands on CLL and HeLa Cells

The expression of each of the chimeric accessory molecule ligand genes constructed above is analyzed by using FACS analysis as specified in Example 1. The appropriate monoclonal antibody immunospecific for the external domain of either human or mouse CD40 ligand is selected and used to determine the level of expression of the chimeric accessory molecules on the surface of these cells. After appropriate analysis and preparation of appropriate histograms, the expression of chimeric accessory molecules containing at least a portion of the murine CD40 ligand gene is confirmed.

c. Function of Chimeric Accessory Molecule Ligands

CLL cells are infected with various MOI of the mCD40L adenovirus and then cultured in 48 or 24 well tissue culture plates for various times after infection (48, 72, and 96 hours). The CD19$^+$ B cells are then analyzed by multiparameter FACS analysis for induction of CD80 and CD54 expression using fluroescein isothiocyanate-conjugated mAb specific for each respective surface antigen as described in Example 1. Increased amounts of CD54 and CD80 are found on cells which have the chimeric accessory molecules containing the domain or domains derived from the mouse CD40 ligand gene.

Further analysis of the cells containing the chimeric accessory molecule genes is carried out according to Example 1(d). The cells containing the chimeric accessory molecule genes which contain the domains derived from the murine CD40 ligand gene are able to stimulate the production of gamma interferon and T cell proliferation.

d. Expression of Chimeric Accessory Molecule Genes Which Contain Proximal Extracellular Domains from Two Different Accessory Molecules from the Same Species A chimeric accessory molecule ligand gene is prepared which contains the proximal extracellular domain from the human CD70 gene (Domain III) with the remainder of the domains derived from the human CD40 ligand gene. This gene is prepared using standard biologic techniques as previously described herein. This chimeric accessory molecule ligand gene has the DNA sequence shown as SEQ ID NO: 19. A different chimeric accessory molecule ligand gene is prepared which contains the proximal extracellular domain from the murine CD40 ligand gene with the remainder of the domains derived from the human CD40 ligand gene. This gene is prepared using standard techniques as previously described herein. This chimeric accessory molecule ligand gene has the DNA sequence shown as SEQ ID NO: 20.

The chimeric accessory molecule genes shown as SEQ ID NOS: 19 and 20 are inserted into the appropriate vectors as described in Example 1 and introduced into human neoplastic cells. The expression of that chimeric accessory molecule gene in the cells is determined as was described in Example 1.

The chimeric accessory molecule encoded by each of these chimeric accessory molecule genes is found on the surface of the human neoplastic cells using the FACS analysis described in Example 1. Increased amounts of CD54 and CD80 are found on the cells containing the chimeric accessory molecule genes using the techniques described in Example 1. The cells containing the chimeric accessory molecule gene are able to stimulate the production of gamma interferon and T cell proliferation as described and assayed according to Example 1.

3. Augmentation of Vaccination Using Vectors Encoding Accessory Molecules

The following procedures were used to demonstrate the augmentation of a vaccination protocol using a gene therapy vector encoding an accessory molecule.

a. Augmentation of the Antibody Response in Mice Co-Injected with an Accessory Molecule Gene Therapy Vector and placZ Three different gene therapy constructs were prepared using standard techniques including those techniques described herein. The first was a control gene therapy vector, pcDNA3, which did not contain any gene. The second, placZ, contained the Lac-Z gene which encoded β-galactosidase (β-gal). The third, p-mCD40L, contained the murine CD40 ligand gene described in Example 1.

Prior to any immunizations, serum was isolated from 6–8 weeks old BALB/c-mice to determine the amount of any initial antibodies to β-galactosidase. Each animal was injected i.m. with 100 micrograms of plasmid DNA per injection. Four separate injections were given at one week intervals.

Prior to the third injection, the animals were bled to monitor the early antibody response to β-gal. One week after the final injection of plasmid DNA, the animals were bled to monitor the late antibody response to beta-galactosidase. To test the sensitivity of the assay, known amounts of anti-β-gal antibodies isolated from an anti-β-gal antiserum were tested in parallel.

Serum dilutions of 1:40, 1:200, or 1:1000 were tested in an ELISA for anti-β-gal antibodies. For this, polystyrene microtiter ELISA plates were coated with β-gal at 10 microgram/ml in phosphate buffered saline. The plates were washed thrice with blocking buffer containing 1% bovine serum albumin (BSA), 0.2% Tween 20 in borate buffered saline (BBS) (0.1M borate, 0.2M NaCl, pH 8.2). 50 microliters of diluted serum were added to separate wells. After at least 1 hour at room temperature, the plates were washed thrice with blocking buffer and then allowed to react with alkaline phosphatase-conjugated goat anti-mouse IgG antibody. One hour later, the plates again were washed four times with blocking buffer and incubated with 25 ml of TMB peroxidase substrate (Kirkegaard & Perry, Gaithersburg, Md.). The absorbance at 405 nm of each well was measured using a microplate reader (Molecular devices, Menlo Park, Calif.). The higher the O.D. reading, the greater the amount of specific antibody in the sample.

The data for each of two experiments are provided in Tables IV and V which follow on separate sheets. The results are summarized in Tables VI and VII collating the data from the two experiments is provided as well. On the summary page n stands for the number of animals in each of the four groups. S.D. stands for standard deviation and Avg. is the average O.D. reading for all the animals in a particular group.

The results of Group 4 demonstrate that the use of a gene therapy vector encoding an accessory molecule ligand (CD40L) enhances the immunization against β-gal encoded by a genetic or gene therapy vector. The average O.D. reading of the 1:40 dilution of the sera from animals of this group is significantly higher than that of groups 1, 2, and 3 ($P<0.05$, Bonferroni t tests, see Table VII).

Figure 16:
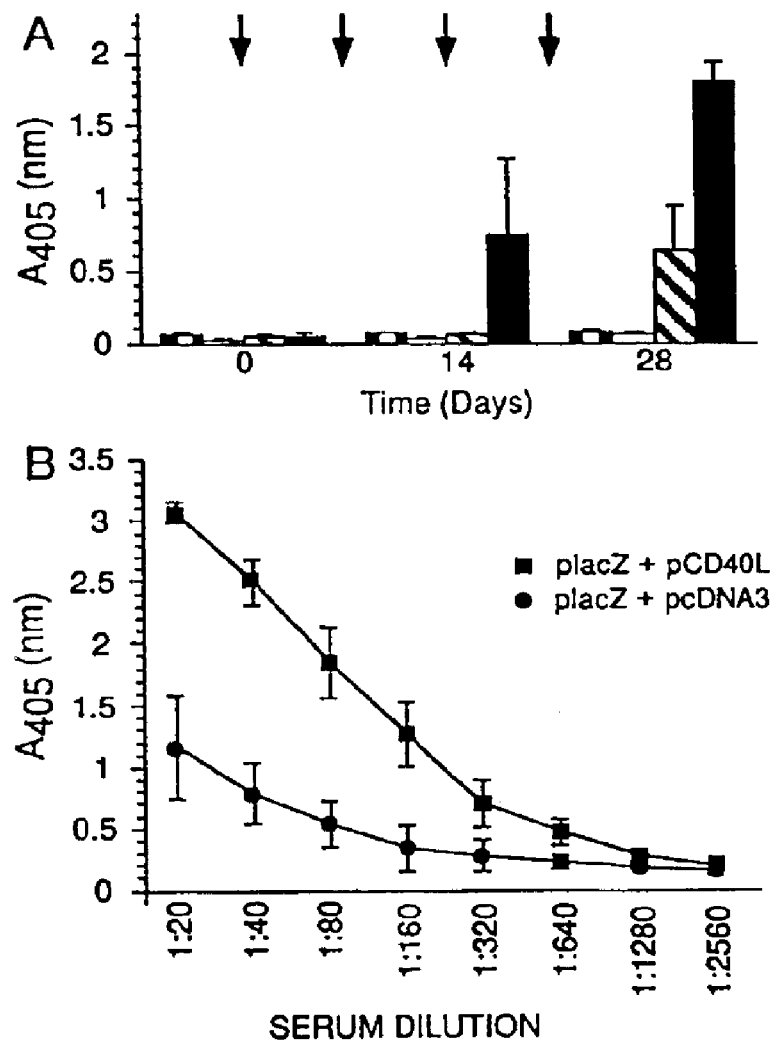
FIG. 16.
Figure 17:
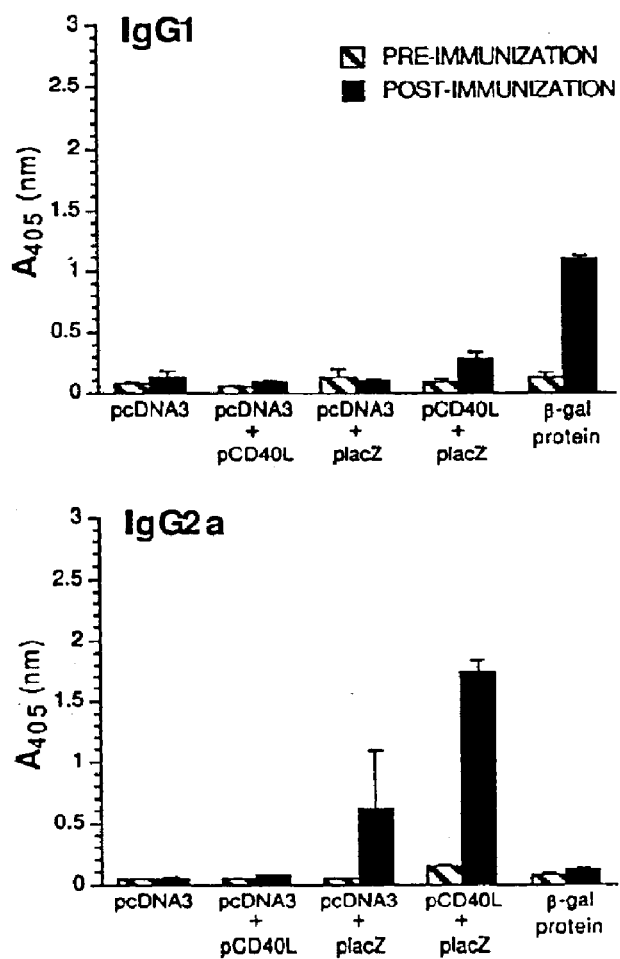
FIG. 17.
Figure 18:
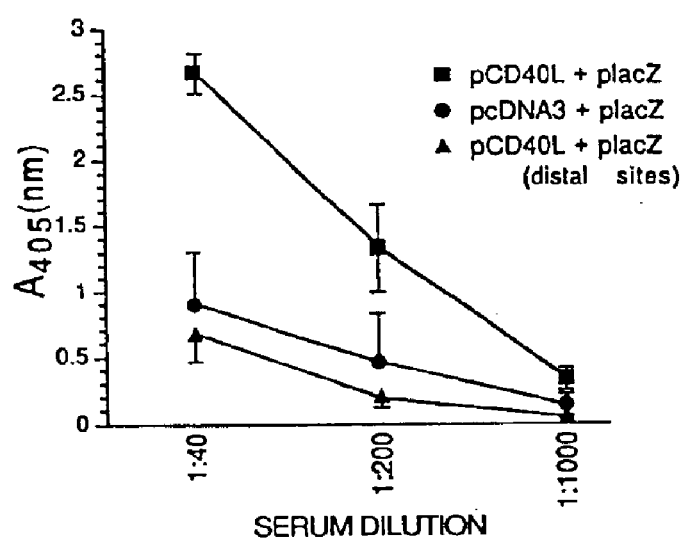
FIG. 18.
Figure 19:
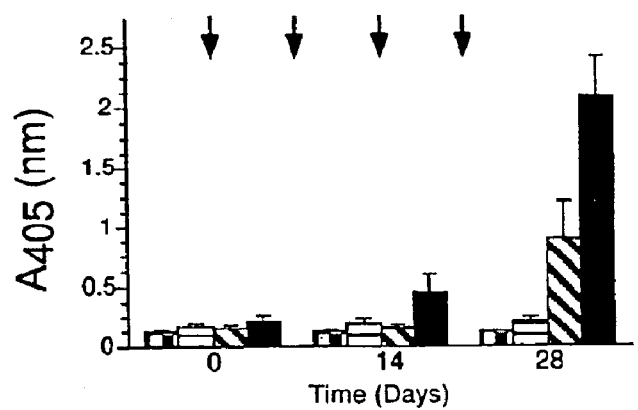
FIG. 19.
Figure 20:
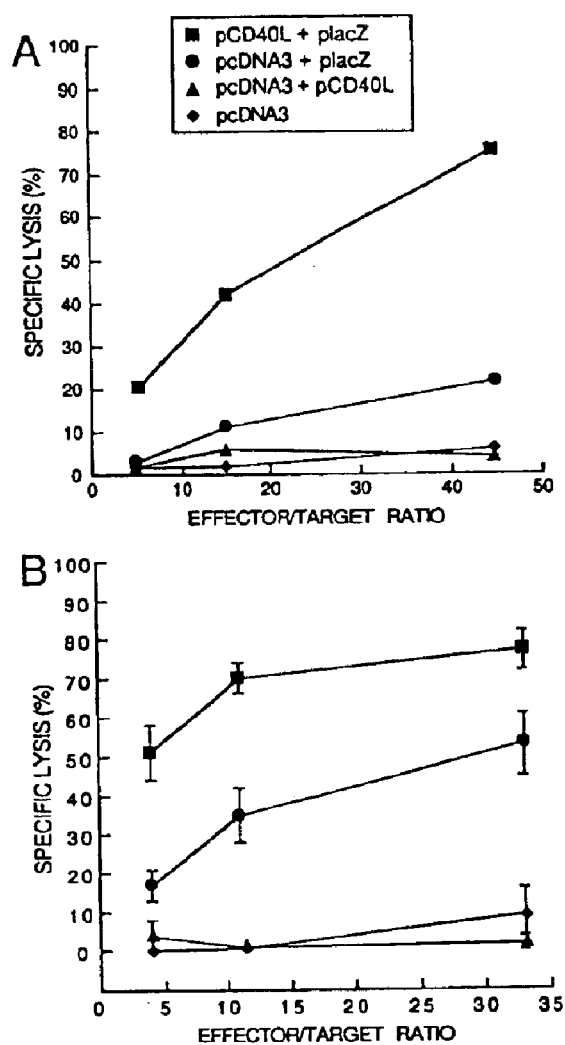
FIG. 20.

Data from an additional experiment further reinforce the finding that the gene therapy vector encoding an accessory molecule ligand enhances immunization against β-gal (FIG. 16). Here, pCD40L and placZ were co-injected into skeletal muscle, to test for enhancement of the immune response to placZ, a pcDNA3-based vector encoding *E. coli* β-galactosidase. The relative anti-β-gal Ab activities were determined via ELISA. As expected, mice injected with either the non-modified pcDNA3 vector or pCD40L alone did not produce detectable antibodies to β-gal (FIG. 16A). Mice were injected with either 100 μg pcDNA3 (checkered bar), 50 μg, pcDNA3+50 μg pCD40L (lined bar), 50 μg pcDNA3+50 μg placZ (striped bar), or 50 μg pCD40L+50 μg placZ (solid bar). On the other hand, mice that received placZ and pcDNA3 developed detectable anti-β-gal antibodies one week after the fourth and final injection, at d28. Mice that received placZ and pCD40L developed higher titers of anti-β-gal antibodies than mice injected with placZ and pcDNA3. FIG. 16B, ELISA analyses of serial dilutions of sera collected at d28, shows that mice co-injected with placZ and pCD40L had an eight-fold higher mean titer of anti-β-gal antibodies at d28 than mice treated with placZ+ pcDNA3.

i. Immunoglobulin Subclass Production Stimulated by Accessory Molecule Vector Co-Injection Despite enhancing the titer of the anti-β-gel antibody response, the subclass of anti-β-gel IgG induced by injection of placZ was not altered by the co-injection of pCD40L. $IgG_{2a}$ anti-β-gal antibodies predominated over $IgG_1$ subclass antibodies in the sera of mice injected with either placZ and pcDNA3 or placZ and pCD40L (FIG. 17). Also depicted are the ELISA O.D. measurements of anti-β-gal $IgG_1$ and anti-β-gal $IgG_{2a}$ present in the pre-immune sera (striped bar) or post-immune sera (solid bar), collected at d28) of each group of mice, injected as indicated on the abscissa. In contrast, BALB/c mice injected with β-gal protein developed predominantly $IgG_1$ anti-β-gal antibodies, and no detectable $IgG_{2a}$ anti-β-gal antibodies.

ii. Augmentation of Vaccination by Accessory Molecule Vector Requires Co-Injection with placZ at the Same Site The adjuvant effect of the pCD40L plasmid on the anti-β-gal antibody response was noted only when it was injected into the same site as placZ (FIG. 18). Groups of BALB/c mice (n=4) received intramuscular injections of placZ and pCD40L together at the same site, or as simultaneous separate injections at distal sites (right and left hind leg quadriceps). A control group received intramuscular injections of placZ and pcDNA3 at the same site. Animals were bled at d28 and the sera tested for anti-β-gal Ab at different dilutions, as indicated on the abscissa. The graph illustrates a representative experiment depicting the mean O.D. at 405 nm of replicate wells of each of the serum samples for each group, at a 1:40, 1:200, or 1:1000 dilution. Animals injected simultaneously with placZ and pCD40L, but at different sites, did not develop detectable anti-β-gel antibodies until d28. Moreover, the anti-β-gel antibody titers of the sera from such animals at d28 were similar to that of mice that received placZ and pcDNA3, and significantly less than that of animals that received placZ and pCD40L together at the same site.

iii. Augmentation of Vaccination When Accessory Molecule Vector and placZ are Co-Injected into Dermis The pCD40L plasmid also enhanced the anti-β-gal antibody response to placZ when injected into the dermis. In the experiment shown in FIG. 19, mice received intradermal injections, near the base of the tail, with either 50 μg pcDNA3 (checkered bar), 25 μg pcDNA3+25 μg pCD40L (lined bar), 25 μg pcDNA3+25 μg placZ (striped bar), or 25 μg pCD40L+25 μg placZ (solid bar). Injections bleeds and ELISA analyses were performed as in FIG. 16A. The checkered bar and lined bar groups each consisted of 8 mice while the striped bar and solid bar groups each consisted of 12 mice. The height of each bar represents the mean O.D. of sera at a 1:40 dilution of each group ±S.E. A statistical analysis of the data indicated that the striped bar and solid bar groups are independent ($P<0.05$). As observed with intramuscular injection, mice co-injected with placZ and pCD40L developed detectable serum anti-β-gal antibodies one week following the second injection (d14), and two weeks earlier than mice injected with placZ and pcDNA3. Moreover, these animals also had an eight-fold higher mean titer of anti-β-gal antibodies than mice of the placZ-injected group at d28. Mice injected with either the non-modified pcDNA3 vector or pCD40L alone did not produce detectable antibodies to β-gal.

b. Augmentation of the CTL Response in Mice Co-Injected with an Accessory Molecule Gene Therapy Vector and placZ The ability of pCD40L to enhance induction, by placZ, of CTL specific for syngeneic β-gal-expressing target cells was tested. BALB/c mice co-injected with pCD40L and placZ into skeletal muscle (FIG. 20A) or dermis (FIG. 20B) generated greater numbers of CTL specific for P13.2, a placZ transfected P815 cell line, than mice co-injected with placZ and pcDNA3. At a 5:1 effortor:target ratio, the splenocyte effector cells from mice that received intramuscular injections of placZ and pCD40L achieved greater than 20% specific lysis of P13.2. In contrast, when splenocyes of mice that received the control injection with placZ and pcDNA3 were used, a 9-fold greater ratio of effector to target cells was required to achieve this level of specific lysis. Similarly, the splenocyte effector cells from mice that received intradermal injections of placZ and pCD40L killed more than 50% of the P13.2 cells at effector:target ratios of 4:1. To achieve comparable levels of specific lysis required eight-fold higher effector:target ratios using splenocytes from mice that received intradermal injections of placZ and pcDNA3. Nevertheless, the splenocytes of mice co-injected with pCD40L and placZ did not have greater non-specific CTL activity for P815 cells than that of mice that received placZ along with pcDNA3 (FIG. 20). As expected, the splenocytes from mice that received injections of pcDNA3 alone, or pcDNA3 and pCD40L, did not mediate specific lysis of P13.2 or P815 cells.

TABLE IV

Experiment #1
Injections of plasmid DNA i.m.: Apr. 3, 1996; Apr. 10, 1996; Apr. 17, 1996; Apr. 24, 1996
ELISA for anti-beta galactosidase antibodies:

| Group | Animal | Dilution of Pre-Bleed (4/3) | | | Dilution of Bleed (4/17) | | |
|---|---|---|---|---|---|---|---|
| | | 1/140 | 1/200 | 1/1000 | 1/140 | 1/200 | 1/1 |
| pcDNA3 (p-control, 100 mcg) (Control vector) | 1 | 0.09 | 0.11 | 0.09 | 0.06 | 0.06 | |
| | 2 | 0.11 | 0.09 | 0.09 | 0.07 | 0.07 | |
| | 3 | 0.12 | 0.11 | 0.10 | 0.09 | 0.09 | |
| | 4 | 0.11 | 0.10 | 0.10 | 0.08 | 0.11 | |
| | Avg. | 0.11 | 0.11 | 0.11 | 0.11 | 0.11 | |
| | S.D. | 0.01 | 0.01 | 0.01 | 0.01 | 0.02 | |
| p-lacZ (50 mcg) + p-Control (50 mcg) | 5 | 0.13 | 0.10 | 0.10 | 0.07 | 0.11 | |
| | 6 | 0.10 | 0.11 | 0.10 | 0.07 | 0.06 | |
| | 7 | 0.19 | 0.10 | 0.18 | 0.07 | 0.07 | |
| | 8 | 0.10 | 0.09 | 0.10 | 0.08 | 0.07 | |
| | Avg. | 0.13 | 0.10 | 0.12 | 0.07 | 0.08 | |
| | S.D. | 0.04 | 0.01 | 0.04 | 0.01 | 0.02 | |
| p-lacZ (50 mcg) + pRcCMV-mCD40L (p-mCD40L, 50 mcg) | 27 | 0.06 | 0.06 | 0.06 | 0.13 | 0.11 | |
| | 18 | 0.06 | 0.06 | 0.06 | 0.27 | 0.13 | |
| | 19 | 0.06 | 0.06 | 0.06 | 0.23 | 0.19 | |
| | 20 | 0.06 | 0.06 | 0.06 | 0.23 | 0.19 | |
| | Avg. | 0.06 | 0.06 | 0.06 | 0.74 | 0.47 | |
| | S.D. | 0.00 | 0.00 | 0.00 | 1.06 | 0.66 | |

TABLE V

Experiment #2
Injections of plasmid DNA i.m.: Jun. 5, 1996; Jun. 12, 1996; Jun. 19, 1996; Jun. 26, 1996
Dilutions of sera for anti-beta galactosidase antibodies:

| Group | Animal | Dilution of Pre-Bleed (6/5) | | | Dilution of Bleed (7/1) | | |
|---|---|---|---|---|---|---|---|
| | | 1/140 | 1/200 | 1/1000 | 1/140 | 1/200 | 1/1 |
| p-Control (50 mcg) + p-mCD40L (50 mcg) | 9 | 0.02 | 0.02 | 0.06 | 0.04 | 0.01 | |
| | 10 | 0.06 | 0.02 | 0.10 | 0.02 | 0.02 | |
| | 11 | 0.02 | 0.02 | 0.07 | 0.03 | 0.01 | |
| | 12 | 0.06 | 0.03 | 0.05 | 0.18 | 0.04 | |
| | Avg. | 0.04 | 0.04 | 0.04 | 0.04 | 0.04 | |
| | S.D. | 0.02 | 0.01 | 0.02 | 0.07 | 0.01 | |
| p-lacZ (50 mcg) + p-Control (50 mcg) | 5 | 0.02 | 0.03 | 0.02 | 0.06 | 0.04 | |
| | 6 | 0.03 | 0.02 | 0.03 | 0.14 | 0.03 | |
| | 7 | 0.56 | 0.13 | 0.06 | 0.29 | 0.06 | |
| | 8 | 0.01 | 0.02 | 0.05 | 0.06 | 0.02 | |
| | Avg. | 0.15 | 0.05 | 0.04 | 0.13 | 0.04 | |
| | S.D. | 0.27 | 0.05 | 0.02 | 0.11 | 0.02 | |
| p-lacZ (50 mcg) + p-mCD40L (50 mcg) | 13 | 0.23 | 0.06 | 0.05 | 0.28 | 0.07 | |
| | 14 | 0.02 | 0.02 | 0.03 | 0.04 | 0.02 | |
| | 15 | 0.02 | 0.02 | 0.02 | 0.89 | 0.21 | |
| | 16 | 0.05 | 0.04 | 0.02 | 0.11 | 0.04 | |
| | Avg. | 0.08 | 0.04 | 0.03 | 0.33 | 0.08 | |
| | S.D. | 0.10 | 0.02 | 0.02 | 0.39 | 0.09 | |

TABLE VI

Summary

| | | Pre-Immune @ beta-gal | | | Early @ beta-ga | | |
|---|---|---|---|---|---|---|---|
| | | 1/140 | 1/200 | 1/1000 | 1/140 | 1/200 | 1/1 |
| 1) p-Control (n = 4) | Avg. | 0.11 | 0.11 | 0.11 | 0.11 | 0.11 | |
| | S.D. | 0.01 | 0.01 | 0.01 | 0.01 | 0.02 | |
| 2) p-mCD40L + p-Control (n = 4) | Avg. | 0.04 | 0.04 | 0.04 | 0.04 | 0.04 | |
| | S.D. | 0.02 | 0.01 | 0.02 | 0.07 | 0.01 | |
| 3) p-lacZ + p-Control (n = 8) | Avg. | 0.11 | 0.04 | 0.04 | 0.11 | 0.03 | |
| | S.D. | 0.22 | 0.04 | 0.01 | 0.09 | 0.02 | |
| 4) p-lacZ + p-mCD40L (n = 8) | Avg. | 0.11 | 0.04 | 0.03 | 0.25 | 0.06 | |
| | S.D. | 0.10 | 0.02 | 0.01 | 0.32 | 0.07 | |
| Anti-beta-galactosidase standard: O.D. | | 67 ng | 22 ng | 7.4 ng | 2.5 ng | .82 ng | .27 ng |
| | | 3.01 | 2.98 | 2.05 | 1.10 | 0.52 | 0.26 |
| | | 3.14 | 3.14 | 2.25 | 1.20 | 0.56 | 0.26 |

TABLE VII

BONFERRONI t-TESTS

| Comparison | Difference of means | t | P < .05 |
|---|---|---|---|
| 4 vs 2: | 2.06 − 0.04 = 2.02 | 3.782 | Yes |
| 4 vs 1: | 2.06 − 0.11 = 1.95 | 3.651 | Yes |
| 4 vs 3: | 2.06 − 0.61 = 1.45 | 3.325 | Yes |
| 3 vs 2: | 0.61 − 0.04 = 0.57 | 1.067 | No |
| 3 vs 1: | 0.61 − 0.11 = 0.50 | Do not test | |
| 1 vs 2: | 0.11 − 0.04 = 0.07 | Do not test | |

Degrees of freedom: 20

ONE WAY ANALYSIS OF VARIANCE

| Group | N | Mean | Std Dev | SEM |
|---|---|---|---|---|
| 1 | 4 | 0.11 | 0.01 | 0.00 |
| 2 | 4 | 0.04 | 0.04 | 0.02 |
| 3 | 8 | 0.61 | 1.11 | 0.39 |
| 4 | 8 | 2.06 | 0.97 | 0.34 |
| 5 | 4 | 1.51 | 0.77 | 0.38 |
| 6 | 4 | 1.14 | 0.53 | 0.26 |
| 7 | 4 | 0.83 | 0.43 | 0.22 |

ONE WAY ANALYSIS OF VARIANCE

| Source of Variation | SS | DF | Variance Est (MS) |
|---|---|---|---|
| Between Groups | 18.29 | 6 | 3.05 |
| Within Groups | 18.39 | 29 | 0.63 |
| Total | 36.69 | 35 | |

$$F = \frac{s2\_bet}{s2\_wit} = \frac{MSbet}{Mswit} = \frac{3.05}{0.63} = 4.81 \; P = 0.002$$

4. Treatment of Neoplasia Using a Gene Therapy Vector Containing an Accessory Molecule Gene or Chimeric Accessory Molecule Gene a. Treatment of Neoplasia in Mice The treatment of a neoplasia in a mouse model system has been demonstrated using the genes encoding accessory molecule ligands of the present invention. Gene therapy vectors containing an accessory molecule ligand gene (murine CD40 ligand) were prepared as has been previously described in the above examples. These gene therapy vectors were used to introduce that accessory molecule ligand gene into neoplastic cells, Line1 cells, from a tumor which originated in BALB/c mice. The accessory molecules were introduced into the neoplastic cells according to the above examples. The expression of the accessory molecule ligand on the surface of these neoplastic cells was confirmed using flow cytometry as has been described in the above examples.

The effectiveness of the accessory molecule ligand genes for treating neoplasia was shown as follows. Female BALB/c mice (6–8 weeks old) were injected i.p. with $1.0 \times 10^5$ irradiated Line1 neoplastic cells. The neoplastic Line1 cells are derived from a spontaneous lung adenocarcinoma in a BALB/c mouse. This neoplastic cell has been described by Blieden et al., *Int. J. Cancer Supp.*, 6:82 (1991). Other female BALB/c mice were injected i.p. with $1.0 \times 10^5$ irradiated Line1 tumor cells that had previously been transduced with the gene therapy vector encoding the accessory molecule ligand gene (murine CD40) as described above.

Figure 7:
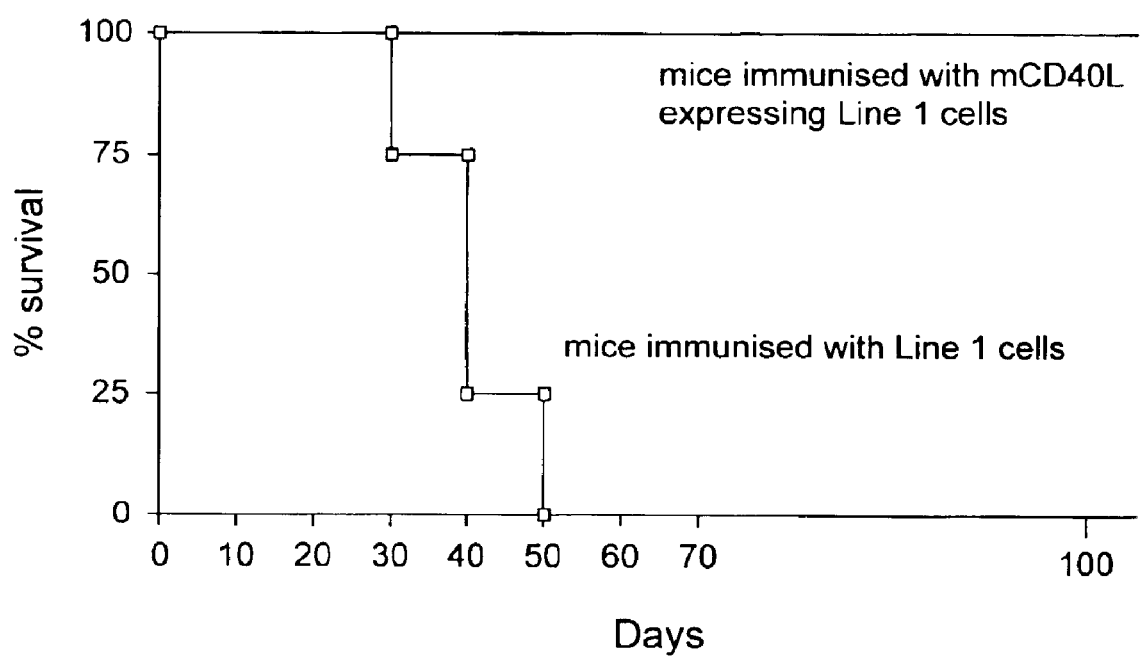
FIG. 7.

Each group of mice was allowed to generate an immune response for 10 days. After 10 days each mouse was challenged with $1.0 \times 10^4$ live, non-irradiated Line1 neoplastic cells. These mice were then monitored for the formation of tumors and then sacrificed when the tumors grew to 2.0 cm because of morbidity. The results of this monitoring are shown in FIG. 7. As can be seen by FIG. 7, the mice immunized with the neoplastic cell expressing the accessory molecule ligands of the present invention on the cell surface remained free of tumor throughout the experiment. Mice immunized with the neoplastic cells not having the accessory molecule ligand genes of the present invention succumbed to tumor 50 days after challenge with the neoplastic cells.

Figure 21:
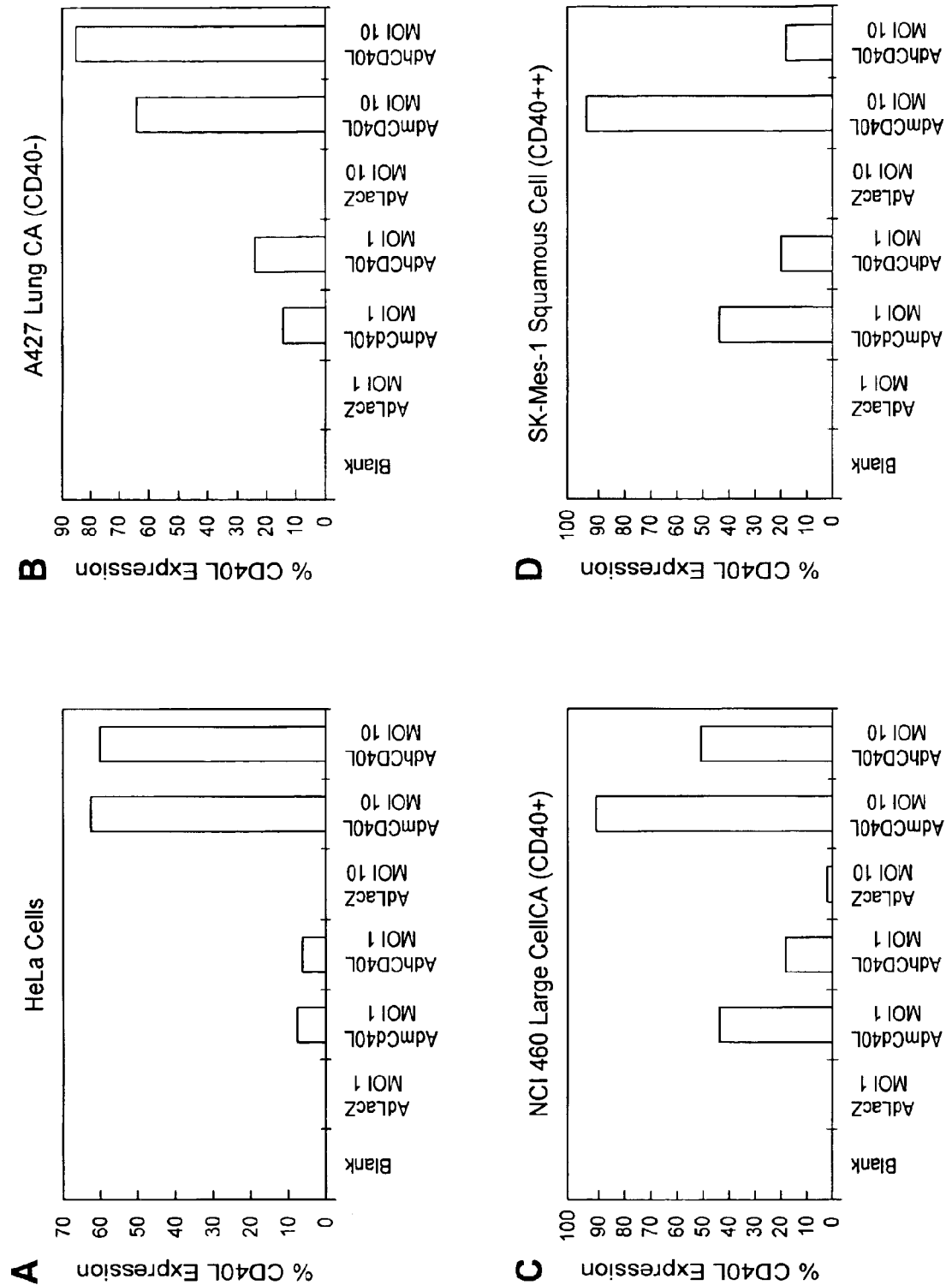
FIG. 21.

FIG. 21 demonstrates downmodulation of human CD40L, but not murine CD40L, in lung tumor cell lines that express CD40. Human cell lines HeLa (CD40-negative cervical carcinoma, FIG. 21A), A427 (CD40-negative lung carcinoma, FIG. 21B), NCI 460 (weakly CD40-positive lung large cell carcinoma, FIG. 21C), and SK-Mes-1 (strongly CD40-positive lung squamous cell tumor, FIG. 21D) were infected with adenovirus encoding lac-Z (Ad-LacZ), murine CD40L (Ad-mCD40L), and human CD40L (Ad-hCD40L) at an MOI of 0 (Blank), 1, and 10. 48 hours after infection, murine CD40L and human CD40L surface expression was determined. The percentage of cells that express ligand are plotted on the Y-axis. Human and mouse CD40L are expressed at equal levels in CD40-negative cell lines. However, only murine CD40L expression is stable on cell lines that express CD40. In contrast to mCD40L, human CD40L is downmodulated on CD40-positive tumors.

Figure 22A:
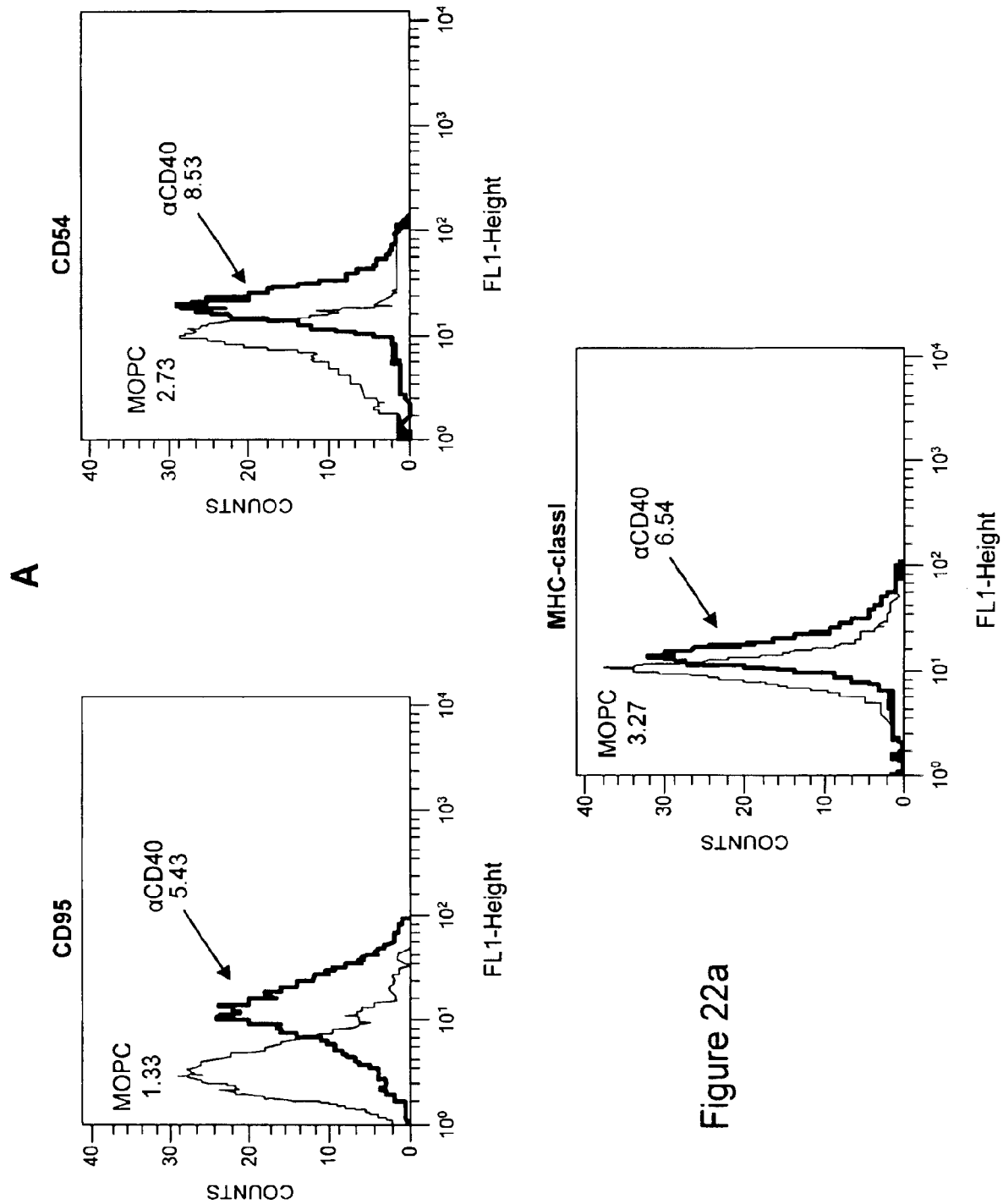
FIG. 22A shows that CD40 binding induces enhanced expression of the tumor cell surface markers CD95 (Fas), CD54 (ICAM-1), and MHC-I, in lung tumor cell lines.

The data graphed in FIG. 22A show that CD40 binding induces expression of tumor surface markers. Treating CD40-expressing lung cancer cell lines with αCD40 mAb resulted in enhanced expression of the tumor cell surface markers CD95 (Fas), CD54 (ICAM-1) and class I major histocompatibility antigens (MHC I). NCI 460, a weakly CD40-positive lung large cell carcinoma, was incubated with a CD40-specific monoclonal antibody (thick line), or MOPC21, an isotype control mAb (thin line), on CD32-expressing mouse fibroblasts for 48 hours. Following the 48 hr incubation, the lung tumor cells were analyzed for CD95, CD54, and MHC-I expression by FACS.

Figure 22B:
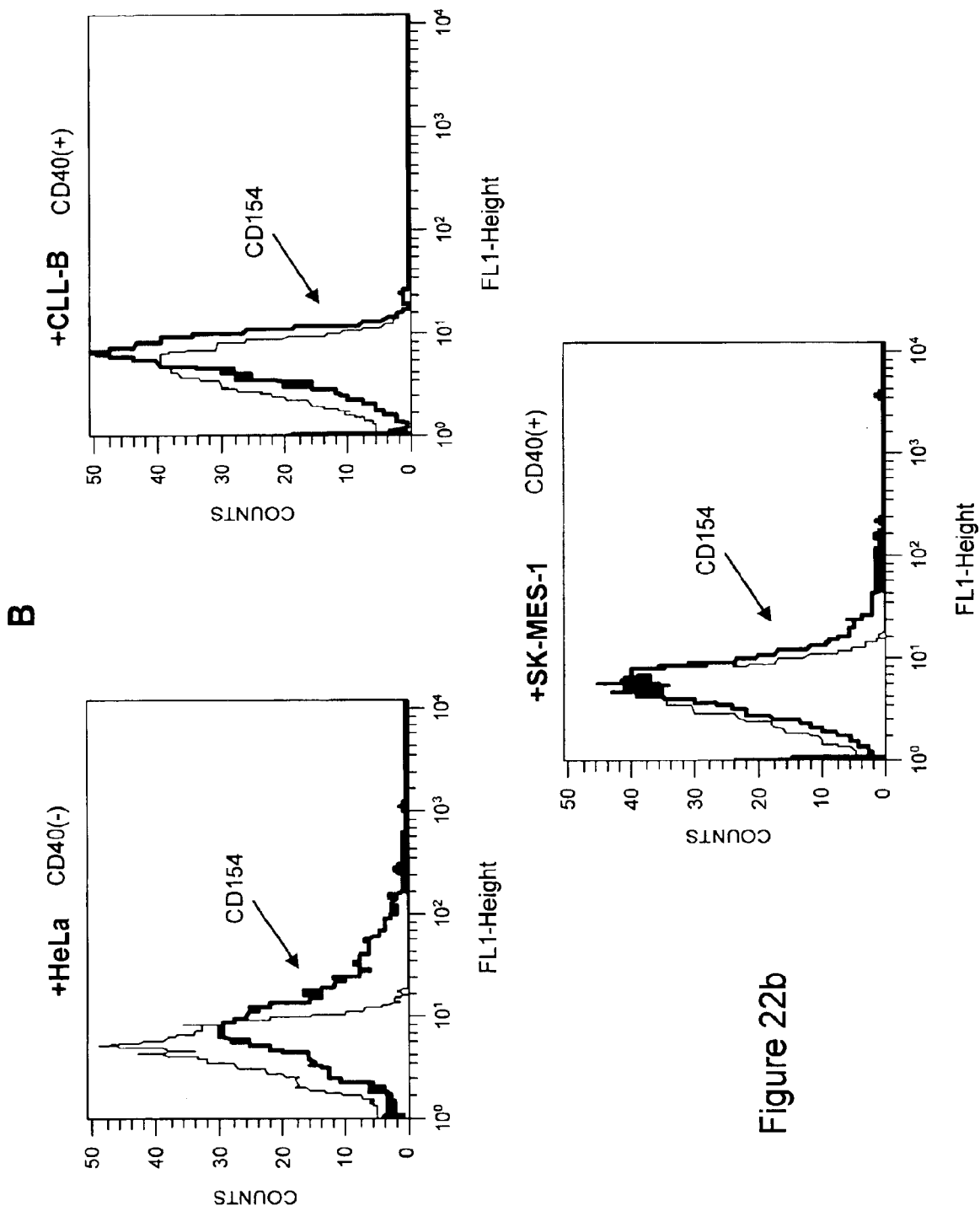
FIG. 22B shows downmodulation of human CD40L by CD40-positive tumor cells.

FIG. 22B again shows downmodulation of human CD40L by CD40-positive tumor cells. HeLa (CD40-negative), CLL (CD40-positive), and SK-MES-1 (CD40-positive) tumor cells were cocultured for 24 hours with CD3-activated normal donor T cells at a tumor cell:T cell ration of 2.5:1. following coculture, CD2-expressing T cells were analyzed for CD40L surface expression by FACS. Thin lines represent T cells stained with FITC-labeled isotype control antibody (MOPC21) and thick lines represent activated T cells stained with FITC-labeled αCD40L antibody (αCD154 antibody). The CD40-positive tumor cell lines, SK-MES-1, and CLL, do not express CD40 ligand on their surfaces.

5. Expression of the Human and Mouse Accessory Molecule Ligand, Fas Ligand, in Human Blood Lymphocytes a. Construction of a Genetic Construct and Gene Therapy Vector Containing the Human and Mouse Fas Ligand Gene Either the human accessory molecule ligand gene (human Fas ligand) or the murine accessory molecule ligand gene (murine Fas ligand) was constructed utilizing the respective human and murine genes. An altered accessory cell molecule, in which a putative MMP-cleavage site was removed, was made and designated ΔFasL-pcDNA3. The nucleotide sequence of ΔFasL-pcDNA3 is listed as SEQ ID NO: 40. Human Fas ligand nucleotides 325 to 342, encoding six amino acids, are missing from ΔFasL. The design of ΔFasL was based on reasoning that Domain III contains sites most accessible to MMPs, and could thus be the target on the molecule for cleavage from the surface of the cell. Sequences of the human Fas ligand gene have been determined and are listed as SEQ ID NOS: 13 and 30 (Genbank accession U11821). Sequences of mouse Fas ligand genes have been determined and are listed as SEQ ID NOS: 14 (C57BL/6, Genbank accession U10984) and 31 (Balb/c, Genbank accession U58995). The sequence of the rat Fas ligand gene has been determined and is listed as SEQ ID NO: 25 (Genbank accession U03470). Chimeric constructs are made, as described in Example 2 for CD40 ligand chimeric constructs, in which Domain III of human Fas ligand is replaced with Domains of other proteins, particularly proteins of the TNF family. Chimeric constructs include, but are not limited to, human Fas ligand with Domain III replaced by Domain III of murine Fas ligand (chimeric sequence listed as SEQ ID NO: 37, sequence line-up shown in FIG. 37), or replaced by Domain III of human CD70 (chimeric sequence listed as SEQ ID NO: 38, sequence line-up shown in FIG. 38), or replaced with Domain I of human CD70 (chimeric sequence listed as SEQ ID NO: 39, sequence line-up shown in FIG. 39). Chimeric constructs in which multiple domains, for example, two copies of human CD70 Domain III, are inserted into human Fas ligand in place of Domain III, are also made using methods described in Example I. Chimeric constructs in which synthetic sequences are used to replace Domain III of human Fas ligand are also made.

i. Human Fas Ligand Cloning

The cDNA encoding human Fas-ligand was subcloned in the eukaryotic expression vector pcDNA3. Normal donor blood lymphocytes were activated for 4 hours with 1 ng/ml PMA plus 0.5 uM ionomycin. Total RNA was isolated with the Olagen RNAEASY kit. cDNA was then synthesized from poly-A RNA with oligo-dT primers using the Gibco-BRL Superscript cDNA synthesis kit. The gene encoding human Fas-ligand was then PCR amplified with the Fas-ligand-specific primers (sense primer, SEQ ID NO: 32, antisense primer, SEQ ID NO: 33). The Fas-ligand PCR product was then subcloned into pcDNA3 using standard molecular biology techniques. RT-PCR products, subcloned into pcDNA3, are designated hFasL-pcDNA3.

ii. Murine Fas Ligand Cloning

The murine Fas-ligand geneS from Balb/c and C57/BL6 strains of mice were also amplified following activation of mouse splenocytes with PMA plus ionomycin as described above, and amplified from poly-A synthesized cDNA as described above (sense primer, SEQ ID NO: 35, antisense primer, SEQ ID NO: 35). These genes were subcloned in the pTARGET expression vector (Promega, Madison, Wis.).

RT-PCR products, subcloned into pcDNA3, are designated mFasL-pcDNA3.

iii. Adenovirus Vector Construction

For construction of adenovirus vectors encoding human Fas-ligand, murine Fas-ligand or ΔFas-ligand, the cloned cDNA insert is subcloned into the plasmid pRc/RSV (Invitrogen, San Diego, Calif.) at the HindIII-XbaI site. A BglII-XhoI fragment with the RSV promoter-enhancer and the bovine growth hormone poly-A signal sequence was subcloned into the BamHI-XhoI site of plasmid MCS(SK) pXCX2. The plasmid MCS(SK)pXCX2 is a modification of the plasmid pXCX2, in which the pBluescript polylinker sequence was cloned into the E1 region. The resulting plasmid then is co-transfected along with pJM17 into 293 cells using the calcium phosphate method. Isolated plaques of adenovirus vectors are picked and expanded by infecting 293 cells. High titer adenovirus preparations are obtained, as described above which uses a cesium chloride gradient for concentrating virus particles via a step gradient, with the densities of 1.45 g/cm$^3$ and 1.20 g/cm$^3$, in which samples are centrifuged for 2 hours in an SW41 rotor (Beckman, Brea, Calif.) at 25,000 rpm at 4° C. The virus band is desalted using a Sephadex G-25 DNA grade column (Pharmacia, Piscataway, N.J.), and the isolated virus is stored at −70° C. in phosphate-buffered saline with 10% glycerol. The titer of the virus is determined by infecting permissive 293 cells at various dilutions and counting the number of plaques. Titers typically range from $10^{10}$ to $10^{12}$ plaque forming units/ml. The adenovirus constructs are designated Ad-hFasL, Ad-mFasL and Ad-ΔFasL.

b. Introduction of the Murine and Human Fas Ligand Genes into Human Cells

The constructs hFasL-pcDNA3, mFasL-pcDNA3 and ΔFasL-pcDNA3 are transfected into 293 via electroporation. The transfected cells are selected in medium containing G418. Fas-ligand transfectants are screened for expression of the transgene using anti-Fas-ligand antibody and flow cytometry. The methods used are similar to those described for transfection of CD40L into CLL cells.

For FasL-adenovirus infection, $10^6$ freshly thawed and washed CLL cells or HeLa cells are suspended in 0.5 to 1 mL of culture medium for culture at 37° C. in a 5% $CO_2$-in-air incubator. Adenovirus are added to the cells at varying multiplicity of infection (MOI), and the infected cells are cultured for 48 hours, unless otherwise stated, before being analyzed for transgene expression.

c. Expression of the Fas Ligand Genes in Human Cells

Mice with the lymphoproliferative or generalized lymphoproliferative disorder are unable to delete activated self-reactive cells outside of the thymus. This is related to the fact that, in these mice, interactions between the Fas receptor and an accessory molecule ligand, Fas ligand, are defective. These animals develop numerous disorders including lymphadenopathy, splenomegaly, nephritis, and systemic autoimmune pathology which resembles that seen in patients with systemic lupus erythematosus or rheumatoid arthritis (RA). It is conceivable that the normal interactions between the Fas receptor and the accessory molecule ligand that are responsible for clearance of activated lymphocytes from joints may be impaired in RA patients.

RA synovial lymphocytes express the Fas receptor at a higher proportion than that of matched RA blood lymphocytes to matched normal donor blood lymphocytes. On the other hand, RA synovial lymphocytes express little or no accessory molecule ligand. Since the RA synovial lymphocytes are sensitive to Fas-induced apoptosis, it is feasible that local expression of Fas ligand in the RA joint could serve to eliminate the synovial mononuclear cells that potentially mediate RA autoimmune pathology.

Figure 23:
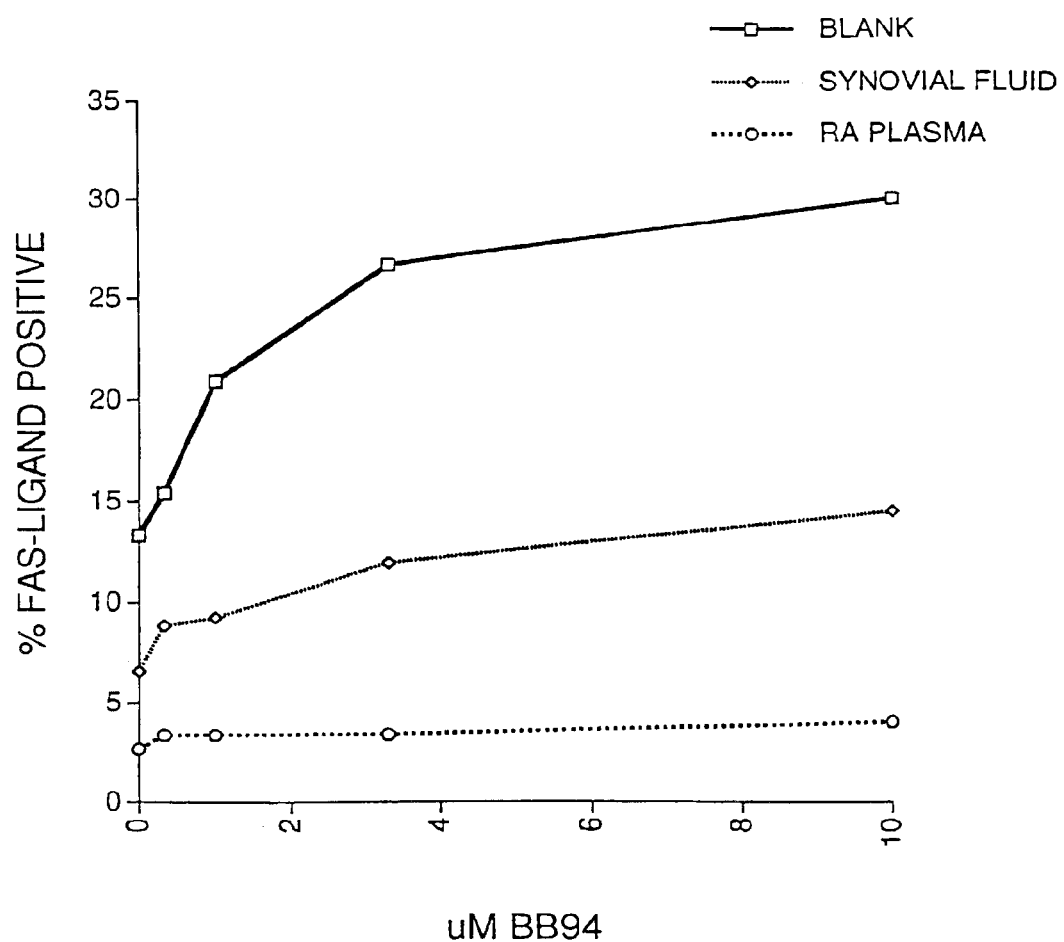
FIG. 23.

FIG. 23 shows that Fas-ligand expression in lymphocytes is inhibited by exposure to RA synovial fluid. Normal donor blood T cells were activated for 5 hours with 1 ng/ml PMA plus 0.5 μM ionomycin. Cells were incubated in the presence of rheumatoid arthritis blood plasma (circles), RA synovial fluid (diamonds), or neither (squares). In addition, cells were incubated with increasing concentrations of the MMP inhibitor BB94. Following activation, cells were analyzed for Fas-ligand surface expression by FACS. The percentage of cells expressing Fas ligand are plotted in FIG. 23. This experiment demonstrates that there is a factor(s) present in RA synovial fluid and serum that prevents surface expression of Fas-ligand.

d. Function of Human, Murine and Chimeric Accessory Molecule Ligand, Fas Ligand

To determine the capacity of the ΔFasL constructs, the above-mentioned transfected cells are mixed with the Fas-ligand sensitive human T cell line, JURKAT. Following 4 hours coculture, the nonadherant JURKAT cells are collected and evaluated for apoptosis. The fluorescent compound 3,3' dihexyloxacarbocyanine iodide ($DiOC_6$) is used to evaluate for apoptosis using a modification of a previously described protocol. For this, the cells are washed once at room temperature in phosphate buffered saline (PBS, pH 7.2). Cells are placed into separate wells of a 96 well U-bottom plastic microtiter plate at $10^5$–$5\times10^5$ cells/well in 50 ml total volume. If indicated, saturating amounts of PE-conjugated antibodies are added followed by addition of $DiOC_6$ and propidium iodide (PI). $DiOC_6$ and PI are used at 40 nM and 10 ng/ml final concentrations, respectively. The cells are then incubated 15 minutes in a 37° C. 5% $CO_2$ tissue culture incubator. The stained cells are then washed twice in ice cold PBS and ultimately suspended in 200 ml SM and analyzed by FACS. Dead cells and debris with characteristic forward and light scatter profiles and PI staining are excluded from analysis.

The ability of cells expressing ΔFasL-pcDNA3 to direct Fas-mediated apoptosis of cells expressing CD95 is compared with that of cells expressing FasL-pcDNA3. Relative stability of the protein products encoded by ΔFasL-pcDNA3 or FasL-pcDNA3 pre- and post- culture with RA synovial fluid, and with or without the metalloproteinase inhibitors, are assessed via flow cytometry of cells expressing either ligand.

6. Treatment of Arthritis with Gene Therapy Vectors Encoding an Accessory Molecule Ligand, Fas Ligand The heterologous Fas-ligand constructs, made as described above, that show the highest stability of expression in combination with the greatest ability to mediate Fas-induced apoptosis, are used in gene therapy for RA. Potential therapeutic constructs are tested in well-characterized mouse models of arthritis to assess efficiency and function in vivo.

a. Gene Therapy Treatment of Arthritis in Mice i. Mouse Models for Arthritis

One mouse arthritis model is collagen-induced arthritis. It is known that injecting DBA/1 mice with type II collagen in complete Freund's adjuvant (CFA) induces an arthritis with synovitis and erosions that histologically resemble RA. For our studies, male DBA/1 mice are immunized with bovine type II collagen in complete Freund's adjuvant on day 0 and boosted itraperitoneally (i.p.) on day 21. On day 28, animals are given an additional i.p. injection with lipopolysaccharide (LPS) and/or the same type collagen, or an injection of acetic acid alone. Swelling and/or redness of a fore or hind paw in animals immunized with collagen typically is detected the third or fourth week following the second injection. The vertebra are only rarely affected, and then only weeks after the initial peripheral joint swelling. Affected joints display initial histologic changes of synovial edema, followed by synovial hyperplasia.

Another animal model, recently described by Kouskoff, V. et al., in Cell 87:811–822 (1997) was generated fortuitously, by crossing a T cell receptor (TCR) transgenic mouse line with the non-obese-diabetic (NOD) strain to produce the KRNxNOD mouse model of RA. The offspring of such a mating universally develop a joint disease that is highly similar to that of patients with RA. Moreover, the disease in these animals has an early and reproducible time of onset and a highly reproducible course. The arthritis apparently is induced by chance recognition of an NOD-derived major histocompatibility complex (MHC) class II molecule by the transgenic TCR, leading to breakdown in the general mechanisms of self-tolerance and systemic self-reactivity.

ii. Relief of Arthritis Symptoms in Mice Treated with a Gene Therapy Vector Encoding an Accessory Molecule Ligand We have adapted and modified a protocol originally described by Sawchuk and colleagues for micro-injecting adenovirus vectors into mouse joints. Using this procedure we can reproducibly inject a 5 µl volume into the articular space of the mouse knee. In this procedure, the mice are anesthetized with metofane. A small incision of approximately 2–3 mm is made with a #11 scalpel blade in the skin over the lateral aspect of the knee to visualize the patellotibial ligament. We can inject up to 5 µl of fluid using a micro-100 µl-Hamilton syringe and a 30-gauge needle. After the injection, the knee incision is closed with NEXABOND (Veterinary Products Laboratory). Our adenovirus titers typically exceed $10^{10}$ plaque forming units (pfu) per ml, making it possible to deliver at least $5 \times 10^8$ pfu of virus in 5 ml into the knee joints, as outlined above. Control animals are injected with control Ad-lacZ vector, a replication-defective adenovirus vector lacking a transgene, or with the buffer used to suspend the virus (10 mM Tris, 1 mM $MgCl_2$, 10% glycerol).

In another method, splenocytes will be harvested from mice that are syngeneic to the host animal intended for adoptive transfer of transduced cells. Cell proliferation will be induced with exogenous IL-12 (100 units/ml) for 48 h. Cells are counted and then re-plated at densities of $5 \times 10^5$ or $1 \times 10^6$ cells per ml in a 12-well dish with 1 ml complete culture medium per well. Virus and ConA are added together at the time of replating in the presence of polybrene (8 µg/ml). The medium is changed 24 hours after infection with complete medium containing 100 units of recombinant IL-2 per ml. Aliquots of the transducer cells are examined, for Fas-ligand expression, at 48 hours after infection via flow cytometry.

Animals will receive standardized numbers of cytokine-producing cells or control mock-transfected cells intraperitoneally. Concentrated cell suspensions are injected directly into the mouse synovium, as described in section 4A above. In parallel, aliquots of the transferred cell populations are maintained in tissue culture supplemented with exogenous IL-2.

Mice are monitored in a blinded fashion for signs of arthritis. The date of disease onset is recorded and clinical severity of each joint or group or joints (toes, tarsus, ankle, wrist, knee) are graded as follows: 0 (normal), 1 (erythema), 2 (swelling), 3 (deformity), 4 (necrosis). The scores are summed to yield the arthritic score. The severity of arthritis is expressed both as the mean score observed on a given day, and as the mean of the maximal arthritic score reached by each mouse during the clinical course of the disease. At the time of death, hind paws are dissected free and processed for histologic examination or for RT-PCR. The histologic severity of the arthritis is scored on a scale of 0–3 for synovial proliferation and inflammatory cell infiltration, where a score of 0=normal and 3=severe.

For mice receiving intra-synovial injection of control of test adenovirus vector, the level of arthritis observed between contralateral sites is compared. In addition, the overall joint score minus that of the injected joint for the entire animal is compared with that observed in the joint injected with the control or test adenovirus vector.

Local administration of Fas-ligand adenovirus expression vectors will result in clearance of activated cells, as assessed by measuring the relative levels of CD80 mRNA by quantitative RT-PCR. This treatment also will lead to an enhanced level. Also, whether such level of apoptosis identified in affected mouse synovial tissue is assessed by the TUNEL assay ("Terminal deoxynucleotidyl transferase (TdT)-mediated dUTP Nick End Labeling"). TUNEL is performed by immersing the sections in TdT buffer (30 mM Tris-HCl, pH 7.2, 140 nM sodium cacodylate, 1 mM cobalt chloride), and then adding TdT (GIBCO BRL, Grand Island, N.Y.) and biotinylated dUTP (Boehringer Mannheim, Indianapolis, Ind.). The reaction is terminated by immersing the sections in TB buffer (300 mM sodium chloride, 30 mM sodium citrate). Subsequently, the samples are treated with peroxidase-labeled streptavidin and then visualized using the VECTASTAIN ABC kit (Vector Laboratories Inc., Burlingame, Calif.). For immunohistochemistry, the sections are blocked with 4% skim milk for 30 minutes at room temperature, then incubated with biotinylated mAbs specific for mouse CD3, B220, CD80, or CD95 (Fas). These antibodies are available from Pharmingen (San Diego, Calif.).

b. Treatment of Rheumatoid Arthritis Patients with a Gene Therapy Vector Encoding an Accessory Molecule Ligand, Fas Ligand Candidate Fas-ligand constructs identified as having potential therapeutic benefit are used in human protocols to treat RA. Human protocols encompass either in vivo or ex vivo methods to deliver the Fas-ligand constructs. Furthermore, the Fas-ligand constructs are potentially delivered by either viral or non-viral methods. Outlines of therapeutic strategies are described below.

an ex vivo therapy is similar to a protocol described for intra-articular transplantation of autologous synoviocytes retrovirally transduced to synthesize interleukin-1 receptor antagonist (Evan, Christopher et al., Clinical Trail to Assess the Safety, Feasibility, and Efficacy of Transferring a Potentially Anti-Arthritic Cytokine Gene to Human Joints with Rheumatoid arthritis, Human Gene Therapy, Vol. 7, 1261–1280). In this procedure, after clinical diagnosis of RA, the synovium is harvested during total joint replacement. The synoviocytes re-isolated and expanded, then transduced or transfected with heterologous Fas-ligand into synoviocytes (via retrovirus, adenovirus, naked DNA, etc.). The gene-modified synoviocytes are then reinjected into the patient, who is monitored and tested for amelioration of RA-associated symptoms, and for expression and function of the Fas-ligand in modified synoviocytes.

In another ex vivo protocol, an allogeneic immortalized cell line that stably expresses the heterologous Fas-ligand is administered to the RA patient. In this protocol, a stable immortalized cell line expressing Fas-ligand (introduced by transfection of the gene into the cell by nonviral methods, such as electroporation), or by viral transduction of the gene into the cell) is constructed. The modified cell line is injected into the patient, who is monitored and tested for amelioration of RA associated symptoms, and for expression and function of the hFas-ligand in modified synoviocytes.

An ex vivo therapy is similar to a protocol described for intra-articular transplantation of autologous synoviocytes retrovirally transduced to synthesize interleukin-1 receptor antagonist (Evan, Christopher et al., Clinical Trial to Assess the Safety, Feasibility, and Efficiency of Transferring a Potentially Anti-Arthritic Cytokine Gene to Human Joints with Rheumatoid Arthritis, *Human Gene Therapy*, Vol. 7, 1261–1280).

What is claimed is:

1. A method for expressing a chimeric CD40 ligand in a CD40+ human cell, wherein the chimeric CD40 ligand includes one or more human CD40 ligand domains and one or more mouse CD40 ligand domains the method comprising introducing a chimeric polynucleotide a chimeric polynucleotide encoding the chimeric CD40 ligand into the cell.

2. The method of claim 1 wherein the mouse CD40 ligand domain comprises an extracellular CD40 ligand domain.

3. The method of claim 1 wherein the mouse CD40 ligand domain comprises Domain III of the mouse CD40 ligand.

4. The method of claim 2 wherein the extracellular CD40 ligand domain consists of Domain IV.

5. The method of claim 1 wherein the mouse CD40 ligand domain consists of Domain I of the mouse CD40 ligand.

6. The method of claim 1 wherein the mouse CD40 ligand domain consists of Domain II of the mouse CD40 ligand.

7. The method of claim 1 wherein the chimeric polynucleotide consists of the nucleic acid sequence of SEQ ID NO: 3.

8. The method of claim 1 wherein the chimeric polynucleotide consists of the nucleic acid sequence of SEQ ID NO: 20.

9. The method of claim 1, wherein the human CD40+ cell comprises a neoplastic cell.

10. The method of claim 9, wherein the neoplastic cell comprises a neoplastic B cell.

11. The method of claim 9 wherein the neoplastic cell comprises a neoplastic T cell.

12. The method of claim 1 wherein the chimeric polynucleotide consists of nucleic acid sequence of SEQ ID NO: 4.

13. The method of claim 1 wherein the chimeric polynucleotide consists of nucleic acid sequence of SEQ ID NO: 5.

14. The method of claim 1 wherein the chimeric polynucleotide consists of nucleic acid sequence of SEQ ID NO: 6.

15. The method of claim 1 wherein the chimeric polynucleotide consists of nucleic acid sequence of SEQ ID NO: 7.

* * * * *